US010414813B2

(12) United States Patent
Perreault et al.

(10) Patent No.: US 10,414,813 B2
(45) Date of Patent: Sep. 17, 2019

(54) MINOR HISTOCOMPATIBILITY ANTIGENS AND USES THEREOF

(71) Applicants: UNIVERSITÉ DE MONTRÉAL, Montréal, Québec (CA); RSEM, LIMITED PARTNERSHIP, Montréal, Québec (CA)

(72) Inventors: Claude Perreault, Québec (CA); Diana Paola Granados, Québec (CA); Jean-Sébastien Delisle, Québec (CA); Pierre Thibault, Québec (CA); Sébastien Lemieux, Québec (CA)

(73) Assignees: UNIVERSITÉ DE MONTRÉAL, Montréal (CA); RSEM, LIMITED PARTNERSHIP, Montréal (CA)

( * ) Notice: Subject to any disclaimer, the term of this patent is extended or adjusted under 35 U.S.C. 154(b) by 0 days.

(21) Appl. No.: 15/548,749

(22) PCT Filed: Feb. 9, 2016

(86) PCT No.: PCT/CA2016/050116
§ 371 (c)(1),
(2) Date: Aug. 3, 2017

(87) PCT Pub. No.: WO2016/127249
PCT Pub. Date: Aug. 18, 2016

(65) Prior Publication Data
US 2018/0030112 A1    Feb. 1, 2018

Related U.S. Application Data

(60) Provisional application No. 62/113,727, filed on Feb. 9, 2015.

(51) Int. Cl.
| | |
|---|---|
| C07K 7/06 | (2006.01) |
| C07K 7/08 | (2006.01) |
| C07K 14/74 | (2006.01) |
| A61K 35/13 | (2015.01) |
| A61K 35/17 | (2015.01) |
| A61K 39/00 | (2006.01) |
| C07K 1/04 | (2006.01) |
| A61K 35/12 | (2015.01) |

(52) U.S. Cl.
CPC ........ *C07K 14/70539* (2013.01); *A61K 35/13* (2013.01); *A61K 35/17* (2013.01); *A61K 39/0011* (2013.01); *C07K 1/047* (2013.01); *C07K 7/06* (2013.01); *C07K 7/08* (2013.01); *A61K 39/00* (2013.01); *A61K 2035/124* (2013.01); *A61K 2039/505* (2013.01); *A61K 2039/5158* (2013.01); *C07K 2319/02* (2013.01); *G01N 2333/70539* (2013.01)

(58) Field of Classification Search
CPC ....... C07K 14/70539; C07K 7/06; C07K 7/08
USPC ...................................................... 514/21.5
See application file for complete search history.

(56) References Cited

U.S. PATENT DOCUMENTS

2003/0108920 A1   6/2003   Zhang et al.
2008/0207497 A1   8/2008   Ramakrishna et al.

FOREIGN PATENT DOCUMENTS

| EP | 1020519 A1 | 7/2000 | |
|---|---|---|---|
| WO | 99/05174 A1 | 2/1999 | |
| WO | 03/062401 A2 | 7/2003 | |
| WO | WO 03/062401 A2 | 7/2003 | |
| WO | 02/36750 A2 | 5/2005 | |
| WO | WO 2007/053644 A2 | 5/2007 | |
| WO | 2010/116375 A1 | 10/2010 | |
| WO | 2014/026277 A1 | 2/2014 | |
| WO | WO 2014141683 | * 9/2014 | ............. C12N 15/00 |

OTHER PUBLICATIONS

Larsen et al. (2010). Identification of CD8+ T Cell Epitopes in the West Nile Virus Polyprotein by Reverse-Immunology Using NetCTL. PLoS ONE 5(9): e12697.
Stranzl et al. (2010). NetCTLpan: pan-specific MHC class I pathway epitope predictions. Immunogenetics. 62(6):357-368.
Larsen, Malene Erup. Bioinformatics in transplantation immunology. PhD Thesis. Center for Biological Sequence Analysis, Department of Systems Biology, Technical University of Denmark, Sep. 2010.
Halling-Brown et al. (2006). SiPep: a system for the prediction of tissue-specific minor histocompatibility antigens. Int J Immunogenet. 33(4):289-295.
Deluca et al. (2009). High-throughput minor histocompatibility antigen prediction. Bioinformatics vol. 25 No. 18 2009, pp. 2411-2417.
Lundegaard et al. (2012) Predictions versus high-throughput experiments in T-cell epitope discovery: competition or synergy? Expert Rev Vaccines. 11(1):43-54.
Larsen et al. (2005). An integrative approach to CTL epitope prediction: a combined algorithm integrating MHC class I binding, TAP transport efficiency, and proteasomal cleavage predictions. Eur J Immunol. 35(8):2295-2303.
Tenzer et al. (2005). Modeling the MHC class I pathway by combining predictions of proteasomal cleavage, TAP transport and MHC class I binding. Cell Mol Life Sci. 62(9):1025-1037.

(Continued)

*Primary Examiner* — Yan Xiao
(74) *Attorney, Agent, or Firm* — James S. Keddie; Bozicevic, Field & Francis LLP

(57) ABSTRACT

Novel minor histocompatibility antigens (MiHAs) are described. These novel MiHAs were selected based on two features: (i) they are encoded by loci with a minor allele frequency (MAF) of at least 0.05; and (ii) they have adequate tissue distribution. Compositions, nucleic acids and cells related to these novel MiHAs are also described. The present application also discloses the use of these novel MiHAs, and related compositions, nucleic acids and cells, in applications related to cancer immunotherapy, for example for the treatment of hematologic cancers such as leukemia.

18 Claims, 12 Drawing Sheets

Specification includes a Sequence Listing.

(56) References Cited

OTHER PUBLICATIONS

Reche Pa and Reinherz El. (2005). PEPVAC: a web server for multi-epitope vaccine development based on the prediction of supertypic MHC ligands. Nucleic Acids Research, 2005, vol. 33, Web Server issue, W138-W142.
Jarmalavicius et al. (2012). High immunogenicity of the human leukocyte antigen peptidomes of melanoma tumor cells. J Biol Chem. 287(40):33401-33411. Epub Aug. 6, 2012.
Schuler et al. (2005) "SNEP: SNP-derived Epitope Prediction program for minor H antigens", Immunogenetics. 57: 816-820.
Yewdell et al. 2003. Making sense of mass destruction: quantitating MHC class I antigen presentation. Nature Rev. Immunol., 2003, 3:952-961.
Yewdell et al., DRiPs solidify: progress in understanding endogenous MHC class I antigen processing. Trends Immunol., 2011, 32:548-558.
Yu et al., A precisely regulated gene expression cassette potently modulates metastasis and survival in multiple solid cancers. PLoS. Genet., 2008, 4, e1000129.
Meunier et al., Two host factors regulate persistence of H7a-specific T cells injected in tumor bearing mice. PLoS One, 2009, 4:e4116.
Molldrem et al., Graft-vs.-leukemia effects. In Graft-vs.-host disease. J.L.M.Ferrara, K.R.Cooke, and H.J.Deeg, editors. Marcel Dekker, New York. 155-194, 2005.
Mullally et al., Beyond HLA: the significance of genomic variation for allogeneic hematopoietic stem cell transplantation. Blood, 2007, 109:1355-1362.
Murata et al., A human minor histocompatibility antigen resulting from differential expression due to a gene deletion. J.Exp.Med., 2003, 197:1279-1289.
Neefjes et al., Towards a systems understanding of MHC class I and MHC class II antigen presentation. Nat.Rev. Immunol., 2011, 11:823-836.
Nusbaum et al. DNA sequence and analysis of human chromosome 8. Nature Letters, vol. 439/19, Jan. 2006, pp. 331-335.
O'Brien et al., CENP-F expression is associated with poor prognosis and chromosomal instability in patients with primary breast cancer. Int J Cancer, 2007, 120, 1434-1443.
Oishi et al., RMD-1, a novel microtubule-associated protein, functions in chromosome segregation in Caenorhabditis elegans. J Cell Biol., 2007, 179, 1149-1162.
O'Reilly et al., Adoptive transfer of unselected or leukemia-reactive T-cells in the treatment of relapse following allogeneic hematopoietic cell transplantation. Semin.Immunol., 2010, 22:162-172.
Patrick et al., Stress-induced NQO1 controls stability of C/EBPalpha against 20S proteasomal degradation to regulate p63 expression with implications in protection against chemical-induced skin cancer. Oncogene. 2012, 31:4362-4371.
PCT International Search Report and Written Opinion in respect of PCT application No. PCT/CA2016/050116, dated Mar. 23, 2016.
Perreault et al., Minor histocompatibility antigens. Blood, 1990, 76:1269-1280.
Perreault et al., Adoptive cancer immunotherapy: discovering the best targets. J.Mol.Med., 2002, 80:212-218.
Perreault et al., The origin and role of MHC class I-associated self-peptides. Prog.Mol Biol.Transl.Sci., 2010, 92:41-60.
Popovic et al., The only proposed T-cell epitope derived from the TEL-AML1 translocation is not naturally processed. Blood, 2011, 118:946-954.
Rezvani eta al., Characterizing and optimizing immune responses to leukaemia antigens after allogeneic stem cell transplantation. Best. Pract.Res.Clin.Haematol., 2008 21:437-453.
Rijke et al., A frameshift polymorphism in P2X5 elicits an allogeneic cytotoxic T lymphocyte response associated with remission of chronic myeloid leukemia. J.Clin.Invest, 2005, 115:3506-3516.
Roopenian e al., The immunogenomics of minor histocompatibility antigens. Immunol.Rev., 2002, 190:86-94.
Rosenberg et al., Cancer immunotherapy: moving beyond current vaccines. Nat Med., 2004, 10:909-915.
Rosenberg et al., Durable complete responses in heavily pretreated patients with metastatic melanoma using T cell transfer immunotherapy. Clin.Cancer Res., 2011, 17:4550-4557.
Schreiber et al., Targeting mutations predictably. Blood, 2011, 118:830-831.
Schuler et al., SNEP: SNP-derived Epitope Prediction program for minor H antigens. Immunogenetics, 2005. 57: 816-820.
Sherry et al., dbSNP: the NCBI database of genetic variation. Nucleic Acids Res., 2001, 29, 308-311.
Shlomchik, W.D. Graft-versus-host disease. Nat.Rev.Immunol., 2007, 7:340-352.
Slager et al., Identification of the angiogenic endothelial-cell growth factor-1/thymidine phosphorylase as a potential target for immunotherapy of cancer. Blood, 2006, 107:4954-4960.
Socie et al., Acute graft-versus-host disease; from the bench to the bedside. Blood, 2009, 114:4327-4336.
Spaapen et al., Toward targeting B cell cancers with CD4+ CTLs: identification of a CD19-encoded minor histocompatibility antigen using a novel genome-wide analysis. J Exp.Med, 2008, 205:2863-2872.
Spaapen et al., Rapid identification of clinical relevant minor histocompatibility antigens via genome-wide zygosity-genotype correlation analysis. Clin.Cancer Res., 2009, 15:7137-7143.
Spierings et al., Phenotype frequencies of autosomal minor histocompatibility antigens display significant differences among populations. PLoS.Genet., 2007, 3:e103.
Spierings et al., The minor histocompatibility antigen HA-3 arises from differential proteasome-mediated cleavage of be lymphoid blast crisis (Lbc) oncoprotein. Blood, 2003, 102:621-629.
Stumpf et al., Identification of 4 new HLA-DR-restricted minor histocompatibility antigens as hematopoietic targets in antitumor immunity. Blood, 2009, 114:3684-3692.
Sykes et al., Transplantation Immunology. In Fundamental Immunology. W.E.Paul, editor. Lippincott Williams & Wilkins, Philadelphia. 1426-1488, 2008.
Takahashi et al., Regression of human kidney cancer following allogeneic stem cell transplantation is associated with recognition of an HERV-E antigen by T cells. J.Clin.Invest., 2008, 118:1099-1109.
Thomas, E.D. 2005 Foreword. In Graft-vs.-host disease. 3rd edition. J.L.M.Ferrara, K.R.Coke, and H.J.Deeg, editors. Marcel Dekker, New York. pp. iii-iv.
Tosato et al., Generation of Epstein-Barr Virus (EBV)-immortalized B cell lines. Curr. Protoc. Immunol. Chapter 7, Unit 7.22, 2007.
Tykodi et al., Allogeneic hematopoietic cell transplantation for metastatic renal cell carcinoma after nonmyeloablative conditioning: toxicity, clinical response, and immunological response to minor histocompatibility antigens. Clin.Cancer Res., 2004, 10:7799-7811.
Tykodi et al. C19orf48 encodes a minor histocompatibility antigen recognized by CD48 cytotoxic T cells from renal cell carcinoma patients. Clin Cancer Res 2008;14(16) Aug. 15, 2008, pp. 5260-5269.
Urbanucci et al., Overexpression of androgen receptor enhances the binding of the receptor to the chromatin in prostate cancer. Oncogene, 2012 31, 2153-2163.
Van Bergen et al., Multiple myeloma—reactive T cells recognize an activation-induced minor histocompatibility antigen encoded by the ATP-dependent interferon-responsive (ADIR) gene. Blood, 2007, 109:4089-4096.
Van Bergen et al., High-throughput characterization of 10 new minor histocompatibility antigens by whole genome association scanning. Cancer Res., 2010, 70:9073-9083.
Vincent et al., Next-generation leukemia immunotherapy. Blood 118:2951-2959, 2011.
Vita et al., The immune epitope database 2.0. Nucleic Acids Res., 2010, 38, D854-D862.
Vogelsang et al., Pathogenesis and treatment of graft-versus-host disease after bone marrow transplant. Annu. Rev.Med., 2003, 54:29-52.
Wakai et al., Prognostic significance of NQO1 expression in intrahepatic cholangiocarcinoma. Int. J Clin. Exp Pathol., 2011, 4, 363-370.

(56) References Cited

OTHER PUBLICATIONS

Warren et al., An antigen produced by splicing of noncontiguous peptides in the reverse order. Science, 2006, 313:1444-1447.
Warren et al., Therapy of relapsed leukemia after allogeneic hematopoietic cell transplant with T cells specific for minor histocompatibility antigens. Blood, 2010, 115:3869-3878.
Xiang et al., Identification of E74-like factor 1 (ELF1) as a transcriptional regulator of the Hox cofactor MEIS1. Exp. Hematol., 2010, 38, 798-8, 808.
Yang et al., Allograft rejection mediated by memory T cells is resistant to regulation. Proc.Natl.Acad.Sci.U.S.A, 2007, 104:19954-19959.
Yang et al., Expression of Elf-1 and survivin in non-small cell lung cancer and their relationship to intratumoral microvessel density. Chin J. Cancer, 2010, 29, 396-402.
Yang et al., NAD(P)H quinone oxidoreductase 1 (NQO1) genetic C609T polymorphism is associated with the risk of digestive tract cancer a meta-analysis based on 21 case-control studies. Eur J Cancer Prev. Sep. 2012;21(5):432-41.
Akatsuka et al., Identification of a polymorphic gene, BCL2A1, encoding two novel hematopoietic lineage-specific minor histocompatibility antigens. J.Exp.Med, 2003, 197:1489-1500.
Akatsuka et al., Minor histocompatibility antigens as targets for immunotherapy using allogeneic immune reactions. Cancer Sci., 2007, 98(8): 1139-1146.
Andrews et al., Oncogenic activation of the human Pygopus2 promoter by E74-like factor-1. Mol. Cancer Res., 2008, 6, 259-266.
Barrett ,A.J. Understanding and harnessing the graft-versus-leukaemia effect. Br.J.Haematol, 2008, 142:877-888.
Bencimon et al., Prevalence of anticentromere F protein autoantibodies in 347 patients with non-Hodgkin's lymphoma. Ann. N. Y. Acad. Sci., 2005, 1050, 319-326.
Bishop et al., Allogeneic lymphocytes induce tumor regression of advanced metastatic breast cancer. J.Clin.Oncol., 2004, 22:3886-3892.
Bleakley et al., Molecules and mechanisms of the graft-versus-leukaemia effect. Nat.Rev.Cancer, 2004, 4:371-380.
Bleakley et al., Exploiting T cells specific for human minor histocompatibility antigens for therapy of leukemia. Immunol.Cell Biol., 2011, 89:396-407.
Brickner et al., The immunogenicity of a new human minor histocompatibility antigen results from differential antigen processing. J.Exp.Med., 2001, 193:195-205.
Brickner et al., The PANE1 gene encodes a novel human minor histocompatibility antigen that is selectively expressed in B-lymphoid cells and B-CLL. Blood, 2006, 107:3779-3786.
Brickner, A.G. Mechanisms of minor histocompatibility antigen immunogenicity: the role of infinitesimal versus structurally profound polymorphisms. Immunol.Res., 2006, 36:33-41.
Caron et al., The MHC I immunopeptidome conveys to the cell surface an integrative view of cellular regulation. Mol. Syst.Biol., 2011, 7:533.
Chen et al., Centromere protein F and survivin are associated with high risk and a poor prognosis in colorectal gastrointestinal stromal tumours. J Clin. Pathol., 2011, 64, 751-755.
Childs et al., Nonmyeloablative allogeneic immunotherapy for solid tumors. Annu.Rev.Med., 2004, 55:459-475.
De La Guardia et al., CENP-F gene amplification and overexpression in head and neck squamous cell carcinomas. Head Neck, 2001, 23, 104-112.
De Verteuil et al., Deletion of immunoproteasome subunits imprints on the transcriptome and has a broad impact an peptides presented by major histocompatibility complex I molecules. Mol Cell Proteomics, 2010, 9:2034-2047.
De Verteuil et al., Origin and plasticity of MHC I-associated self peptides. Autoimmun.Rev. Epub Nov. 2011.
Den Haan et al., Identification of a graft versus host disease-associated human minor histocompatibility antigen. Science, 1995, 268:1476-1480.

Den Haan et al. The minor histocompatibility antigen HA-1: a diallelic gene with a single amino acid polymorphism. Science, 1998, 279:1054-1057.
Ding et al., Association of NQO1 rs1800566 polymorphism and the risk of colorectal cancer: a meta-analysis. Int. J Colorectal Dis., 2012, 27, 885-892.
Dolstra et al., A human minor histocompatibility antigen specific for B cell acute lymphoblastic leukemia. J.Exp. Med., 1999, 189:301-308.
Endo et al., Terf/TRIM17 stimulates degradation of kinetochore protein ZWINT and regulates cell proliferation. J. Biochem., 2012, 151, 139-144.
Feng et al., Targeting minor histocompatibility antigens in graft versus tumor or graft versus leukemia responses. Trends Immunol., 2008, 29:624-632.
Ferrara et al., Graft-versus-host disease. Lancet, 2009, 373:1550-1561.
Fontaine et al., Adoptive transfer of minor histocompatibility antigen-specific T lymphocytes eradicates leukemia cells without causing graft-versus-host disease. Nat.Med., 2001, 7:789-794.
Fortier et al., The MHC class I peptide repertoire is molded by the transcriptome. J.Exp.Med., 2008, 205:595-610.
Granados et al., MHC I-associated peptides preferentially derive from transcripts bearing miRNA recognition elements. Blood Epub Mar. 21, 2012.
Greinix et al., Diagnosis and staging of chronic graft-versus-host disease in the clinical practice. Biol.Blood Marrow Transplant., 2011, 17:167-175.
Griffioen et al., Identification of phosphatidylinositol 4-kinase type II beta as HLA class IL-restricted target in graft versus leukemia reactivity. Proc.Natl.Acad.Sci.U.S.A, 2008, 105:3837-3842.
Grinberg et al., Mitochondrial carrier homolog 2 is a target of tBID in cells signaled to die by tumor necrosis factor alpha. Mol. Cell Biol., 2005, 25, 4579-4590.
Hanahan et al., Hallmarks of cancer: the next generation. Cell, 2011, 144:646-674.
Ho et al., Deregulation of rab and rab effector genes in bladder cancer. PLoS. ONE., 2012, 7, e39469.
Hombrink et al. High-throughput identification of potential minor histocompatibility antigens by MHC tetramer-based screening: feasibility and limitations. Plos One, Aug. 2011, vol. 6, No. 8, pp. 1-12.
Horowitz et al., Graft-versus-leukemia reactions after bone marrow transplantation. Blood, 1990, 75:555-562.
Huang et al., An NQO1 substrate with potent antitumor activity that selectively kills by PARP1-induced programmed necrosis. Cancer Res. Jun. 15, 2012;72(12):3038-47. Epub Apr. 24, 2012.
Inaba et al., Primed T cells are more resistant to Fas-mediated activation-induced cell death than naive T cells. J Immunol, 1999, 163:1315-1320.
Jamieson et al., Two minor NQO1 and NQO2 alleles predict poor response of breast cancer patients to adjuvant doxorubicin and cyclophosphamide therapy. Pharmacogenet. Genomics, 2011, 21, 808-819.
Kamei et al., HapMap scanning of novel human minor histocompatibility antigens. Blood, 2009, 113:5041-5048.
Karosiene et al., NetMHCcons: a consensus method for the major histocompatibility complex class I predictions. Immunogenetics, 2011.
Katz et al., Molecular basis of the interaction between proapoptotic truncated BID (tBID) protein and mitochondria carrier homologue 2 (MTCH2) protein: key players in mitochondrial death pathway. J. Biol. Chem., 2012, 287, 15016-15023.
Kawase et al., Alternative splicing due to an intronic SNP in HMSD generates a novel minor histocompatibility antigen. Blood, 2007, 110:1055-1063.
Kawase et al., Identification of human minor histocompatibility antigens based on genetic association with highly parallel genotyping of pooled DNA. Blood, 2008 111:3286-3294.
Kessler et al., Identification of T-cell epitopes for cancer immunotherapy. Leukemia, 2007, 21:1859-1874.

(56) References Cited

OTHER PUBLICATIONS

Kolb et al., Graft-versus-leukemia effect of donor lymphocyte transfusions in marrow grafted patients. European Group for Blood and Marrow Transplantation Working Party Chronic Leukemia. Blood, 1995, 86:2041-2050.
Kolb, H.-J. Graft-versus-leukemia effects of transplantation and donor lymphocytes. Blood, 2008, 112:4371-4383.
Kolesar et al., The NQO1*2/*2 polymorphism is associated with poor overall survival in patients following resection of stages II and IIIa non-small cell lung cancer. Oncol. Rep., 2011, 25, 1765-1772.
Loveland et al.,The non-MHC transplantation antigens—neither weak nor minor. Immunol. Today, 1986, 7:223-229.
Mason, D. A very high level of crossreactivity is an essential feature of the T-cell receptor. Immunol. Today, 1998, 19:395-404.
Massague, J., TGFb in Cancer. Cell, 2008, 134:215-230.
Meunier et al., T cells targeted against a single minor histocompatibility antigen can cure solid tumors. Nat.Med., 2005, 11:1222-1229.

\* cited by examiner

SEQUENCE LISTING

<160> NUMBER OF SEQ ID NOS: 284

<210> SEQ ID NO 1
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Arg or Cys

<400> SEQUENCE: 1

```
Lys Ile Leu Glu Lys Glu Ile Xaa Val
1               5

<210> SEQ ID NO 2
<211> LENGTH: 9
<212> TYPE: PRT
<213> ORGANISM: Homo sapiens

<400> SEQUENCE: 2

Lys Ile Leu Glu Lys Glu Ile Arg Val
1               5

<210> SEQ ID NO 3
<211> LENGTH: 9
<212> TYPE: PRT
<213> ORGANISM: Homo sapiens

<400> SEQUENCE: 3

Lys Ile Leu Glu Lys Glu Ile Cys Val
1               5

<210> SEQ ID NO 4
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Ala or Pro

<400> SEQUENCE: 4

His Leu Glu Glu Gln Ile Xaa Lys Val
1               5

<210> SEQ ID NO 5
<211> LENGTH: 9
<212> TYPE: PRT
<213> ORGANISM: Homo sapiens

<400> SEQUENCE: 5

His Leu Glu Glu Gln Ile Ala Lys Val
1               5

<210> SEQ ID NO 6
<211> LENGTH: 9
<212> TYPE: PRT
<213> ORGANISM: Homo sapiens

<400> SEQUENCE: 6

His Leu Glu Glu Gln Ile Pro Lys Val
1               5

<210> SEQ ID NO 7
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ala or Ser

<400> SEQUENCE: 7

Xaa Glu Ile Glu Gln Lys Ile Lys Glu Tyr
1               5                   10

<210> SEQ ID NO 8
```

```
<211> LENGTH: 10
<212> TYPE: PRT
<213> ORGANISM: Homo sapiens

<400> SEQUENCE: 8

Ala Glu Ile Glu Gln Lys Ile Lys Glu Tyr
1               5                   10

<210> SEQ ID NO 9
<211> LENGTH: 10
<212> TYPE: PRT
<213> ORGANISM: Homo sapiens

<400> SEQUENCE: 9

Ser Glu Ile Glu Gln Lys Ile Lys Glu Tyr
1               5                   10

<210> SEQ ID NO 10
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Val or Ile

<400> SEQUENCE: 10

Glu Glu Ile Pro Xaa Ser Ser His Tyr
1               5

<210> SEQ ID NO 11
<211> LENGTH: 9
<212> TYPE: PRT
<213> ORGANISM: Homo sapiens

<400> SEQUENCE: 11

Glu Glu Ile Pro Val Ser Ser His Tyr
1               5

<210> SEQ ID NO 12
<211> LENGTH: 9
<212> TYPE: PRT
<213> ORGANISM: Homo sapiens

<400> SEQUENCE: 12

Glu Glu Ile Pro Ile Ser Ser His Tyr
1               5

<210> SEQ ID NO 13
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Val or Ile

<400> SEQUENCE: 13

Glu Glu Ile Pro Xaa Ser Ser His Tyr Phe
1               5                   10

<210> SEQ ID NO 14
<211> LENGTH: 10
<212> TYPE: PRT
<213> ORGANISM: Homo sapiens

<400> SEQUENCE: 14
```

```
Glu Glu Ile Pro Val Ser Ser His Tyr Phe
1               5                   10

<210> SEQ ID NO 15
<211> LENGTH: 10
<212> TYPE: PRT
<213> ORGANISM: Homo sapiens

<400> SEQUENCE: 15

Glu Glu Ile Pro Ile Ser Ser His Tyr Phe
1               5                   10

<210> SEQ ID NO 16
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Glu or Ala

<400> SEQUENCE: 16

Ala Xaa Ile Gln Glu Lys Lys Glu Ile
1               5

<210> SEQ ID NO 17
<211> LENGTH: 9
<212> TYPE: PRT
<213> ORGANISM: Homo sapiens

<400> SEQUENCE: 17

Ala Glu Ile Gln Glu Lys Lys Glu Ile
1               5

<210> SEQ ID NO 18
<211> LENGTH: 9
<212> TYPE: PRT
<213> ORGANISM: Homo sapiens

<400> SEQUENCE: 18

Ala Ala Ile Gln Glu Lys Lys Glu Ile
1               5

<210> SEQ ID NO 19
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Asn or Asp
<220> FEATURE:
<221> NAME/KEY: MISC_FEATURE
<222> LOCATION: (5)..(5)
<223> OTHER INFORMATION: Xaa is Gln or His

<400> SEQUENCE: 19

Gln Glu Xaa Ile Xaa Asn Leu Gln Leu
1               5

<210> SEQ ID NO 20
<211> LENGTH: 9
<212> TYPE: PRT
<213> ORGANISM: Homo sapiens

<400> SEQUENCE: 20
```

```
Gln Glu Asn Ile Gln Asn Leu Gln Leu
1               5

<210> SEQ ID NO 21
<211> LENGTH: 9
<212> TYPE: PRT
<213> ORGANISM: Homo sapiens

<400> SEQUENCE: 21

Gln Glu Asn Ile His Asn Leu Gln Leu
1               5

<210> SEQ ID NO 22
<211> LENGTH: 9
<212> TYPE: PRT
<213> ORGANISM: Homo sapiens

<400> SEQUENCE: 22

Gln Glu Asp Ile Gln Asn Leu Gln Leu
1               5

<210> SEQ ID NO 23
<211> LENGTH: 9
<212> TYPE: PRT
<213> ORGANISM: Homo sapiens

<400> SEQUENCE: 23

Gln Glu Asp Ile His Asn Leu Gln Leu
1               5

<210> SEQ ID NO 24
<211> LENGTH: 10
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Asn or His

<400> SEQUENCE: 24

Val Glu Glu Ala Asp Gly Xaa Lys Gln Trp
1               5                   10

<210> SEQ ID NO 25
<211> LENGTH: 10
<212> TYPE: PRT
<213> ORGANISM: Homo sapiens

<400> SEQUENCE: 25

Val Glu Glu Ala Asp Gly Asn Lys Gln Trp
1               5                   10

<210> SEQ ID NO 26
<211> LENGTH: 10
<212> TYPE: PRT
<213> ORGANISM: Homo sapiens

<400> SEQUENCE: 26

Val Glu Glu Ala Asp Gly His Lys Gln Trp
1               5                   10

<210> SEQ ID NO 27
<211> LENGTH: 10
<212> TYPE: PRT
<213> ORGANISM: Homo sapiens
<220> FEATURE:
```

```
<221> NAME/KEY: MISC_FEATURE
<222> LOCATION: (6)..(6)
<223> OTHER INFORMATION: Xaa is Asn or His

<400> SEQUENCE: 27

Glu Glu Ala Asp Gly Xaa Lys Gln Trp Trp
1               5                   10

<210> SEQ ID NO 28
<211> LENGTH: 10
<212> TYPE: PRT
<213> ORGANISM: Homo sapiens

<400> SEQUENCE: 28

Glu Glu Ala Asp Gly Asn Lys Gln Trp Trp
1               5                   10

<210> SEQ ID NO 29
<211> LENGTH: 10
<212> TYPE: PRT
<213> ORGANISM: Homo sapiens

<400> SEQUENCE: 29

Glu Glu Ala Asp Gly His Lys Gln Trp Trp
1               5                   10

<210> SEQ ID NO 30
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Glu or Gly

<400> SEQUENCE: 30

Glu Xaa Arg Gly Glu Asn Thr Ser Tyr
1               5

<210> SEQ ID NO 31
<211> LENGTH: 9
<212> TYPE: PRT
<213> ORGANISM: Homo sapiens

<400> SEQUENCE: 31

Glu Glu Arg Gly Glu Asn Thr Ser Tyr
1               5

<210> SEQ ID NO 32
<211> LENGTH: 9
<212> TYPE: PRT
<213> ORGANISM: Homo sapiens

<400> SEQUENCE: 32

Glu Gly Arg Gly Glu Asn Thr Ser Tyr
1               5

<210> SEQ ID NO 33
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Arg or Cys

<400> SEQUENCE: 33
```

Ser Glu Ser Lys Ile Xaa Val Leu Leu
1               5

<210> SEQ ID NO 34
<211> LENGTH: 9
<212> TYPE: PRT
<213> ORGANISM: Homo sapiens

<400> SEQUENCE: 34

Ser Glu Ser Lys Ile Arg Val Leu Leu
1               5

<210> SEQ ID NO 35
<211> LENGTH: 9
<212> TYPE: PRT
<213> ORGANISM: Homo sapiens

<400> SEQUENCE: 35

Ser Glu Ser Lys Ile Cys Val Leu Leu
1               5

<210> SEQ ID NO 36
<211> LENGTH: 9
<212> TYPE: PRT
<213> ORGANISM: Homo sapiens

<400> SEQUENCE: 36

Asn Glu Ser Asn Thr Gln Lys Thr Tyr
1               5

<210> SEQ ID NO 37
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Arg or Ile

<400> SEQUENCE: 37

Glu Glu Ile Asn Leu Gln Xaa Asn Ile
1               5

<210> SEQ ID NO 38
<211> LENGTH: 9
<212> TYPE: PRT
<213> ORGANISM: Homo sapiens

<400> SEQUENCE: 38

Glu Glu Ile Asn Leu Gln Arg Asn Ile
1               5

<210> SEQ ID NO 39
<211> LENGTH: 9
<212> TYPE: PRT
<213> ORGANISM: Homo sapiens

<400> SEQUENCE: 39

Glu Glu Ile Asn Leu Gln Ile Asn Ile
1               5

<210> SEQ ID NO 40
<211> LENGTH: 11
<212> TYPE: PRT
<213> ORGANISM: Homo sapiens

```
<220> FEATURE:
<221> NAME/KEY: MISC_FEATURE
<222> LOCATION: (8)..(8)
<223> OTHER INFORMATION: Xaa is Glu or Lys

<400> SEQUENCE: 40

Ser Glu Glu Ser Ala Val Pro Xaa Arg Ser Trp
1               5                   10

<210> SEQ ID NO 41
<211> LENGTH: 11
<212> TYPE: PRT
<213> ORGANISM: Homo sapiens

<400> SEQUENCE: 41

Ser Glu Glu Ser Ala Val Pro Lys Arg Ser Trp
1               5                   10

<210> SEQ ID NO 42
<211> LENGTH: 11
<212> TYPE: PRT
<213> ORGANISM: Homo sapiens

<400> SEQUENCE: 42

Ser Glu Glu Ser Ala Val Pro Glu Arg Ser Trp
1               5                   10

<210> SEQ ID NO 43
<211> LENGTH: 10
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Glu or Lys

<400> SEQUENCE: 43

Glu Glu Ser Ala Val Pro Xaa Arg Ser Trp
1               5                   10

<210> SEQ ID NO 44
<211> LENGTH: 10
<212> TYPE: PRT
<213> ORGANISM: Homo sapiens

<400> SEQUENCE: 44

Glu Glu Ser Ala Val Pro Glu Arg Ser Trp
1               5                   10

<210> SEQ ID NO 45
<211> LENGTH: 10
<212> TYPE: PRT
<213> ORGANISM: Homo sapiens

<400> SEQUENCE: 45

Glu Glu Ser Ala Val Pro Lys Arg Ser Trp
1               5                   10

<210> SEQ ID NO 46
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Glu or Asp
```

```
<400> SEQUENCE: 46

Gln Xaa Leu Ile Gly Lys Lys Glu Tyr
1               5

<210> SEQ ID NO 47
<211> LENGTH: 9
<212> TYPE: PRT
<213> ORGANISM: Homo sapiens

<400> SEQUENCE: 47

Gln Glu Leu Ile Gly Lys Lys Glu Tyr
1               5

<210> SEQ ID NO 48
<211> LENGTH: 9
<212> TYPE: PRT
<213> ORGANISM: Homo sapiens

<400> SEQUENCE: 48

Gln Asp Leu Ile Gly Lys Lys Glu Tyr
1               5

<210> SEQ ID NO 49
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Gly or Ser

<400> SEQUENCE: 49

Glu Glu Leu Leu Ala Val Xaa Lys Phe
1               5

<210> SEQ ID NO 50
<211> LENGTH: 9
<212> TYPE: PRT
<213> ORGANISM: Homo sapiens

<400> SEQUENCE: 50

Glu Glu Leu Leu Ala Val Gly Lys Phe
1               5

<210> SEQ ID NO 51
<211> LENGTH: 9
<212> TYPE: PRT
<213> ORGANISM: Homo sapiens

<400> SEQUENCE: 51

Glu Glu Leu Leu Ala Val Ser Lys Phe
1               5

<210> SEQ ID NO 52
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Asp or Gly

<400> SEQUENCE: 52

Gly Glu Xaa Lys Gly Ile Lys Ala Leu
1               5
```

<210> SEQ ID NO 53
<211> LENGTH: 9
<212> TYPE: PRT
<213> ORGANISM: Homo sapiens

<400> SEQUENCE: 53

Gly Glu Asp Lys Gly Ile Lys Ala Leu
1               5

<210> SEQ ID NO 54
<211> LENGTH: 9
<212> TYPE: PRT
<213> ORGANISM: Homo sapiens

<400> SEQUENCE: 54

Gly Glu Gly Lys Gly Ile Lys Ala Leu
1               5

<210> SEQ ID NO 55
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is His or Gln

<400> SEQUENCE: 55

Glu Glu Ala Leu Gly Leu Tyr Xaa Trp
1               5

<210> SEQ ID NO 56
<211> LENGTH: 9
<212> TYPE: PRT
<213> ORGANISM: Homo sapiens

<400> SEQUENCE: 56

Glu Glu Ala Leu Gly Leu Tyr His Trp
1               5

<210> SEQ ID NO 57
<211> LENGTH: 9
<212> TYPE: PRT
<213> ORGANISM: Homo sapiens

<400> SEQUENCE: 57

Glu Glu Ala Leu Gly Leu Tyr Gln Trp
1               5

<210> SEQ ID NO 58
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Ala or Ser

<400> SEQUENCE: 58

Ser Gln Xaa Glu Ile Glu Gln Lys Ile
1               5

<210> SEQ ID NO 59
<211> LENGTH: 9
<212> TYPE: PRT
<213> ORGANISM: Homo sapiens

```
<400> SEQUENCE: 59

Ser Gln Ala Glu Ile Glu Gln Lys Ile
1               5

<210> SEQ ID NO 60
<211> LENGTH: 9
<212> TYPE: PRT
<213> ORGANISM: Homo sapiens

<400> SEQUENCE: 60

Ser Gln Ser Glu Ile Glu Gln Lys Ile
1               5

<210> SEQ ID NO 61
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Ser or Pro

<400> SEQUENCE: 61

Thr Glu Met Glu Ile Xaa Arg Ala Ala
1               5

<210> SEQ ID NO 62
<211> LENGTH: 9
<212> TYPE: PRT
<213> ORGANISM: Homo sapiens

<400> SEQUENCE: 62

Thr Glu Met Glu Ile Ser Arg Ala Ala
1               5

<210> SEQ ID NO 63
<211> LENGTH: 9
<212> TYPE: PRT
<213> ORGANISM: Homo sapiens

<400> SEQUENCE: 63

Thr Glu Met Glu Ile Pro Arg Ala Ala
1               5

<210> SEQ ID NO 64
<211> LENGTH: 10
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Asn or Ser

<400> SEQUENCE: 64

Lys Glu Ile Asn Glu Lys Ser Xaa Ile Leu
1               5                   10

<210> SEQ ID NO 65
<211> LENGTH: 10
<212> TYPE: PRT
<213> ORGANISM: Homo sapiens

<400> SEQUENCE: 65

Lys Glu Ile Asn Glu Lys Ser Asn Ile Leu
1               5                   10
```

<210> SEQ ID NO 66
<211> LENGTH: 10
<212> TYPE: PRT
<213> ORGANISM: Homo sapiens

<400> SEQUENCE: 66

Lys Glu Ile Asn Glu Lys Ser Ser Ile Leu
1               5                   10

<210> SEQ ID NO 67
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Glu or Lys

<400> SEQUENCE: 67

Glu Xaa Glu Gln Ser Gln Ser Arg Trp
1               5

<210> SEQ ID NO 68
<211> LENGTH: 9
<212> TYPE: PRT
<213> ORGANISM: Homo sapiens

<400> SEQUENCE: 68

Glu Glu Glu Gln Ser Gln Ser Arg Trp
1               5

<210> SEQ ID NO 69
<211> LENGTH: 9
<212> TYPE: PRT
<213> ORGANISM: Homo sapiens

<400> SEQUENCE: 69

Glu Lys Glu Gln Ser Gln Ser Arg Trp
1               5

<210> SEQ ID NO 70
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Ser or Ala

<400> SEQUENCE: 70

Ala Glu Leu Gln Xaa Arg Leu Ala Ala
1               5

<210> SEQ ID NO 71
<211> LENGTH: 9
<212> TYPE: PRT
<213> ORGANISM: Homo sapiens

<400> SEQUENCE: 71

Ala Glu Leu Gln Ser Arg Leu Ala Ala
1               5

<210> SEQ ID NO 72
<211> LENGTH: 9
<212> TYPE: PRT

```
<213> ORGANISM: Homo sapiens

<400> SEQUENCE: 72

Ala Glu Leu Gln Ala Arg Leu Ala Ala
1               5

<210> SEQ ID NO 73
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Arg or Gly

<400> SEQUENCE: 73

Gln Glu Asn Gln Asp Pro Xaa Arg Trp
1               5

<210> SEQ ID NO 74
<211> LENGTH: 9
<212> TYPE: PRT
<213> ORGANISM: Homo sapiens

<400> SEQUENCE: 74

Gln Glu Asn Gln Asp Pro Arg Arg Trp
1               5

<210> SEQ ID NO 75
<211> LENGTH: 9
<212> TYPE: PRT
<213> ORGANISM: Homo sapiens

<400> SEQUENCE: 75

Gln Glu Asn Gln Asp Pro Gly Arg Trp
1               5

<210> SEQ ID NO 76
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Gly or Arg

<400> SEQUENCE: 76

Gln Glu Leu Asp Xaa Val Phe Gln Lys Leu
1               5                   10

<210> SEQ ID NO 77
<211> LENGTH: 10
<212> TYPE: PRT
<213> ORGANISM: Homo sapiens

<400> SEQUENCE: 77

Gln Glu Leu Asp Gly Val Phe Gln Lys Leu
1               5                   10

<210> SEQ ID NO 78
<211> LENGTH: 10
<212> TYPE: PRT
<213> ORGANISM: Homo sapiens

<400> SEQUENCE: 78

Gln Glu Leu Asp Arg Val Phe Gln Lys Leu
```

```
<210> SEQ ID NO 79
<211> LENGTH: 11
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: Xaa is Leu or Pro

<400> SEQUENCE: 79

Ser Leu Leu Glu Ser Ser Arg Ser Gln Glu Xaa
1               5                   10

<210> SEQ ID NO 80
<211> LENGTH: 11
<212> TYPE: PRT
<213> ORGANISM: Homo sapiens

<400> SEQUENCE: 80

Ser Leu Leu Glu Ser Ser Arg Ser Gln Glu Leu
1               5                   10

<210> SEQ ID NO 81
<211> LENGTH: 11
<212> TYPE: PRT
<213> ORGANISM: Homo sapiens

<400> SEQUENCE: 81

Ser Leu Leu Glu Ser Ser Arg Ser Gln Glu Pro
1               5                   10

<210> SEQ ID NO 82
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Val or Leu

<400> SEQUENCE: 82

Ala Leu Ser Gly His Leu Glu Thr Xaa
1               5

<210> SEQ ID NO 83
<211> LENGTH: 9
<212> TYPE: PRT
<213> ORGANISM: Homo sapiens

<400> SEQUENCE: 83

Ala Leu Ser Gly His Leu Glu Thr Val
1               5

<210> SEQ ID NO 84
<211> LENGTH: 9
<212> TYPE: PRT
<213> ORGANISM: Homo sapiens

<400> SEQUENCE: 84

Ala Leu Ser Gly His Leu Glu Thr Leu
1               5

<210> SEQ ID NO 85
<211> LENGTH: 10
```

```
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Iso or Met

<400> SEQUENCE: 85

Gln Glu Leu Glu Glu Lys Leu Asn Xaa Leu
1               5                   10

<210> SEQ ID NO 86
<211> LENGTH: 10
<212> TYPE: PRT
<213> ORGANISM: Homo sapiens

<400> SEQUENCE: 86

Gln Glu Leu Glu Glu Lys Leu Asn Ile Leu
1               5                   10

<210> SEQ ID NO 87
<211> LENGTH: 10
<212> TYPE: PRT
<213> ORGANISM: Homo sapiens

<400> SEQUENCE: 87

Gln Glu Leu Glu Glu Lys Leu Asn Met Leu
1               5                   10

<210> SEQ ID NO 88
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Val or Ala

<400> SEQUENCE: 88

Arg Glu Xaa Leu Glu Leu Asp Ser Ile
1               5

<210> SEQ ID NO 89
<211> LENGTH: 9
<212> TYPE: PRT
<213> ORGANISM: Homo sapiens

<400> SEQUENCE: 89

Arg Glu Val Leu Glu Leu Asp Ser Ile
1               5

<210> SEQ ID NO 90
<211> LENGTH: 9
<212> TYPE: PRT
<213> ORGANISM: Homo sapiens

<400> SEQUENCE: 90

Arg Glu Ala Leu Glu Leu Asp Ser Ile
1               5

<210> SEQ ID NO 91
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
```

<223> OTHER INFORMATION: Xaa is Arg or Gln

<400> SEQUENCE: 91

Xaa Leu Ala Pro Thr Leu Ser Gln Leu
1               5

<210> SEQ ID NO 92
<211> LENGTH: 9
<212> TYPE: PRT
<213> ORGANISM: Homo sapiens

<400> SEQUENCE: 92

Arg Leu Ala Pro Thr Leu Ser Gln Leu
1               5

<210> SEQ ID NO 93
<211> LENGTH: 9
<212> TYPE: PRT
<213> ORGANISM: Homo sapiens

<400> SEQUENCE: 93

Gln Leu Ala Pro Thr Leu Ser Gln Leu
1               5

<210> SEQ ID NO 94
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Asp or Asn

<400> SEQUENCE: 94

Gln Glu Phe Ile Xaa Asn Pro Lys Trp
1               5

<210> SEQ ID NO 95
<211> LENGTH: 9
<212> TYPE: PRT
<213> ORGANISM: Homo sapiens

<400> SEQUENCE: 95

Gln Glu Phe Ile Asp Asn Pro Lys Trp
1               5

<210> SEQ ID NO 96
<211> LENGTH: 9
<212> TYPE: PRT
<213> ORGANISM: Homo sapiens

<400> SEQUENCE: 96

Gln Glu Phe Ile Asn Asn Pro Lys Trp
1               5

<210> SEQ ID NO 97
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Gly or Ala

<400> SEQUENCE: 97

Ala Glu Glu Leu Xaa Gly Pro Val His Ala Leu

-continued

```
1               5                   10

<210> SEQ ID NO 98
<211> LENGTH: 11
<212> TYPE: PRT
<213> ORGANISM: Homo sapiens

<400> SEQUENCE: 98

Ala Glu Glu Leu Gly Gly Pro Val His Ala Leu
1               5                   10

<210> SEQ ID NO 99
<211> LENGTH: 11
<212> TYPE: PRT
<213> ORGANISM: Homo sapiens

<400> SEQUENCE: 99

Ala Glu Glu Leu Ala Gly Pro Val His Ala Leu
1               5                   10

<210> SEQ ID NO 100
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Ala or Gly

<400> SEQUENCE: 100

Ser Glu Ser Glu Asp Arg Leu Val Xaa
1               5

<210> SEQ ID NO 101
<211> LENGTH: 9
<212> TYPE: PRT
<213> ORGANISM: Homo sapiens

<400> SEQUENCE: 101

Ser Glu Ser Glu Asp Arg Leu Val Ala
1               5

<210> SEQ ID NO 102
<211> LENGTH: 9
<212> TYPE: PRT
<213> ORGANISM: Homo sapiens

<400> SEQUENCE: 102

Ser Glu Ser Glu Asp Arg Leu Val Gly
1               5

<210> SEQ ID NO 103
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Leu or Phe

<400> SEQUENCE: 103

Ile Leu Ser Glu Val Glu Arg Asn Xaa
1               5

<210> SEQ ID NO 104
<211> LENGTH: 9
```

```
<212> TYPE: PRT
<213> ORGANISM: Homo sapiens

<400> SEQUENCE: 104

Ile Leu Ser Glu Val Glu Arg Asn Leu
1               5

<210> SEQ ID NO 105
<211> LENGTH: 9
<212> TYPE: PRT
<213> ORGANISM: Homo sapiens

<400> SEQUENCE: 105

Ile Leu Ser Glu Val Glu Arg Asn Phe
1               5

<210> SEQ ID NO 106
<211> LENGTH: 13
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is Ile or Val

<400> SEQUENCE: 106

Glu Glu Asn Gly Arg Lys Glu Ile Asp Xaa Lys Lys Tyr
1               5                   10

<210> SEQ ID NO 107
<211> LENGTH: 13
<212> TYPE: PRT
<213> ORGANISM: Homo sapiens

<400> SEQUENCE: 107

Glu Glu Asn Gly Arg Lys Glu Ile Asp Ile Lys Lys Tyr
1               5                   10

<210> SEQ ID NO 108
<211> LENGTH: 13
<212> TYPE: PRT
<213> ORGANISM: Homo sapiens

<400> SEQUENCE: 108

Glu Glu Asn Gly Arg Lys Glu Ile Asp Val Lys Lys Tyr
1               5                   10

<210> SEQ ID NO 109
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Arg or Lys

<400> SEQUENCE: 109

Gln Glu Glu Gln Thr Xaa Val Ala Leu
1               5

<210> SEQ ID NO 110
<211> LENGTH: 9
<212> TYPE: PRT
<213> ORGANISM: Homo sapiens

<400> SEQUENCE: 110
```

```
Gln Glu Glu Gln Thr Arg Val Ala Leu
1               5
```

<210> SEQ ID NO 111
<211> LENGTH: 9
<212> TYPE: PRT
<213> ORGANISM: Homo sapiens

<400> SEQUENCE: 111

```
Gln Glu Glu Gln Thr Lys Val Ala Leu
1               5
```

<210> SEQ ID NO 112
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ile or Ser

<400> SEQUENCE: 112

```
Xaa Leu Ala Pro Cys Lys Leu Glu Thr Val
1               5                   10
```

<210> SEQ ID NO 113
<211> LENGTH: 10
<212> TYPE: PRT
<213> ORGANISM: Homo sapiens

<400> SEQUENCE: 113

```
Ile Leu Ala Pro Cys Lys Leu Glu Thr Val
1               5                   10
```

<210> SEQ ID NO 114
<211> LENGTH: 10
<212> TYPE: PRT
<213> ORGANISM: Homo sapiens

<400> SEQUENCE: 114

```
Ser Leu Ala Pro Cys Lys Leu Glu Thr Val
1               5                   10
```

<210> SEQ ID NO 115
<211> LENGTH: 11
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Thr or Ile

<400> SEQUENCE: 115

```
Arg Ser Val Asp Val Thr Asn Xaa Thr Phe Leu
1               5                   10
```

<210> SEQ ID NO 116
<211> LENGTH: 11
<212> TYPE: PRT
<213> ORGANISM: Homo sapiens

<400> SEQUENCE: 116

```
Arg Ser Val Asp Val Thr Asn Thr Thr Phe Leu
1               5                   10
```

<210> SEQ ID NO 117

```
<211> LENGTH: 11
<212> TYPE: PRT
<213> ORGANISM: Homo sapiens

<400> SEQUENCE: 117

Arg Ser Val Asp Val Thr Asn Ile Thr Phe Leu
1               5                   10

<210> SEQ ID NO 118
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Ala or Thr

<400> SEQUENCE: 118

Ala Glu Val Glu His Val Val Asn Xaa
1               5

<210> SEQ ID NO 119
<211> LENGTH: 9
<212> TYPE: PRT
<213> ORGANISM: Homo sapiens

<400> SEQUENCE: 119

Ala Glu Val Glu His Val Val Asn Ala
1               5

<210> SEQ ID NO 120
<211> LENGTH: 9
<212> TYPE: PRT
<213> ORGANISM: Homo sapiens

<400> SEQUENCE: 120

Ala Glu Val Glu His Val Val Asn Thr
1               5

<210> SEQ ID NO 121
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Ala or Ile

<400> SEQUENCE: 121

Lys Glu Ile Xaa Lys Thr Val Leu Ile
1               5

<210> SEQ ID NO 122
<211> LENGTH: 9
<212> TYPE: PRT
<213> ORGANISM: Homo sapiens

<400> SEQUENCE: 122

Lys Glu Ile Ala Lys Thr Val Leu Ile
1               5

<210> SEQ ID NO 123
<211> LENGTH: 9
<212> TYPE: PRT
<213> ORGANISM: Homo sapiens

<400> SEQUENCE: 123
```

```
Lys Glu Ile Thr Lys Thr Val Leu Ile
1               5

<210> SEQ ID NO 124
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Leu or Ile

<400> SEQUENCE: 124

Lys Xaa Arg Gly Val Ile Asn Gln Leu
1               5

<210> SEQ ID NO 125
<211> LENGTH: 9
<212> TYPE: PRT
<213> ORGANISM: Homo sapiens

<400> SEQUENCE: 125

Lys Leu Arg Gly Val Ile Asn Gln Leu
1               5

<210> SEQ ID NO 126
<211> LENGTH: 9
<212> TYPE: PRT
<213> ORGANISM: Homo sapiens

<400> SEQUENCE: 126

Lys Ile Arg Gly Val Ile Asn Gln Leu
1               5

<210> SEQ ID NO 127
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Glu or Gln

<400> SEQUENCE: 127

Met Leu Arg Ser Xaa Leu Leu Leu
1               5

<210> SEQ ID NO 128
<211> LENGTH: 8
<212> TYPE: PRT
<213> ORGANISM: Homo sapiens

<400> SEQUENCE: 128

Met Leu Arg Ser Glu Leu Leu Leu
1               5

<210> SEQ ID NO 129
<211> LENGTH: 8
<212> TYPE: PRT
<213> ORGANISM: Homo sapiens

<400> SEQUENCE: 129

Met Leu Arg Ser Gln Leu Leu Leu
1               5
```

```
<210> SEQ ID NO 130
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Gln or Glu

<400> SEQUENCE: 130

Arg Xaa Pro Asp Leu Val Leu Arg Leu
1               5

<210> SEQ ID NO 131
<211> LENGTH: 9
<212> TYPE: PRT
<213> ORGANISM: Homo sapiens

<400> SEQUENCE: 131

Arg Gln Pro Asp Leu Val Leu Arg Leu
1               5

<210> SEQ ID NO 132
<211> LENGTH: 9
<212> TYPE: PRT
<213> ORGANISM: Homo sapiens

<400> SEQUENCE: 132

Arg Glu Pro Asp Leu Val Leu Arg Leu
1               5

<210> SEQ ID NO 133
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Ala or Thr

<400> SEQUENCE: 133

Leu Leu Leu Ala Xaa Pro Ala Gln Ala
1               5

<210> SEQ ID NO 134
<211> LENGTH: 9
<212> TYPE: PRT
<213> ORGANISM: Homo sapiens

<400> SEQUENCE: 134

Leu Leu Leu Ala Ala Pro Ala Gln Ala
1               5

<210> SEQ ID NO 135
<211> LENGTH: 9
<212> TYPE: PRT
<213> ORGANISM: Homo sapiens

<400> SEQUENCE: 135

Leu Leu Leu Ala Thr Pro Ala Gln Ala
1               5

<210> SEQ ID NO 136
<211> LENGTH: 10
<212> TYPE: PRT
<213> ORGANISM: Homo sapiens
<220> FEATURE:
```

```
<221> NAME/KEY: MISC_FEATURE
<222> LOCATION: (1)..(1)
<223> OTHER INFORMATION: Xaa is Glu or Gln

<400> SEQUENCE: 136

Xaa Glu Thr Ala Ile Tyr Lys Gly Asp Tyr
1               5                   10

<210> SEQ ID NO 137
<211> LENGTH: 10
<212> TYPE: PRT
<213> ORGANISM: Homo sapiens

<400> SEQUENCE: 137

Glu Glu Thr Ala Ile Tyr Lys Gly Asp Tyr
1               5                   10

<210> SEQ ID NO 138
<211> LENGTH: 10
<212> TYPE: PRT
<213> ORGANISM: Homo sapiens

<400> SEQUENCE: 138

Gln Glu Thr Ala Ile Tyr Lys Gly Asp Tyr
1               5                   10

<210> SEQ ID NO 139
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Ile or Val

<400> SEQUENCE: 139

Leu Xaa Asp Thr Ser Arg His Tyr Leu
1               5

<210> SEQ ID NO 140
<211> LENGTH: 9
<212> TYPE: PRT
<213> ORGANISM: Homo sapiens

<400> SEQUENCE: 140

Leu Ile Asp Thr Ser Arg His Tyr Leu
1               5

<210> SEQ ID NO 141
<211> LENGTH: 9
<212> TYPE: PRT
<213> ORGANISM: Homo sapiens

<400> SEQUENCE: 141

Leu Val Asp Thr Ser Arg His Tyr Leu
1               5

<210> SEQ ID NO 142
<211> LENGTH: 9
<212> TYPE: PRT
<213> ORGANISM: Homo sapiens

<400> SEQUENCE: 142

Val Glu Val Pro Glu Ala His Gln Leu
1               5
```

<210> SEQ ID NO 143
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Ile or Met

<400> SEQUENCE: 143

Met Glu Ser Xaa Asn Pro His Lys Tyr
1               5

<210> SEQ ID NO 144
<211> LENGTH: 9
<212> TYPE: PRT
<213> ORGANISM: Homo sapiens

<400> SEQUENCE: 144

Met Glu Ser Ile Asn Pro His Lys Tyr
1               5

<210> SEQ ID NO 145
<211> LENGTH: 9
<212> TYPE: PRT
<213> ORGANISM: Homo sapiens

<400> SEQUENCE: 145

Met Glu Ser Met Asn Pro His Lys Tyr
1               5

<210> SEQ ID NO 146
<211> LENGTH: 10
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Ile or Asn

<400> SEQUENCE: 146

Gln Glu Leu Glu Thr Ser Xaa Lys Lys Ile
1               5                   10

<210> SEQ ID NO 147
<211> LENGTH: 10
<212> TYPE: PRT
<213> ORGANISM: Homo sapiens

<400> SEQUENCE: 147

Gln Glu Leu Glu Thr Ser Asn Lys Lys Ile
1               5                   10

<210> SEQ ID NO 148
<211> LENGTH: 10
<212> TYPE: PRT
<213> ORGANISM: Homo sapiens

<400> SEQUENCE: 148

Gln Glu Leu Glu Thr Ser Asn Lys Lys Ile
1               5                   10

<210> SEQ ID NO 149
<211> LENGTH: 10
<212> TYPE: PRT
<213> ORGANISM: Homo sapiens

```
<220> FEATURE:
<221> NAME/KEY: MISC_FEATURE
<222> LOCATION: (1)..(1)
<223> OTHER INFORMATION: Xaa is Asn or Asp

<400> SEQUENCE: 149

Xaa Glu Val Leu Ile His Ser Ser Gln Tyr
1               5                   10

<210> SEQ ID NO 150
<211> LENGTH: 10
<212> TYPE: PRT
<213> ORGANISM: Homo sapiens

<400> SEQUENCE: 150

Asn Glu Val Leu Ile His Ser Ser Gln Tyr
1               5                   10

<210> SEQ ID NO 151
<211> LENGTH: 10
<212> TYPE: PRT
<213> ORGANISM: Homo sapiens

<400> SEQUENCE: 151

Asp Glu Val Leu Ile His Ser Ser Gln Tyr
1               5                   10

<210> SEQ ID NO 152
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Gln or Lys

<400> SEQUENCE: 152

Ala Glu Leu Xaa Gly Phe His Arg Ser Phe
1               5                   10

<210> SEQ ID NO 153
<211> LENGTH: 10
<212> TYPE: PRT
<213> ORGANISM: Homo sapiens

<400> SEQUENCE: 153

Ala Glu Leu Gln Gly Phe His Arg Ser Phe
1               5                   10

<210> SEQ ID NO 154
<211> LENGTH: 10
<212> TYPE: PRT
<213> ORGANISM: Homo sapiens

<400> SEQUENCE: 154

Ala Glu Leu Lys Gly Phe His Arg Ser Phe
1               5                   10

<210> SEQ ID NO 155
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Thr or Ile
```

```
<400> SEQUENCE: 155

Xaa Leu Leu Glu Asp Gly Thr Phe Lys Val
1               5                   10

<210> SEQ ID NO 156
<211> LENGTH: 10
<212> TYPE: PRT
<213> ORGANISM: Homo sapiens

<400> SEQUENCE: 156

Thr Leu Leu Glu Asp Gly Thr Phe Lys Val
1               5                   10

<210> SEQ ID NO 157
<211> LENGTH: 10
<212> TYPE: PRT
<213> ORGANISM: Homo sapiens

<400> SEQUENCE: 157

Ile Leu Leu Glu Asp Gly Thr Phe Lys Val
1               5                   10

<210> SEQ ID NO 158
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Ile or Val

<400> SEQUENCE: 158

Val Ile Ala Glu Xaa Leu Arg Gly Val
1               5

<210> SEQ ID NO 159
<211> LENGTH: 9
<212> TYPE: PRT
<213> ORGANISM: Homo sapiens

<400> SEQUENCE: 159

Val Ile Ala Glu Ile Leu Arg Gly Val
1               5

<210> SEQ ID NO 160
<211> LENGTH: 9
<212> TYPE: PRT
<213> ORGANISM: Homo sapiens

<400> SEQUENCE: 160

Val Ile Ala Glu Val Leu Arg Gly Val
1               5

<210> SEQ ID NO 161
<211> LENGTH: 10
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Asp or Glu

<400> SEQUENCE: 161

Lys Leu Ala Glu Asn Ile Xaa Ala Gln Leu
1               5                   10
```

<210> SEQ ID NO 162
<211> LENGTH: 10
<212> TYPE: PRT
<213> ORGANISM: Homo sapiens

<400> SEQUENCE: 162

Lys Leu Ala Glu Asn Ile Asp Ala Gln Leu
1               5                   10

<210> SEQ ID NO 163
<211> LENGTH: 10
<212> TYPE: PRT
<213> ORGANISM: Homo sapiens

<400> SEQUENCE: 163

Lys Leu Ala Glu Asn Ile Glu Ala Gln Leu
1               5                   10

<210> SEQ ID NO 164
<211> LENGTH: 11
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 164

Ala Glu Asn Ile Xaa Ala Gln Leu Lys Arg Met
1               5                   10

<210> SEQ ID NO 165
<211> LENGTH: 11
<212> TYPE: PRT
<213> ORGANISM: Homo sapiens

<400> SEQUENCE: 165

Ala Glu Asn Ile Asp Ala Gln Leu Lys Arg Met
1               5                   10

<210> SEQ ID NO 166
<211> LENGTH: 11
<212> TYPE: PRT
<213> ORGANISM: Homo sapiens

<400> SEQUENCE: 166

Ala Glu Asn Ile Glu Ala Gln Leu Lys Arg Met
1               5                   10

<210> SEQ ID NO 167
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ala or Thr

<400> SEQUENCE: 167

Phe Leu Gln Ala Lys Gln Ile Xaa Leu
1               5

<210> SEQ ID NO 168
<211> LENGTH: 9
<212> TYPE: PRT
<213> ORGANISM: Homo sapiens -continued

```
<400> SEQUENCE: 168

Phe Leu Gln Ala Lys Gln Ile Ala Leu
1               5

<210> SEQ ID NO 169
<211> LENGTH: 9
<212> TYPE: PRT
<213> ORGANISM: Homo sapiens

<400> SEQUENCE: 169

Phe Leu Gln Ala Lys Gln Ile Thr Leu
1               5

<210> SEQ ID NO 170
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Thr, Ile or Arg

<400> SEQUENCE: 170

Asp Glu Ile Val Cys Xaa Gln His Trp
1               5

<210> SEQ ID NO 171
<211> LENGTH: 9
<212> TYPE: PRT
<213> ORGANISM: Homo sapiens

<400> SEQUENCE: 171

Asp Glu Ile Val Cys Thr Gln His Trp
1               5

<210> SEQ ID NO 172
<211> LENGTH: 9
<212> TYPE: PRT
<213> ORGANISM: Homo sapiens

<400> SEQUENCE: 172

Asp Glu Ile Val Cys Ile Gln His Trp
1               5

<210> SEQ ID NO 173
<211> LENGTH: 9
<212> TYPE: PRT
<213> ORGANISM: Homo sapiens

<400> SEQUENCE: 173

Asp Glu Ile Val Cys Arg Gln His Trp
1               5

<210> SEQ ID NO 174
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Phe or Cys

<400> SEQUENCE: 174

Tyr Thr Trp Glu Glu Val Xaa Arg Val
1               5
```

<210> SEQ ID NO 175
<211> LENGTH: 9
<212> TYPE: PRT
<213> ORGANISM: Homo sapiens

<400> SEQUENCE: 175

Tyr Thr Trp Glu Glu Val Phe Arg Val
1               5

<210> SEQ ID NO 176
<211> LENGTH: 9
<212> TYPE: PRT
<213> ORGANISM: Homo sapiens

<400> SEQUENCE: 176

Tyr Thr Trp Glu Glu Val Cys Arg Val
1               5

<210> SEQ ID NO 177
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Leu, Met or Val

<400> SEQUENCE: 177

Lys Thr Asp Lys Thr Leu Val Xaa Leu
1               5

<210> SEQ ID NO 178
<211> LENGTH: 9
<212> TYPE: PRT
<213> ORGANISM: Homo sapiens

<400> SEQUENCE: 178

Lys Thr Asp Lys Thr Leu Val Leu Leu
1               5

<210> SEQ ID NO 179
<211> LENGTH: 9
<212> TYPE: PRT
<213> ORGANISM: Homo sapiens

<400> SEQUENCE: 179

Lys Thr Asp Lys Thr Leu Val Met Leu
1               5

<210> SEQ ID NO 180
<211> LENGTH: 9
<212> TYPE: PRT
<213> ORGANISM: Homo sapiens

<400> SEQUENCE: 180

Lys Thr Asp Lys Thr Leu Val Val Leu
1               5

<210> SEQ ID NO 181
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)

```
<223> OTHER INFORMATION: Xaa is Ala or Pro

<400> SEQUENCE: 181

Ser Gln Val Gln Val Pro Leu Glu Xaa
1               5

<210> SEQ ID NO 182
<211> LENGTH: 9
<212> TYPE: PRT
<213> ORGANISM: Homo sapiens

<400> SEQUENCE: 182

Ser Gln Val Gln Val Pro Leu Glu Ala
1               5

<210> SEQ ID NO 183
<211> LENGTH: 9
<212> TYPE: PRT
<213> ORGANISM: Homo sapiens

<400> SEQUENCE: 183

Ser Gln Val Gln Val Pro Leu Glu Pro
1               5

<210> SEQ ID NO 184
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is His or Arg

<400> SEQUENCE: 184

Glu Glu Tyr Glu Glu Leu Leu Xaa Tyr
1               5

<210> SEQ ID NO 185
<211> LENGTH: 9
<212> TYPE: PRT
<213> ORGANISM: Homo sapiens

<400> SEQUENCE: 185

Glu Glu Tyr Glu Glu Leu Leu His Tyr
1               5

<210> SEQ ID NO 186
<211> LENGTH: 9
<212> TYPE: PRT
<213> ORGANISM: Homo sapiens

<400> SEQUENCE: 186

Glu Glu Tyr Glu Glu Leu Leu Arg Tyr
1               5

<210> SEQ ID NO 187
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Asp ou Glu

<400> SEQUENCE: 187

Thr Glu Gly Xaa Ala Leu Asp Ala Leu Gly Leu Lys Arg Tyr
```

```
1               5                    10
```

<210> SEQ ID NO 188
<211> LENGTH: 14
<212> TYPE: PRT
<213> ORGANISM: Homo sapiens

<400> SEQUENCE: 188

```
Thr Glu Gly Asp Ala Leu Asp Ala Leu Gly Leu Lys Arg Tyr
1               5                    10
```

<210> SEQ ID NO 189
<211> LENGTH: 14
<212> TYPE: PRT
<213> ORGANISM: Homo sapiens

<400> SEQUENCE: 189

```
Thr Glu Gly Glu Ala Leu Asp Ala Leu Gly Leu Lys Arg Tyr
1               5                    10
```

<210> SEQ ID NO 190
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Gln or His

<400> SEQUENCE: 190

```
Gly Xaa Tyr Thr Asp Leu Leu Arg Leu
1               5
```

<210> SEQ ID NO 191
<211> LENGTH: 9
<212> TYPE: PRT
<213> ORGANISM: Homo sapiens

<400> SEQUENCE: 191

```
Gly Gln Tyr Thr Asp Leu Leu Arg Leu
1               5
```

<210> SEQ ID NO 192
<211> LENGTH: 9
<212> TYPE: PRT
<213> ORGANISM: Homo sapiens

<400> SEQUENCE: 192

```
Gly His Tyr Thr Asp Leu Leu Arg Leu
1               5
```

<210> SEQ ID NO 193
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Glu or Asp

<400> SEQUENCE: 193

```
Gly Xaa Tyr Phe Ala Ile Lys Ala Leu
1               5
```

<210> SEQ ID NO 194
<211> LENGTH: 9

```
<212> TYPE: PRT
<213> ORGANISM: Homo sapiens

<400> SEQUENCE: 194

Gly Glu Tyr Phe Ala Ile Lys Ala Leu
1               5

<210> SEQ ID NO 195
<211> LENGTH: 9
<212> TYPE: PRT
<213> ORGANISM: Homo sapiens

<400> SEQUENCE: 195

Gly Asp Tyr Phe Ala Ile Lys Ala Leu
1               5

<210> SEQ ID NO 196
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Glu or Lys

<400> SEQUENCE: 196

Ile Xaa Asp Arg Gln Tyr Lys Asp Tyr
1               5

<210> SEQ ID NO 197
<211> LENGTH: 9
<212> TYPE: PRT
<213> ORGANISM: Homo sapiens

<400> SEQUENCE: 197

Ile Glu Asp Arg Gln Tyr Lys Asp Tyr
1               5

<210> SEQ ID NO 198
<211> LENGTH: 9
<212> TYPE: PRT
<213> ORGANISM: Homo sapiens

<400> SEQUENCE: 198

Ile Lys Asp Arg Gln Tyr Lys Asp Tyr
1               5

<210> SEQ ID NO 199
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is His or Arg

<400> SEQUENCE: 199

Ala Glu Asn Asp Phe Val Xaa Arg Ile
1               5

<210> SEQ ID NO 200
<211> LENGTH: 9
<212> TYPE: PRT
<213> ORGANISM: Homo sapiens

<400> SEQUENCE: 200
```

Ala Glu Asn Asp Phe Val His Arg Ile
1               5

<210> SEQ ID NO 201
<211> LENGTH: 9
<212> TYPE: PRT
<213> ORGANISM: Homo sapiens

<400> SEQUENCE: 201

Ala Glu Asn Asp Phe Val Arg Arg Ile
1               5

<210> SEQ ID NO 202
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Leu or Val

<400> SEQUENCE: 202

Arg Xaa Leu Gln Glu Gln His Gln Leu
1               5

<210> SEQ ID NO 203
<211> LENGTH: 9
<212> TYPE: PRT
<213> ORGANISM: Homo sapiens

<400> SEQUENCE: 203

Arg Leu Leu Gln Glu Gln His Gln Leu
1               5

<210> SEQ ID NO 204
<211> LENGTH: 9
<212> TYPE: PRT
<213> ORGANISM: Homo sapiens

<400> SEQUENCE: 204

Arg Val Leu Gln Glu Gln His Gln Leu
1               5

<210> SEQ ID NO 205
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Arg or Leu

<400> SEQUENCE: 205

Xaa Leu Gln Glu Glu Leu Glu Lys Leu
1               5

<210> SEQ ID NO 206
<211> LENGTH: 9
<212> TYPE: PRT
<213> ORGANISM: Homo sapiens

<400> SEQUENCE: 206

Arg Leu Gln Glu Glu Leu Glu Lys Leu
1               5

<210> SEQ ID NO 207

```
<211> LENGTH: 9
<212> TYPE: PRT
<213> ORGANISM: Homo sapiens

<400> SEQUENCE: 207

Leu Leu Gln Glu Glu Leu Glu Lys Leu
1               5

<210> SEQ ID NO 208
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Leu or Ser

<400> SEQUENCE: 208

Gly Xaa Ser Pro Leu Leu Gln Lys Ile
1               5

<210> SEQ ID NO 209
<211> LENGTH: 9
<212> TYPE: PRT
<213> ORGANISM: Homo sapiens

<400> SEQUENCE: 209

Gly Leu Ser Pro Leu Leu Gln Lys Ile
1               5

<210> SEQ ID NO 210
<211> LENGTH: 9
<212> TYPE: PRT
<213> ORGANISM: Homo sapiens

<400> SEQUENCE: 210

Gly Ser Ser Pro Leu Leu Gln Lys Ile
1               5

<210> SEQ ID NO 211
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Gln or Arg

<400> SEQUENCE: 211

Glu Xaa Gln Leu Leu Tyr Arg Ser Trp
1               5

<210> SEQ ID NO 212
<211> LENGTH: 9
<212> TYPE: PRT
<213> ORGANISM: Homo sapiens

<400> SEQUENCE: 212

Glu Gln Gln Leu Leu Tyr Arg Ser Trp
1               5

<210> SEQ ID NO 213
<211> LENGTH: 9
<212> TYPE: PRT
<213> ORGANISM: Homo sapiens

<400> SEQUENCE: 213
```

Glu Arg Gln Leu Leu Tyr Arg Ser Trp
1               5

<210> SEQ ID NO 214
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Asp or Gly

<400> SEQUENCE: 214

Thr Glu Val Xaa Glu Ala Gly Ser Gln Leu
1               5                   10

<210> SEQ ID NO 215
<211> LENGTH: 10
<212> TYPE: PRT
<213> ORGANISM: Homo sapiens

<400> SEQUENCE: 215

Thr Glu Val Asp Glu Ala Gly Ser Gln Leu
1               5                   10

<210> SEQ ID NO 216
<211> LENGTH: 10
<212> TYPE: PRT
<213> ORGANISM: Homo sapiens

<400> SEQUENCE: 216

Thr Glu Val Gly Glu Ala Gly Ser Gln Leu
1               5                   10

<210> SEQ ID NO 217
<211> LENGTH: 11
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Gln or Glu

<400> SEQUENCE: 217

Xaa Glu Ala Pro Glu Ser Ala Thr Val Ile Phe
1               5                   10

<210> SEQ ID NO 218
<211> LENGTH: 11
<212> TYPE: PRT
<213> ORGANISM: Homo sapiens

<400> SEQUENCE: 218

Gln Glu Ala Pro Glu Ser Ala Thr Val Ile Phe
1               5                   10

<210> SEQ ID NO 219
<211> LENGTH: 11
<212> TYPE: PRT
<213> ORGANISM: Homo sapiens

<400> SEQUENCE: 219

Glu Glu Ala Pro Glu Ser Ala Thr Val Ile Phe
1               5                   10

```
<210> SEQ ID NO 220
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Glu or Asp

<400> SEQUENCE: 220

Thr Glu Thr Gln Xaa Lys Asn Thr Leu
1               5

<210> SEQ ID NO 221
<211> LENGTH: 9
<212> TYPE: PRT
<213> ORGANISM: Homo sapiens

<400> SEQUENCE: 221

Thr Glu Thr Gln Glu Lys Asn Thr Leu
1               5

<210> SEQ ID NO 222
<211> LENGTH: 9
<212> TYPE: PRT
<213> ORGANISM: Homo sapiens

<400> SEQUENCE: 222

Thr Glu Thr Gln Asp Lys Asn Thr Leu
1               5

<210> SEQ ID NO 223
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Val or Ile

<400> SEQUENCE: 223

Ala Glu Xaa Arg Ala Glu Asn Leu
1               5

<210> SEQ ID NO 224
<211> LENGTH: 8
<212> TYPE: PRT
<213> ORGANISM: Homo sapiens

<400> SEQUENCE: 224

Ala Glu Val Arg Ala Glu Asn Leu
1               5

<210> SEQ ID NO 225
<211> LENGTH: 8
<212> TYPE: PRT
<213> ORGANISM: Homo sapiens

<400> SEQUENCE: 225

Ala Glu Ile Arg Ala Glu Asn Leu
1               5

<210> SEQ ID NO 226
<211> LENGTH: 9
<212> TYPE: PRT
<213> ORGANISM: Homo sapiens
<220> FEATURE:
```

```
<221> NAME/KEY: MISC_FEATURE
<222> LOCATION: (8)..(8)
<223> OTHER INFORMATION: Xaa is Ile or Thr

<400> SEQUENCE: 226

Leu Leu Trp Ala Gly Pro Val Xaa Ala
1               5

<210> SEQ ID NO 227
<211> LENGTH: 9
<212> TYPE: PRT
<213> ORGANISM: Homo sapiens

<400> SEQUENCE: 227

Leu Leu Trp Ala Gly Pro Val Ile Ala
1               5

<210> SEQ ID NO 228
<211> LENGTH: 9
<212> TYPE: PRT
<213> ORGANISM: Homo sapiens

<400> SEQUENCE: 228

Leu Leu Trp Ala Gly Pro Val Thr Ala
1               5

<210> SEQ ID NO 229
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Asn or Asp

<400> SEQUENCE: 229

Lys Glu Xaa Gln Glu Ala Glu Lys Leu
1               5

<210> SEQ ID NO 230
<211> LENGTH: 9
<212> TYPE: PRT
<213> ORGANISM: Homo sapiens

<400> SEQUENCE: 230

Lys Glu Asn Gln Glu Ala Glu Lys Leu
1               5

<210> SEQ ID NO 231
<211> LENGTH: 9
<212> TYPE: PRT
<213> ORGANISM: Homo sapiens

<400> SEQUENCE: 231

Lys Glu Asp Gln Glu Ala Glu Lys Leu
1               5

<210> SEQ ID NO 232
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Gln or Arg

<400> SEQUENCE: 232
```

```
Xaa Glu Tyr Gln Val Lys Leu Gln Ala
1               5

<210> SEQ ID NO 233
<211> LENGTH: 9
<212> TYPE: PRT
<213> ORGANISM: Homo sapiens

<400> SEQUENCE: 233

Gln Glu Tyr Gln Val Lys Leu Gln Ala
1               5

<210> SEQ ID NO 234
<211> LENGTH: 10
<212> TYPE: PRT
<213> ORGANISM: Homo sapiens

<400> SEQUENCE: 234

Gln Arg Glu Tyr Gln Val Lys Leu Gln Ala
1               5                   10

<210> SEQ ID NO 235
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Leu, Met or Val

<400> SEQUENCE: 235

Xaa Glu Ala Asp Leu Pro Arg Ser Trp
1               5

<210> SEQ ID NO 236
<211> LENGTH: 9
<212> TYPE: PRT
<213> ORGANISM: Homo sapiens

<400> SEQUENCE: 236

Leu Glu Ala Asp Leu Pro Arg Ser Trp
1               5

<210> SEQ ID NO 237
<211> LENGTH: 9
<212> TYPE: PRT
<213> ORGANISM: Homo sapiens

<400> SEQUENCE: 237

Met Glu Ala Asp Leu Pro Arg Ser Trp
1               5

<210> SEQ ID NO 238
<211> LENGTH: 9
<212> TYPE: PRT
<213> ORGANISM: Homo sapiens

<400> SEQUENCE: 238

Val Glu Ala Asp Leu Pro Arg Ser Trp
1               5

<210> SEQ ID NO 239
<211> LENGTH: 9
<212> TYPE: PRT
<213> ORGANISM: Homo sapiens
```

```
<220> FEATURE:
<221> NAME/KEY: MISC_FEATURE
<222> LOCATION: (5)..(5)
<223> OTHER INFORMATION: Xaa is Gly or Glu

<400> SEQUENCE: 239

Ile Glu Ala Thr Xaa Phe Asp Arg Leu
1               5

<210> SEQ ID NO 240
<211> LENGTH: 9
<212> TYPE: PRT
<213> ORGANISM: Homo sapiens

<400> SEQUENCE: 240

Ile Glu Ala Thr Gly Phe Asp Arg Leu
1               5

<210> SEQ ID NO 241
<211> LENGTH: 9
<212> TYPE: PRT
<213> ORGANISM: Homo sapiens

<400> SEQUENCE: 241

Ile Glu Ala Thr Glu Phe Asp Arg Leu
1               5

<210> SEQ ID NO 242
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Leu or Pro

<400> SEQUENCE: 242

Ser Xaa Asp Asp His Val Val Ala Val
1               5

<210> SEQ ID NO 243
<211> LENGTH: 9
<212> TYPE: PRT
<213> ORGANISM: Homo sapiens

<400> SEQUENCE: 243

Ser Leu Asp Asp His Val Val Ala Val
1               5

<210> SEQ ID NO 244
<211> LENGTH: 9
<212> TYPE: PRT
<213> ORGANISM: Homo sapiens

<400> SEQUENCE: 244

Ser Pro Asp Asp His Val Val Ala Val
1               5

<210> SEQ ID NO 245
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is His or Arg
```

```
<400> SEQUENCE: 245

Gln Glu Pro Phe Val Phe Xaa Glu Phe
1               5

<210> SEQ ID NO 246
<211> LENGTH: 9
<212> TYPE: PRT
<213> ORGANISM: Homo sapiens

<400> SEQUENCE: 246

Gln Glu Pro Phe Val Phe His Glu Phe
1               5

<210> SEQ ID NO 247
<211> LENGTH: 9
<212> TYPE: PRT
<213> ORGANISM: Homo sapiens

<400> SEQUENCE: 247

Gln Glu Pro Phe Val Phe Arg Glu Phe
1               5

<210> SEQ ID NO 248
<211> LENGTH: 10
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 248

Lys Glu Phe Glu Asp Xaa Ile Ile Asn Trp
1               5                   10

<210> SEQ ID NO 249
<211> LENGTH: 10
<212> TYPE: PRT
<213> ORGANISM: Homo sapiens

<400> SEQUENCE: 249

Lys Glu Phe Glu Asp Gly Ile Ile Asn Trp
1               5                   10

<210> SEQ ID NO 250
<211> LENGTH: 10
<212> TYPE: PRT
<213> ORGANISM: Homo sapiens

<400> SEQUENCE: 250

Lys Glu Phe Glu Asp Asp Ile Ile Asn Trp
1               5                   10

<210> SEQ ID NO 251
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Asn or Lys

<400> SEQUENCE: 251

Val Leu Gln Xaa Val Ala Phe Ser Val
1               5
```

```
<210> SEQ ID NO 252
<211> LENGTH: 9
<212> TYPE: PRT
<213> ORGANISM: Homo sapiens

<400> SEQUENCE: 252

Val Leu Gln Asn Val Ala Phe Ser Val
1               5

<210> SEQ ID NO 253
<211> LENGTH: 9
<212> TYPE: PRT
<213> ORGANISM: Homo sapiens

<400> SEQUENCE: 253

Val Leu Gln Lys Val Ala Phe Ser Val
1               5

<210> SEQ ID NO 254
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Ser or Pro

<400> SEQUENCE: 254

Phe Leu Xaa Ser Ala Asn Glu His Leu
1               5

<210> SEQ ID NO 255
<211> LENGTH: 9
<212> TYPE: PRT
<213> ORGANISM: Homo sapiens

<400> SEQUENCE: 255

Phe Leu Ser Ser Ala Asn Glu His Leu
1               5

<210> SEQ ID NO 256
<211> LENGTH: 9
<212> TYPE: PRT
<213> ORGANISM: Homo sapiens

<400> SEQUENCE: 256

Phe Leu Pro Ser Ala Asn Glu His Leu
1               5

<210> SEQ ID NO 257
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Val or Ala

<400> SEQUENCE: 257

Ser Leu Gln Glu Lys Xaa Ala Lys Ala
1               5

<210> SEQ ID NO 258
<211> LENGTH: 9
<212> TYPE: PRT
<213> ORGANISM: Homo sapiens
```

```
<400> SEQUENCE: 258

Ser Leu Gln Glu Lys Val Ala Lys Ala
1               5

<210> SEQ ID NO 259
<211> LENGTH: 9
<212> TYPE: PRT
<213> ORGANISM: Homo sapiens

<400> SEQUENCE: 259

Ser Leu Gln Glu Lys Ala Ala Lys Ala
1               5

<210> SEQ ID NO 260
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Iso or Met

<400> SEQUENCE: 260

Thr Leu Ser Pro Glu Xaa Ile Thr Val
1               5

<210> SEQ ID NO 261
<211> LENGTH: 9
<212> TYPE: PRT
<213> ORGANISM: Homo sapiens

<400> SEQUENCE: 261

Thr Leu Ser Pro Glu Ile Ile Thr Val
1               5

<210> SEQ ID NO 262
<211> LENGTH: 9
<212> TYPE: PRT
<213> ORGANISM: Homo sapiens

<400> SEQUENCE: 262

Thr Leu Ser Pro Glu Met Ile Thr Val
1               5

<210> SEQ ID NO 263
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Ile or Val

<400> SEQUENCE: 263

Ala Glu Xaa Leu Arg Gly Val Arg Leu
1               5

<210> SEQ ID NO 264
<211> LENGTH: 9
<212> TYPE: PRT
<213> ORGANISM: Homo sapiens

<400> SEQUENCE: 264

Ala Glu Ile Leu Arg Gly Val Arg Leu
1               5
```

-continued

```
<210> SEQ ID NO 265
<211> LENGTH: 9
<212> TYPE: PRT
<213> ORGANISM: Homo sapiens

<400> SEQUENCE: 265

Ala Glu Val Leu Arg Gly Val Arg Leu
1               5

<210> SEQ ID NO 266
<211> LENGTH: 11
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Ser or Thr

<400> SEQUENCE: 266

Cys Ile Pro Pro Asp Xaa Leu Leu Phe Pro Ala
1               5                   10

<210> SEQ ID NO 267
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Thr or Ile

<400> SEQUENCE: 267

Ala Met Leu Glu Arg Gln Phe Xaa Val
1               5

<210> SEQ ID NO 268
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is His or Arg

<400> SEQUENCE: 268

Val Leu Xaa Asp Asp Leu Leu Glu Ala
1               5

<210> SEQ ID NO 269
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Val or Met

<400> SEQUENCE: 269

Tyr Ile Gly Glu Val Leu Val Ser Xaa
1               5

<210> SEQ ID NO 270
<211> LENGTH: 9
<212> TYPE: PRT
<213> ORGANISM: Homo sapiens
<220> FEATURE:
<221> NAME/KEY: MISC_FEATURE
```

```
<222> LOCATION: (1)..(1)
<223> OTHER INFORMATION: Xaa is Arg or Pro

<400> SEQUENCE: 270

Xaa Thr Leu Asp Lys Val Leu Glu Val
1               5

<210> SEQ ID NO 271
<211> LENGTH: 10
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is His or Tyr

<400> SEQUENCE: 271

Glu Glu Lys Arg Gly Ser Leu Xaa Val Trp
1               5                   10

<210> SEQ ID NO 272
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Met or Ile

<400> SEQUENCE: 272

Met Xaa Tyr Lys Asp Ile Leu Leu Leu
1               5

<210> SEQ ID NO 273
<211> LENGTH: 9
<212> TYPE: PRT
<213> ORGANISM: Homo sapiens

<400> SEQUENCE: 273

Phe Ile Asp Ser Tyr Ile Cys Gln Val
1               5

<210> SEQ ID NO 274
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Ala or Val

<400> SEQUENCE: 274

Ala Leu Ala Pro Ala Pro Xaa Glu Val
1               5

<210> SEQ ID NO 275
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Asp or Glu

<400> SEQUENCE: 275

Phe Met Trp Asp Val Ala Glu Xaa Leu
1               5
```

<210> SEQ ID NO 276
<211> LENGTH: 11
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Asp or Glu

<400> SEQUENCE: 276

Phe Met Trp Asp Val Ala Glu Xaa Leu Lys Ala
1               5                   10

<210> SEQ ID NO 277
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ser or Leu

<400> SEQUENCE: 277

Xaa Leu Ala Val Ala Gln Asp Leu Thr
1               5

<210> SEQ ID NO 278
<211> LENGTH: 14
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is Ser or Leu

<400> SEQUENCE: 278

Val Leu Phe Arg Gly Gly Pro Arg Gly Xaa Leu Ala Val Ala
1               5                   10

<210> SEQ ID NO 279
<211> LENGTH: 10
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Ile or Met

<400> SEQUENCE: 279

Arg Thr Leu Ser Pro Glu Xaa Ile Thr Val
1               5                   10

<210> SEQ ID NO 280
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Leu or Phe

<400> SEQUENCE: 280

Arg Leu Leu Glu Ala Ile Ile Arg Xaa
1               5

<210> SEQ ID NO 281
<211> LENGTH: 11
<212> TYPE: PRT

```
<213> ORGANISM: Homo sapiens
<220> FEATURE:
<221> NAME/KEY: MISC_FEATURE
<222> LOCATION: (2)..(2)
<223> OTHER INFORMATION: Xa is Leu or Pro

<400> SEQUENCE: 281

Gly Xaa Leu Gly Gln Glu Gly Leu Val Glu Ile
1               5                   10

<210> SEQ ID NO 282
<211> LENGTH: 14
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is Leu or Ser

<400> SEQUENCE: 282

Val Leu Phe Arg Gly Gly Pro Arg Gly Xaa Leu Ala Val Ala
1               5                   10

<210> SEQ ID NO 283
<211> LENGTH: 10
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is Ala or Glu

<400> SEQUENCE: 283

Gly Leu Tyr Thr Tyr Trp Ser Ala Gly Xaa
1               5                   10

<210> SEQ ID NO 284
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Leu or Pro

<400> SEQUENCE: 284

Gln Leu Xaa Asn Ser Val Leu Thr Leu
1               5
```

MINOR HISTOCOMPATIBILITY ANTIGENS AND USES THEREOF

CROSS-REFERENCE TO RELATED APPLICATIONS

The present application is a § 371 national phase of International Application No. PCT/CA2016/050116, filed on Feb. 9, 2016, which claims the benefit of U.S. provisional application Ser. No. 62/113,727 filed on Feb. 9, 2015, which applications are incorporated herein by reference in their entireties.

TECHNICAL FIELD

The present invention generally relates to histocompatibility antigens, and more specifically to minor histocompatibility antigens (MiHAs) and use thereof, for example in immunotherapies.

BACKGROUND ART

While several treatment modalities have proven effective for cancer immunotherapy, cancer immunotherapists will undoubtedly need more than one weapon in their therapeutic armamentarium. In particular, different approaches are required for tumors with high vs. low mutation loads.[1] Solid tumors induced by carcinogens (e.g., melanoma, lung cancer) express numerous mutations that create tumor-specific antigens (TSAs) which can be targeted using two approaches: injection of ex vivo expanded tumor-infiltrating lymphocytes and administration of antibodies against checkpoint molecules.[1-3] However, TSAs are exceedingly rare on hematologic cancers (HCs), because of their very low mutation load, and alternative targets must therefore be found for immunotherapy of HCs.[1] T cells redirected to CD19 or CD20 antigen targets with engineered chimeric antigen receptors are spectacularly effective for treatment of B-cell malignancies and represent a breakthrough in cancer immunotherapy.[4,5] However, whether chimeric antigen receptors might be used for treatment of myeloid malignancies remains a matter of speculation.[6]

Major histocompatibility complex (MHC) molecules are transmembrane glycoproteins encoded by closely linked polymorphic loci located on chromosome 6 in humans. Their primary role is to bind peptides and present them to T cells. MHC molecules (HLA in humans) present thousands of peptides at the surface of human cells. These MHC-associated peptides (MAPs) are referred to as the immunopeptidome. The immunopeptidome of identical twins (AKA syngeneic individuals) is identical. By contrast, MAPs present on cells from HLA-identical non-syngeneic individuals are classified into two categories: i) monomorphic MAPs which originate from invariant genomic regions and are therefore present in all individuals with a given HLA type, and ii) polymorphic MAPs (AKA MiHAs) which are encoded by polymorphic genomic regions and are therefore present in some individuals but absent in other individuals. MiHAs are essentially genetic polymorphisms viewed from a T-cell perspective. MiHAs are typically encoded by bi-allelic loci and where each allele can be dominant (generates a MAP) or recessive (generates no MAP). Indeed, a non-synonymous single nucleotide polymorphism (ns-SNP) in a MAP-coding genomic sequence will either hinder MAP generation (recessive allele) or generate a variant MAP (dominant allele).

Another strategy that can be used for cancer immunotherapy is adoptive T-cell immunotherapy (ATCI). The term "ATCI" refers to transfusing a patient with T lymphocytes obtained from: the patient (autologous transfusion), a genetically-identical twin donor (syngeneic transfusion), or a non-identical HLA-compatible donor (allogeneic transfusion). To date, ATCI has yielded much higher cancer remission and cure rates than vaccines, and the most widely used form of cancer ATCI is allogeneic hematopoietic cell transplantation (AHCT).

The so-called graft-versus-leukemia (GVL) effect induced by allogeneic hematopoietic cell transplantation (AHCT) is due mainly to T-cell responses against host MiHAs: the GVL is abrogated or significantly reduced if the donor is an identical twin (no MiHA differences with the recipient) or if the graft is depleted of T lymphocytes. More than 400,000 individuals treated for hematological cancers owe their life to the MiHA-dependent GVL effect which represents the most striking evidence of the ability of the human immune system to eradicate neoplasia. Though the allogeneic GVT effect is being used essentially to treat patients with hematologic malignancies, preliminary evidence suggests that it may be also effective for the treatment of solid tumors. The considerable potential of MiHA-targeted cancer immunotherapy has not been properly exploited in medicine. In current medical practice, MiHA-based immunotherapy is limited to "conventional" AHCT, that is, injection of hematopoietic cells from an allogeneic HLA-matched donor. Such unselective injection of allogeneic lymphocytes is a very rudimentary form of MiHA-targeted therapy. First, it lacks specificity and is therefore highly toxic: unselected allogeneic T cells react against a multitude of host MiHAs and thereby induce graft-versus-host-disease (GVHD) in 60% of recipients. GVHD is always incapacitating and frequently lethal. Second, conventional AHCT induces only an attenuated form of GVT reaction because donor T cells are not being primed (pre-activated) against specific MiHAs expressed on cancer cells prior to injection into the patient. While primed T cells are resistant to tolerance induction, naïve T cells can be tolerized by tumor cells.

It has been demonstrated in mice models of AHCT that, by replacing unselected donor lymphocytes with CD8+ T cells primed against a single MiHA, it was possible to cure leukemia and melanoma without causing GVHD or any other untoward effect. Success depends on two key elements: selection of an immunogenic MiHA expressed on neoplastic cells, and priming of donor CD8+ T cells against the target MiHA prior to AHCT. A recent report discusses why MiHA-targeted ATCI is so effective and how translation of this approach in the clinic could have a tremendous impact on cancer immunotherapy[8].

High-avidity T cell responses capable of eradicating tumors can be generated in an allogeneic setting. In hematological malignancies, allogeneic HLA-matched hematopoietic stem cell transplantation (ASCT) provides a platform for allogeneic immunotherapy due to the induction of T cell-mediated graft-versus-tumor (GVT) immune responses. Immunotherapy in an allogeneic setting enables induction of effective T cell responses due to the fact that T cells of donor origin are not selected for low reactivity against self-antigens of the recipient. Therefore, high-affinity T cells against tumor- or recipient-specific antigens can be found in the T cell inoculum administered to the patient during or after ASCT. The main targets of the tumor-reactive T cell responses are polymorphic proteins for which donor and recipient are disparate, namely MiHAs.

However, implementation of MiHA-targeted immunotherapy in humans has been limited mainly by the paucity of molecularly defined human MiHAs. Based on the MiHAs currently known, only 33% of patients with leukemia would be eligible for MiHA-based ATCI. MiHA discovery is a difficult task because it cannot be achieved using standard genomic and proteomic methods. Indeed, i) less than 1% of SNPs generate a MiHA and ii) current mass spectrometry methods cannot detect MiHAs.

Thus, there is a need for the identification of novel MiHAs that may be used in immunotherapies.

The present description refers to a number of documents, the content of which is herein incorporated by reference in their entirety.

SUMMARY OF THE INVENTION

The present invention relates to the following items 1 to 53:

1. A Minor Histocompatibility Antigen (MiHA) peptide of 8 to 14 amino acids of the formula I $$Z^1-X^1-Z^2 \quad (I)$$

wherein
$Z^1$ is an amino terminal modifying group or is absent;
$X^1$ is a sequence comprising at least 8 contiguous residues of one of the peptide sequences set forth in Table VI and comprising the polymorphic amino acid depicted; and
$Z^2$ is a carboxy terminal modifying group or is absent;

TABLE VI

| Sequence | SEQ ID NO: | Sequence | SEQ ID NO: |
|---|---|---|---|
| SEESAVPK/ERSW | 40-42 | AELQ/KGFHRSF | 152-154 |
| SEESAVPE/KRSW | 40-42 | HLEEQIA/PKV | 4-6 |
| QELEEKLNI/ML | 85-87 | HLEEQIP/AKV | 4-6 |
| REV/ALELDSI | 88-90 | T/ILLEDGTFKV | 155-157 |
| R/QLAPTLSQL | 91-93 | I/TLLEDGTFKV | 155-157 |
| QEFID/NNPKW | 94-96 | VIAEI/VLRGV | 158-160 |
| EEIPV/ISSHY | 10-12 | AEI/VLRGVRL | 263-265 |
| EEIPV/ISSHYF | 13-15 | KLAENID/EAQL | 161-163 |
| AEELG/AGPVHAL | 97-99 | AENID/EAQLKRM | 164-166 |
| AE/AIQEKKEI | 16-18 | FLQAKQIA/TL | 167-169 |
| SESEDRLVA/G | 100-102 | DEIVCT/I/RQHW | 170-173 |
| ILSEVERNL/F | 103-105 | YTWEEVF/CRV | 174-176 |
| EENGRKEIDI/VKKY | 106-108 | KTDKTLVL/M/VL | 177-180 |
| QEN/DIQ/HNLQL | 19-23 | SQVQVPLEA/P | 181-183 |
| QEN/DIQ/HNLQL | 19-23 | EEYEELLH/RY | 184-186 |
| QEEQTR/KVAL | 109-111 | EEYEELLR/HY | 184-186 |
| I/SLAPCKLETV | 112-114 | TEGD/EALDALGLKRY | 187-189 |
| S/ILAPCKLETV | 112-114 | GQ/HYTDLLRL | 190-192 |
| RSVDVTNT/ITFL | 115-117 | EEALGLYH/QW | 55-57 |
| VEEADGN/HKQW | 24-26 | GE/DYFAIKAL | 193-195 |
| EEADGN/HKQWW | 27-29 | IE/KDRQYKDY | 196-198 |
| AEVEHVVNA/T | 118-120 | AENDFVH/RRI | 199-201 |
| KEIA/TKTVLI | 121-123 | A/SEIEQKIKEY | 7-9 |
| KL/IRGVINQL | 124-126 | S/AEIEQKIKEY | 7-9 |
| KI/LRGVINQL | 124-126 | SQA/SEIEQKI | 58-60 |
| MLRSE/QLLL | 127-129 | RL/VLQEQHQL | 202-204 |
| RQ/EPDLVLRL | 130-132 | R/LLQEELEKL | 205-207 |
| LLLAA/TPAQA | 133-135 | GL/SSPLLQKI | 208-210 |
| E/QETAIYKGDY | 136-138 | TEMEIS/PRAA | 61-63 |
| LI/VDTSRHYL | 139-141 | EQ/RQLLYRSW | 211-213 |
| EE/GRGENTSY | 30-32 | KEINEKSN/SIL | 64-66 |
| KILEKEIR/CV | 1-3 | TEVD/GEAGSQL | 214-216 |
| SESKIR/CVLL | 33-35 | Q/EEAPESATVIF | 217-219 |
| VEVPEAHQL or absent | 142 | EE/KEQSQSRW | 67-69 |
| NESNTQKTY or absent | 36 | TETQE/DKNTL | 220-222 |
| MESI/MNPHKY | 143-145 | AEV/IRAENL | 223-225 |
| QELETSI/NKKI | 146-148 | AELQS/ARLAA | 70-72 |
| N/DEVLIHSSQY | 149-151 | LLWAGPVI/TA | 226-228 |
| EEINLQR/INI | 37-39 | KEN/DQEAEKL | 229-231 |
| SLLESSRSQEL/P | 79-81 | Q/REYQVKLQA | 232-234 |
| ALSGHLETV/L | 82-84 | R/QEYQVKLQA | 232-234 |
| EESAVPE/KRSW | 43-45 | L/M/VEADLPRSW | 235-238 |
| EESAVPK/ERSW | 43-45 | QENQDPR/GRW | 73-75 |
| QE/DLIGKKEY | 46-48 | IEATG/EFDRL | 239-241 |
| EELLAVG/SKF | 49-51 | SL/PDDHVVAV | 242-244 |
| EELLAVS/GKF | 49-51 | QEPFVFH/REF | 245-247 |
| GED/GKGIKAL | 52-54. | | |

2. The MiHA peptide of item 1, wherein $X^1$ consists of any one of the peptide sequences set forth in Table VI.
3. The MiHA peptide of item 1, wherein $X^1$ is a sequence comprising at least 8 contiguous residues of one of the peptide sequences set forth in SEQ ID Nos: 1-75 and comprising the polymorphic amino acid.
4. The MiHA peptide of item 3, wherein $X^1$ consists of any one of the peptide sequences set forth in SEQ ID Nos: 1-75.
5. The MiHA peptide of any one of items 1 to 4, wherein $Z^1$ is absent.
6. The MiHA peptide of any one of items 1 to 5, wherein $Z^2$ is absent.
7. The MiHA peptide of any one of items 1 to 6, wherein said MiHA peptide consists of any one of the peptide sequences set forth in Table VI.

8. The MiHA peptide of any one of items 1 to 7, wherein said MiHA peptide consists of any one of the peptide sequences set forth in SEQ ID Nos: 1-75.
9. The MiHA peptide of item any one of items 1 to 8, wherein said MiHA derives from a locus with a minor allele frequency (MAF) of at least 0.1.
10. The MiHA peptide of item 9, wherein said MiHA derives from a locus with a minor allele frequency (MAF) of at least 0.2.
11. The MiHA peptide of any one of items 1 to 10, wherein said MiHA peptide binds to a major histocompatibility complex (MHC) class I molecule of the HLA-A*02:01 allele, and said peptide sequences are set forth in Table VII:

TABLE VII

| Sequence | SEQ ID NO: | Sequence | SEQ ID NO: |
|---|---|---|---|
| SLLESSRSQEL/P | 79-81 | T/ILLEDGTFKV | 155-157 |
| ALSGHLETV/L | 82-84 | I/TLLEDGTFKV | 155-157 |
| ILSEVERNL/F | 103-105 | VIAEI/VLRGV | 158-160 |
| I/SLAPCKLETV | 112-114 | KLAENID/EAQL | 161-163 |
| S/ILAPCKLETV | 112-114 | FLQAKQIA/TL | 167-169 |
| RSVDVTNT/ITFL | 115-117 | YTWEEVF/CRV | 174-176 |
| KL/IRGVINQL | 124-126 | KTDKTLVL/M/VL | 177-180 |
| KI/LRGVINQL | 124-126 | SQVQVPLEA/P | 181-183 |
| MLRSE/QLLL | 127-129 | GQ/HYTDLLRL | 190-192 |
| RQ/EPDLVLRL | 130-132 | SQA/SEIEQKI | 58-60 |
| LLLAA/TPAQA | 133-135 | RL/VLQEQHQL | 202-204 |
| LI/VDTSRHYL | 139-141 | R/LLQEELEKL | 205-207 |
| KILEKEIR/CV | 1-3 | GL/SSPLLQKI | 208-210 |
| HLEEQIA/PKV | 4-6 | LLWAGPVI/TA | 226-228 |
| HLEEQIA/PKV | 4-6 | SL/PDDHVVAV | 242-244. |

12. The MiHA peptide of any one of items 1 to 10, wherein said peptide binds to a major histocompatibility complex (MHC) class I molecule of the HLA-B*44:03 allele, and said peptide sequences are set forth in Table VIII:

TABLE VIII

| Sequence | SEQ ID NO: | Sequence | SEQ ID NO: |
|---|---|---|---|
| SEESAVPK/ERSW | 40-42 | EELLAVG/SKF | 49-51 |
| SEESAVPE/KRSW | 40-42 | EELLAVS/GKF | 49-51 |
| R/QLAPTLSQL | 91-93 | GED/GKGIKAL | 52-54 |
| QEFID/NNPKW | 94-96 | AELQ/KGFHRSF | 152-154 |
| EEIPV/ISSHY | 10-12 | AEI/VLRGVRL | 263-265 |
| EEIPV/ISSHYF | 13-15 | AENID/EAQLKRM | 164-166 |
| AEELG/AGPVHAL | 97-99 | DEIVCT/I/RQHW | 170-173 |
| AE/AIQEKKEI | 16-18 | EEYEELLH/RY | 184-186 |

TABLE VIII-continued

| Sequence | SEQ ID NO: | Sequence | SEQ ID NO: |
|---|---|---|---|
| SESEDRLVA/G | 100-102 | EEYEELLR/HY | 184-186 |
| EENGRKEIDI/VKKY | 106-108 | TEGD/EALDALGLKRY | 187-189 |
| QEN/DIQ/HNLQL | 19-23 | EEALGLYH/QW | 55-57 |
| QEN/DIQ/HNLQL | 19-23 | GE/DYFAIKAL | 193-195 |
| QEEQTR/KVAL | 109-111 | IE/KDRQYKDY | 196-198 |
| VEEADGN/HKQW | 24-26 | AENDFVH/RRI | 199-201 |
| EEADGN/HKQWW | 27-29 | A/SEIEQKIKEY | 7-9 |
| AEVEHVVNA/T | 118-120 | S/AEIEQKIKEY | 7-9 |
| KEIA/TKTVLI | 121-123 | TEMEIS/PRAA | 61-63 |
| E/QETAIYKGDY | 136-138 | EQ/RQLLYRSW | 211-213 |
| EE/GRGENTSY | 30-32 | KEINEKSN/SIL | 64-66 |
| SESKIR/CVLL | 33-35 | TEVD/GEAGSQL | 214-216 |
| VEVPEAHQL or absent | 142 | Q/EEAPESATVIF | 217-219 |
| NESNTQKTY or absent | 36 | EE/KEQSQSRW | 67-69 |
| MESI/MNPHKY | 143-145 | TETQE/DKNTL | 220-222 |
| QELETSI/NKKI | 146-148 | AEV/IRAENL | 223-225 |
| N/DEVLIHSSQY | 149-151 | AELQS/ARLAA | 70-72 |
| EEINLQR/INI | 37-39 | KEN/DQEAEKL | 229-231 |
| QELEEKLNI/ML | 85-87 | Q/REYQVKLQA | 232-234 |
| REV/ALELDSI | 88-90 | R/QEYQVKLQA | 232-234 |
| EESAVPE/KRSW | 43-45 | L/M/VEADLPRSW | 235-238 |
| EESAVPK/ERSW | 43-45 | QENQDPR/GRW | 73-75 |
| QE/DLIGKKEY | 46-48 | IEATG/EFDRL | 239-241 |
|  |  | QEPFVFH/REF | 245-247 |

13. A polypeptide comprising an amino acid sequence of at least one of the MiHA peptide defined in any one of items 1 to 12, wherein said polypeptide is of the following formula Ia:

$$Z^1\text{—}X^2\text{—}X^1\text{—}X^3\text{—}Z^2 \tag{Ia}$$

wherein
$Z^1$, $X^1$ and $Z^2$ are as defined in any one of items 1 to 12; and
$X^2$ and $X^3$ are each independently absent or a sequence of one or more amino acids,
wherein said polypeptide does not comprise or consist of an amino acid sequence of a native protein, and wherein processing of said polypeptide by a cell results in the loading of the MiHA peptide in the peptide-binding groove of MHC class I molecules expressed by said cell
14. A peptide combination comprising (i) at least two of the MiHA peptides defined in any one of items 1 to 12; (ii) at least one of the MiHA peptides defined in any one of items 1 to 12 and at least one additional MiHA peptide.
15. A nucleic acid encoding the MiHA peptide of any one of items 1 to 12 or the polypeptide of item 13.

16. The nucleic acid of item 15, which is present in a plasmid or a vector.

17. An isolated major histocompatibility complex (MHC) class I molecule comprising the MiHA peptide of any one of items 1 to 12 in its peptide binding groove.

18. The isolated MHC class I molecule of item 17, which is in the form of a multimer.

19. The isolated MHC class I molecule of item 18, wherein said multimer is a tetramer.

20. An isolated cell comprising the MiHA peptide of any one of items 1 to 12, the peptide combination of item 14, or the nucleic acid of item 15 or 16.

21. An isolated cell expressing at its surface major histocompatibility complex (MHC) class I molecules comprising the MiHA peptide of any one of items 1 to 12, or the peptide combination of item 14, in their peptide binding groove.

22. The cell of item 21, which is an antigen-presenting cell (APC).

23. The cell of item 22, wherein said APC is a dendritic cell.

24. A T-cell receptor (TCR) that specifically recognizes the isolated MHC class I molecule of any one of items 17-19 and/or MHC class I molecules expressed at the surface of the cell of any one of items 21-23.

25. One or more nucleic acids encoding the alpha and beta chains of the TCR of item 24.

26. The one or more nucleic acids of item 25, which are present in a plasmid or a vector.

27. An isolated $CD8^+$ T lymphocyte expressing at its cell surface the TCR of item 24.

28. The $CD8^+$ T lymphocyte of item 27, which is transfected or transduced with the one or more nucleic acids of item 25 or 26.

29. A cell population comprising at least 0.5% of $CD8^+$ T lymphocytes according to item 27 or 28.

30. A composition comprising (i) the MiHA peptide of any one of items 1 to 12; (ii) the polypeptide of item 13; (iii) the peptide combination of item 14; (iv) the nucleic acid of item 15 or 16; (iv) the MHC class I molecule of any one of items 17-19; (v) the cell of any one of 20-23; (v) the TCR of item 24; (vi) the one or more nucleic acids of item 25 or 26; the $CD8^+$ T lymphocyte of item 27 or 28; and/or (vii) the cell population of item 29.

31. The composition of item 30, further comprising a buffer, an excipient, a carrier, a diluent and/or a medium.

32. The composition of item 30 or 31, wherein said composition is a vaccine and further comprises an adjuvant.

33. The composition of any one of items 30 to 32, wherein said composition comprises the peptide combination of item 14, or one or more nucleic acids encoding the at least two MiHA peptides present in said peptide combination.

34. The composition of any one of items 30 to 33, which comprises the cell of any one of items 19-22 and the $CD8^+$ T lymphocyte of item 26 or 27.

35. A method of expanding $CD8^+$ T lymphocytes specifically recognizing one or more of the MiHA peptides defined in any one of items 1 to 12, said method comprising culturing, under conditions suitable for $CD8^+$ T lymphocyte expansion, $CD8^+$ T lymphocytes from a candidate donor that does not express said one or more MiHA peptides in the presence of cells according to any one of items 20-22.

36. A method of treating cancer, said method comprising administering to a subject in need thereof an effective amount of (i) the $CD8^+$ T lymphocytes of item 27 or 28; (ii) the cell population of item 29; and/or (iii) a composition comprising (i) or (ii).

37. The method of item 36, said method further comprising determining one or more MiHA variants expressed by said subject in need thereof, wherein the $CD8^+$ T lymphocytes specifically recognize said one or more MiHA variants presented by MHC class I molecules.

38. The method of item 37, wherein said determining comprises sequencing a nucleic acid encoding said MiHA.

39. The method of any one of items 36 to 38, wherein said $CD8^+$ T lymphocytes are ex vivo expanded CD8+ T lymphocytes prepared according to the method of item 35.

40. The method of any one of items 36 to 39, wherein said method further comprises expanding $CD8^+$ T lymphocytes according to the method of item 35.

41. The method of any one of items 36 to 40, wherein said subject in need thereof is an allogeneic stem cell transplantation (ASCT) recipient.

42. The method of any one of items 36 to 41, further comprising administering an effective amount of the MiHA peptide recognized by said $CD8^+$ T lymphocytes, and/or (ii) a cell expressing at its surface MHC class I molecules comprising the MiHA peptide defined in (i) in their peptide binding groove.

43. The method of any one of items 36 to 42, wherein said cancer is a hematologic cancer.

44. The method of item 43, wherein said hematologic cancer is leukemia.

45. An antigen presenting cell or an artificial construct mimicking an antigen-presenting cell that presents the MiHA peptide of any one of items 1 to 12 or the peptide combination of item 14.

46. An in vitro method for producing cytotoxic T lymphocytes (CTLs) comprising contacting a T lymphocyte with human class I MHC molecules loaded with the MiHA peptide of any one of items 1 to 12 or the peptide combination of item 14 expressed on the surface of a suitable antigen presenting cell or an artificial construct mimicking an antigen-presenting cell for a period of time sufficient to activate said T lymphocyte in an antigen-specific manner.

47. An activated cytotoxic T lymphocyte obtained by method of item 46.

48. A method of treating a subject with haematological cancer comprising administering to the patient an effective amount of the cytotoxic T lymphocyte of item 47.

49. A method of generating immune response against tumor cells expressing human class I MHC molecules loaded with the MiHA peptide of any one of items 1 to 12 or the peptide combination of item 14 in a subject, said method comprising administering the cytotoxic T lymphocyte of item 47.

50. An antigen presenting cell (APC) artificially loaded with one or more of the MiHA peptides defined in any one of items 1 to 12, or the peptide combination of claim 14.

51. The APC of item 49 for use as a therapeutic vaccine.

52. A method for generating an immune response in a subject comprising administering to the subject allogenic T lymphocytes and a composition comprising one or more of the MiHA peptides defined in any one of items 1 to 12, or the peptide combination of claim 14.

53. The method of any one of items 48, 49 and 52 wherein said subject has a haematological cancer selected from leukemia, lymphoma and myeloma.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawing:

FIG. 1A: Proportion of MiHAs generated by ns-SNPs with high vs. low MAFs. MAFs of ns-SNPs coding MiHAs (lighter gray bars) or reported in European-Americans (darker gray bars) were retrieved from the Exome Sequencing Project (ESP) (http://evs.gs.washington.edu/EVS/) and classified as rare (MAF<0.05) or frequent (MAF≥0.05). As for ns-SNPs in general, most MiHA-coding SNPs have a low MAF. FIG. 1B: Number of previously discovered MiHAs[24,34] ('Reported': lower, lighter gray portions of the bars) and of new frequent MiHAs identified with the proteogenomic approach described herein (upper, darker gray portions of the bars). FIG. 1C: MAFs of novel MiHA-coding SNPs in the global population (as reported in dbSNP), in European Americans (EA) (according to ESP), or in Europeans (EUR), Admixed Americans (AMR), East Asians (EAS), South Asians (SAS) and Africans (AFR) as reported in The 1000 Genomes Project (http://www.1000genomes.org; McVean et al., An integrated map of genetic variation from 1,092 human genomes, Nature 491, 56-65 (1 Nov. 2012)).

FIG. 2A: Filtering steps used in the identification of MiHAs. A total of 6,773 sequenced 8-14mer peptides had a HLA-A*02:01 or HLA-B*44:03 predicted binding affinity ($IC_{50}$) below 5,000 nM and encoded by reported ns-SNPs. MiHA that meet these 2 criteria were further validated. FIG. 2B: Validation steps and criteria applied to select lead MiHAs for clinical development.

FIG. 3A: One representative of four IFNγ ELISpot results. FIG. 3B: Cytokine (IL-2, IFNγ) production by T cells primed against WDR27-1$^L$, as assessed by intracellular cytokine staining. FIG. 3C: Mean proportion of IFNγ-producing CD8 T cells after a four-hour re-stimulation in the presence of Brefeldin A (gated on CD8 T cells). Histograms represent mean±SEM for T cells primed against individual MiHAs (n=4) or control peptides *P<0.05. FIG. 3D: IFNγ production by T cells primed against GLRX3-1$^S$ (upper panels), RASSF1-1$^S$ (middle panels) and MIIP-2$^E$ (lower panels), as assessed by intracellular cytokine staining.

FIG. 4A: All novel MiHA-coding loci are bi-allelic. For most loci, a single (dominant) allele generates a MiHA, while the other (recessive) allele does not. In a few cases, both (co-dominant) alleles generate MiHAs. Overlapping MiHAs refer to MiHAs that originate from the same ns-SNP but have different genomic start-end positions. FIG. 4B: Number of MiHAs generated per gene. Genes coding 3 or more MiHAs are depicted in a box. FIG. 4C: A polymorphic density was calculated for all MAP-coding genes by dividing the number of ns-SNPs by the length (in nucleotides) of each peptide-coding transcript. Boxplots (middle band represents the median) show the distribution of the polymorphic index for MiHA-coding genes vs. genes coding for non-polymorphic MAPs. Outliers are not shown. The Wilcoxon rank sum test was used to compare the two distributions. *P<0.01. FIG. 4D: Proportion of MiHAs derived from a single exon or from two contiguous exons (exon-exon junction). FIG. 4E: Boxplot representing the polymorphic density of MiHA-coding exons or exon-exon-junctions, determined as in FIG. 4A. Exon-exon junction regions were defined by a range of 78 nucleotides overlapping two neighboring exons. The Wilcoxon rank sum test was used to compare the two distributions. *P<0.01.

FIG. 6A: In a cohort of 13 individuals (10 HLA-A*02:01-positive and seven HLA-B*44:03-positive) used in the present study, 94 MiHAs coded by SNPs with a MAF≥0.05 were identified. The scipy Python library (http://www.scipy.org/) was used to calculate the cumulative number of MiHAs that would be expected to be discovered by studying additional individuals. Lower curve: MiHAs associated to HLA-A*02:01; upper curve: MiHAs associated to HLA-B*44:03. FIG. 6B: The percentage of donor-recipient pairs with at least one therapeutic mismatch increases as a function of the number of MiHAs considered. A 'therapeutic mismatch' was considered present when a MiHA-coding allele was found in the recipient but not in the donor. In the case of Y chromosome-derived MiHAs, a therapeutic mismatch was considered in all male-recipient: female-donor pairs. One million unrelated or related HLA-A*02:01/B*44:03-positive donor-recipient pairs were randomly selected from a virtual population of European-American individuals. MiHA haplotypes of each donor-recipient pair were generated based on the allelic frequencies reported in Exome Sequencing Project for European Americans. For each pair, the number of MiHA mismatches was determined for increasing number of MiHAs considered. Upper curve: unrelated; lower curve: related. FIG. 6C: Average number of therapeutic MiHA mismatches found in the randomly selected donor-recipient pairs described in FIG. 6B. Left darker gray bars: unrelated; right lighter gray bars: related.

DISCLOSURE OF INVENTION

Figure 1A:
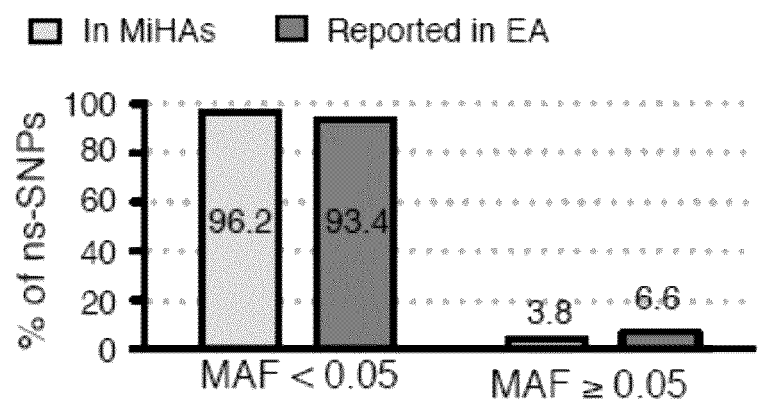
FIGS. 1A to 1C show the minor allele frequency (MAF) of MiHA-coding loci.

Terms and symbols of genetics, molecular biology, biochemistry and nucleic acid used herein follow those of standard treatises and texts in the field, e.g. Kornberg and Baker, *DNA Replication*, Second Edition (W University Science Books, 2005); Lehninger, *Biochemistry*, sixth Edition (W H Freeman & Co (Sd), New York, 2012); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like. All terms are to be understood with their typical meanings established in the relevant art.

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

The terms "subject" and "patient" are used interchangeably herein, and refer to an animal, preferably a mammal, most preferably a human, who is in the need of treatment for cancer using one or more MiHAs as described herein. These term encompass both adults and child.

MiHA Peptides and Nucleic Acids

In an aspect, the present invention provides a polypeptide (e.g., an isolated or synthetic polypeptide) comprising an amino acid sequence of a MiHA peptide, wherein said polypeptide is of the following formula Ia:

$$Z^1-X^2-X^1-X^3-Z^2 \tag{Ia}$$

wherein
$Z^1$, $X^1$ and $Z^2$ are as defined below; and
$X^2$ and $X^3$ are each independently absent or a sequence of one or more amino acids, wherein said polypeptide does not comprise or consist of an amino acid sequence of a native protein (e.g., the amino acid sequence of the native protein from which the MiHA peptide is derived), and wherein processing of said polypeptide by a cell (e.g., an antigen-presenting cell) results in the loading of the MiHA peptide of sequence $X^1$ in the peptide-binding groove of MHC class I molecules expressed by said cell.

In an embodiment, $X^2$ and/or $X^3$ are each independently a sequence of about 1 to about 5, 10, 15, 20, 25, 30, 40, 50, 100, 200, 300, 400, 500 or 1000 amino acids. In an embodiment, $X^2$ is a sequence of amino acids that is immediately amino-terminal to the sequence of $X^1$ in the native polypeptide from which the MiHA is derived (see Table II for the Ensembl gene ID corresponding to the gene from which the MiHA described herein are derived). In an embodiment, $X^3$ is a sequence of amino acids that is immediately carboxy-terminal to the sequence of $X^1$ in the native polypeptide from which the MiHA is derived (see Table II). For example, MiHA No. 1 derives from the protein Ankyrin repeat domain 13A (ANKRD13A), and thus $X^2$ and/or $X^3$ may comprises the one or more amino acids immediately amino- and/or carboxy-terminal to the sequence SLLESSRSQE<u>L</u>/P (SEQ ID NO: 79) in ANKRD13A (Ensembl gene ID No. ENSG00000076513, NCBI Reference Sequence: NP_149112.1). Thus, the sequences immediately amino- and/or carboxy-terminal to the sequences of the MiHAs described herein may be easily identified using the information available in public databases such as Ensembl, NCBI, UniProt, which may be retrieved for example using the SNP ID Nos. and/or Ensembl gene ID Nos. provided in Table II below. The entire content and information, including the full sequences of the transcripts and encoded polypeptides, corresponding to the SNP ID Nos. and Ensembl gene ID Nos. provided in Table II, are incorporated herein by reference.

In another embodiment, $X^2$ and/or $X^3$ are absent. In a further embodiment, $X^2$ and $X^3$ are both absent.

Thus, in another aspect, the present invention provides a MiHA peptide (e.g., an isolated or synthetic peptide) of about 8 to about 14 amino acids of formula I $$Z^1-X^1-Z^2 \tag{I}$$

wherein $Z^1$ is an amino terminal modifying group or is absent; $X^1$ is a sequence comprising at least 8 (preferably contiguous) residues of one of the peptide sequences of MiHA Nos. 1-93 set forth in Table I below and comprising the polymorphic amino acid (variation) depicted (underlined, e.g., for MiHA No. 1, the C-terminal residue L or P is comprised in $X^1$ and for MiHA No. 2, the C-terminal residue V or L is comprised in domain $X^1$, etc.); and $Z^2$ is a carboxy terminal modifying group or is absent. The reference to MiHA Nos. 1-93 encompasses each of the variants defined by the sequences depicted. For example, the term "MiHA No. 1" (SLLESSRSQE<u>L</u>/P, SEQ ID NO: 79) refers to SLLESSRSQE<u>L</u> (SEQ ID NO: 80) and/or SLLESSRSQE<u>P</u> (SEQ ID NO: 81).

TABLE I

Sequences of MiHAs described herein

| MiHA No. | Sequence | SEQ ID NO: | MiHA No. | Sequence | SEQ ID NO: |
|---|---|---|---|---|---|
| 1 | SLLESSRSQEL/P | 79-81 | 48 | AELQ/KGFHRSF | 152-154 |
| 2 | ALSGHLETV/L | 82-84 | 49 | HLEEQIA/PKV | 4-6 |
| 3 | QELEEKLNI/ML | 85-87 | 50 | HLEEQIP/AKV | 4-6 |
| 4 | REV/ALELDSI | 88-90 | 51 | T/ILLEDGTFKV | 155-157 |
| 5 | R/QLAPTLSQL | 91-93 | 52 | I/TLLEDGTFKV | 155-157 |
| 6 | QEFID/NNPKW | 94-96 | 53 | VIAEI/VLRGV | 158-160 |
| 7 | EEIPV/ISSHY | 10-12 | 54 | AEI/VLRGVRL | 263-265 |
| 8 | EEIPV/ISSHYF | 13-15 | 55 | KLAENID/EAQL | 161-163 |
| 9 | AEELG/AGPVHAL | 97-99 | 56 | AENID/EAQLKRM | 164-166 |
| 10 | AE/AIQEKKEI | 16-18 | 57 | FLQAKQIA/TL | 167-169 |
| 11 | SESEDRLVA/G | 100-102 | 58 | DEIVCT/I/RQHW | 170-173 |

TABLE I-continued

Sequences of MiHAs described herein

| MiHA No. | Sequence | SEQ ID NO: | MiHA No. | Sequence | SEQ ID NO: |
|---|---|---|---|---|---|
| 12 | ILSEVERNL/F | 103-105 | 59 | YTWEEVF/CRV | 174-176 |
| 13 | EENGRKEIDI/VKKY | 106-108 | 60 | KTDKTLVL/M/VL | 177-180 |
| 14 | QEN/DIQ/HNLQL | 19-23 | 61 | SQVQVPLEA/P | 181-183 |
| 15 | QEN/DIQ/HNLQL | 19-23 | 62 | EEYEELLH/RY | 184-186 |
| 16 | QEEQTR/KVAL | 109-111 | 63 | EEYEELLR/HY | 184-186 |
| 17 | I/SLAPCKLETV | 112-114 | 64 | TEGD/EALDALGLKRY | 187-189 |
| 18 | S/ILAPCKLETV | 112-114 | 65 | GQ/HYTDLLRL | 190-192 |
| 19 | RSVDVTNT/ITFL | 115-117 | 66 | EEALGLYH/QW | 55-57 |
| 20 | VEEADGN/HKQW | 24-26 | 67 | GE/DYFAIKAL | 193-195 |
| 21 | EEADGN/HKQWW | 27-29 | 68 | IE/KDRQYKDY | 196-198 |
| 22 | AEVEHVVNA/T | 118-120 | 69 | AENDFVH/RRI | 199-201 |
| 23 | KEIA/TKTVLI | 121-123 | 70 | A/SEIEQKIKEY | 7-9 |
| 24 | KL/IRGVINQL | 124-126 | 71 | S/AEIEQKIKEY | 7-9 |
| 25 | KI/LRGVINQL | 124-126 | 72 | SQA/SEIEQKI | 58-60 |
| 26 | MLRSE/QLLL | 127-129 | 73 | RL/VLQEQHQL | 202-204 |
| 27 | RQ/EPDLVLRL | 130-132 | 74 | R/LLQEELEKL | 205-207 |
| 28 | LLLAA/TPAQA | 133-135 | 75 | GL/SSPLLQKI | 208-210 |
| 29 | E/QETAIYKGDY | 136-138 | 76 | TEMEIS/PRAA | 61-63 |
| 30 | LI/VDTSRHYL | 139-141 | 77 | EQ/RQLLYRSW | 211-213 |
| 31 | EE/GRGENTSY | 30-32 | 78 | KEINEKSN/SIL | 64-66 |
| 32 | KILEKEIR/CV | 1-3 | 79 | TEVD/GEAGSQL | 214-216 |
| 33 | SESKIR/CVLL | 33-35 | 80 | Q/EEAPESATVIF | 217-219 |
| 34 | VEVPEAHQL or absent* | 142 | 81 | EE/KEQSQSRW | 67-69 |
| 35 | NESNTQKTY or absent* | 36 | 82 | TETQE/DKNTL | 220-222 |
| 36 | MESI/MNPHKY | 143-145 | 83 | AEV/IRAENL | 223-225 |
| 37 | QELETSI/NKKI | 146-148 | 84 | AELQS/ARLAA | 70-72 |
| 38 | N/DEVLIHSSQY | 149-151 | 85 | LLWAGPVI/TA | 226-228 |
| 39 | EEINLQR/INI | 37-39 | 86 | KEN/DQEAEKL | 229-231 |
| 40 | SEESAVPK/ERSW | 40-42 | 87 | Q/REYQVKLQA | 232-234 |
| 41 | SEESAVPE/KRSW | 40-42 | 88 | R/QEYQVKLQA | 232-234 |
| 42 | EESAVPE/KRSW | 43-45 | 89 | L/M/VEADLPRSW | 235-238 |
| 43 | EESAVPK/ERSW | 43-45 | 90 | QENQDPR/GRW | 73-75 |
| 44 | QE/DLIGKKEY | 46-48 | 91 | IEATG/EFDRL | 239-241 |
| 45 | EELLAVG/SKF | 49-51 | 92 | SL/PDDHVVAV | 242-244 |
| 46 | EELLAVS/GKF | 49-51 | 93 | QEPFVFH/REF | 245-247 |
| 47 | GED/GKGIKAL | 52-54 | | | |

*The genes from which these MiHAs are derived are located on chromosome Y. Accordingly, this MiHa is present in male but absent in female individuals.

In another aspect, the present invention provides a MiHA peptide of the formula I or Ia as defined above, wherein $X^1$ is a sequence comprising at least 8 amino acids of one of the peptide sequences of MiHAs 7, 8, 10, 14-15, 20-21, 32, 33, 35, 39-47, 49-50, 66, 70-71, 76, 78, 81, 84 and 90 (SEQ ID Nos: 1-75), wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 1 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 2 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 3 set forth in Table I, wherein said sequence comprises the polymorphic amino acid depicted.

In another aspect, the present invention provides a MiHA peptide of the formula I or Ia as defined above, wherein $X^1$ is a sequence of at least 8 amino acids of MiHA No. 4 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 5 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 6 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 7 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 8 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 9 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 10 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 11 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 12 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 13 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 14 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 15 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 16 set forth in Table I, wherein said sequence comprises the polymorphic amino acid depicted.

In another aspect, the present invention provides a MiHA peptide of the formula I or Ia as define (No. 119 or 120) set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 18 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 19 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 20 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 21 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 22 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 23 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 24 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 25 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 26 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 27 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 28 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 29 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 30 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 31 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 32 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 33 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 34 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 35 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 36 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 37 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 38 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 39 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 40 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 41 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 42 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 43 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 44 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 45 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 46 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 47 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 48 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 49 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 50 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 51 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 52 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 53 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 54 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 55 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 56 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 57 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 58 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 59 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 60 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 61 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 62 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 63 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 64 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 65 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 66 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 67 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 68 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 69 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 70 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 71 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 72 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 73 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 74 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 75 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 76 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 77 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 78 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 79 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 80 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 81 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 82 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 83 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 84 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No.

85 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 86 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 87 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 88 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 89 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 90 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 91 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 92 set forth in Table I, wherein said sequence comprises the polymorphic amino acid depicted.

In another aspect, the present invention provides a MiHA peptide of the formula I or Ia as defined above, wherein $X^1$ is a sequence comprising at least 8 amino acids of MiHA No. 93 set forth in Table I, wherein said sequence comprises the polymorphic amino acid depicted.

In an embodiment, the MiHA peptide is able to bind to, or to be presented by, HLA-A2 molecules (HLA-A*02:01 allele). In another aspect, the present invention provides an HLA-A2-binding MiHA peptide of 8-14 amino acids of the formula I as defined above, wherein $X^1$ is a sequence of at least 8 amino acids of any one of the MiHA Nos. 1, 2, 12, 17-19, 24-28, 30, 32, 49-53, 55, 57, 59-61, 65, 72-75, 85 and 92 set forth in Table I, wherein said sequence comprises the polymorphic amino acid depicted. In an embodiment, the HLA-A2-binding MiHA peptide comprises or consists of the sequence of MiHA Nos. 32 and 49-50.

In an embodiment, the MiHA peptide is able to bind to, or to be presented by, HLA-B44 molecules (HLA-B*44:03 allele). In another aspect, the present invention provides an HLA-B44-binding MiHA peptide of 8-14 amino acids of the formula I as defined above, wherein $X^1$ is a sequence of at least 8 amino acids of any one of the MiHA Nos. 3-11, 13-16, 20-23, 29, 31, 33-48, 54, 56, 58, 62-64, 66-71, 76-84, 86-91 and 93 set forth in Table I, wherein said sequence comprises the polymorphic amino acid depicted. In an embodiment, the HLA-B44-binding MiHA peptide comprises or consists of the sequence of MiHA Nos. 7, 8, 10, 14-15, 20-21, 33, 35, 39-47, 66, 70-71, 76, 78, 81, 84 and 90.

In an embodiment, the MiHA peptide is derived from a gene that does not exhibit ubiquitous expression. The expression "does not exhibit ubiquitous expression" is used herein to refer to a gene which, according to the data from Fagerberg et al., *Mol Cell Proteomics* 2014 13: 397-406, is not expressed with a FPKM>10 in all 27 tissues disclosed therein.

In an embodiment, the MiHA peptide derives from a locus with a minor allele frequency (MAF) of at least 0.05 as determined according to data from the dbSNP database (NCBI) and the National Heart, Lung and Blood Institute (NHLBI) Exome Sequencing Project (ESP) (as set forth in Table II). In an embodiment, the MiHA peptide derives from a locus with a MAF of at least 0.1 as determined according to data from the dbSNP database (NCBI) and/or the NHLBI Exome Sequencing Project (ESP). In an embodiment, the MiHA peptide derives from a locus with a MAF of at least 0.1 as determined according to data from the dbSNP database (NCBI) and the NHLBI Exome Sequencing Project (ESP). In an embodiment, the MiHA peptide derives from a locus with a MAF of at least 0.15 as determined according to data from the dbSNP database (NCBI) and/or the NHLBI Exome Sequencing Project (ESP). In an embodiment, the MiHA peptide derives from a locus with a MAF of at least 0.15 as determined according to data from the dbSNP database (NCBI) and the NHLBI Exome Sequencing Project (ESP). In an embodiment, the MiHA peptide derives from a locus with a MAF of at least 0.2 as determined according to data from the dbSNP database (NCBI) and/or the NHLBI Exome Sequencing Project (ESP). In an embodiment, the MiHA peptide derives from a locus with a MAF of at least 0.2 as determined according to data from the dbSNP database (NCBI) and the NHLBI Exome Sequencing Project (ESP). In an embodiment, the MiHA peptide derives from a locus with a MAF of at least 0.25 as determined according to data from the dbSNP database (NCBI) and/or the NHLBI Exome Sequencing Project (ESP). In an embodiment, the MiHA peptide derives from a locus with a MAF of at least 0.25 as determined according to data from the dbSNP database (NCBI) and the NHLBI Exome Sequencing Project (ESP). In an embodiment, the MiHA peptide derives from a locus with a MAF of at least 0.3 as determined according to data from the dbSNP database (NCBI) and/or the NHLBI Exome Sequencing Project (ESP). In an embodiment, the MiHA peptide derives from a locus with a MAF of at least 0.3 as determined according to data from the dbSNP database (NCBI) and the NHLBI Exome Sequencing Project (ESP). In an embodiment, the MiHA peptide derives from a locus with a MAF of at least 0.35 as determined according to data from the dbSNP database (NCBI) and/or the NHLBI Exome Sequencing Project (ESP). In an embodiment, the MiHA peptide derives from a locus with a MAF of at least 0.35 as determined according to data from the dbSNP database (NCBI) and the NHLBI Exome Sequencing Project (ESP). In an embodiment, the MiHA peptide derives from a locus with a MAF of at least 0.4 as determined according to data from the dbSNP database (NCBI) and/or the NHLBI Exome Sequencing Project (ESP). In an embodiment, the MiHA peptide derives from a locus with a MAF of at least 0.4 as determined according to data from the dbSNP database (NCBI) and the NHLBI Exome Sequencing Project (ESP).

In some embodiments, the present invention provides a MiHA peptide comprising any combination/subcombination of the features or properties defined herein, for example, a MiHA peptide of the formula I as defined above, wherein the peptide (i) binds to HLA-A2 molecules, (ii) derives from a gene that does not exhibit ubiquitous expression and (iii) derives from a locus with a MAF of at least 0.1 as determined according to data from the dbSNP database (NCBI) and/or the NHLBI Exome Sequencing Project (ESP).

In general, peptides presented in the context of HLA class I vary in length from about 7 to about 15, or preferably 8 to 14 amino acid residues. In some embodiments of the methods of the invention, longer peptide comprising the MiHA peptide sequences defined herein are artificially loaded into cells such as antigen presenting cells (APCs), processed by the cells and the MiHA peptide is presented by MHC class I molecules at the surface of the APC. In this method, peptides/polypeptides longer than 15 amino acid residues (i.e. a MiHA precursor peptide, such as those defined by formula Ia above) can be loaded into APCs, are processed by proteases in the APC cytosol providing the corresponding MiHA peptide as defined herein for presentation. In some embodiments, the precursor peptide/polypeptide (e.g., polypeptide of formula Ia defined above) that is used to generate the MiHA peptide defined herein is for example 100, 500, 400, 300, 200, 150, 100, 75, 50, 45, 40, 35, 30, 25, 20 or 15 amino acids or less. Thus, all the methods and processes using the MiHA peptides described herein includes the use of longer peptides or polypeptides (including the native protein), i.e. MiHA precursor peptides/polypeptides, to induce the presentation of the "final" 8-14 MiHA peptide following processing by the cell (APCs).

In some embodiments, the above-mentioned MiHA peptide is about 8 to 12 amino acids long (e.g., 8, 9, 10, 11 or 12 amino acids long), small enough for a direct fit in an HLA class I molecule (HLA-A2 or HLA-B44 molecule), but it may also be larger, between 12 to about 20, 25, 30, 35, 40, 45 or 50 amino acids, and a MiHA peptide corresponding to the domain defined by $X^1$ above be presented by HLA molecules only after cellular uptake and intracellular processing by the proteasome and/or other proteases and transport before presentation in the groove of an HLA class I molecule (HLA-A2 or HLA-B44 molecule), as explained above.

In an embodiment, the MiHA peptide consists of an amino acid sequence of 8 to 14 amino acids, e.g., 8, 9, 10, 11, 12, 13, or 14 amino acids, wherein the sequence is the sequences of any one of MiHA Nos. 1-93 set forth in Table I. In another aspect, the present invention provides a MiHA peptide consisting of an amino acid sequence of 8 to 14 amino acids, e.g., 8, 9, 10, 11, 12, 13, 14 or 15 amino acids, said amino acid sequence consisting of the sequence of MIHA Nos. 1-93, preferably MiHAs 7, 8, 10, 14-15, 20-21, 32, 33, 35, 39-47, 49-50, 66, 70-71, 76, 78, 81, 84 and 90 of Table I). In an embodiment, the at least 7 or 8 amino acids of one of MIHA Nos. 1-93, preferably MiHAs 7, 8, 10, 14-15, 20-21, 32, 33, 35, 39-47, 49-50, 66, 70-71, 76, 78, 81, 84 and 90 of Table I are contiguous amino acids. In an embodiment, $X^1$ is a domain comprising at least 8 amino acids of any one of MiHA Nos. 1-93, preferably MiHAs 7, 8, 10, 14-15, 20-21, 32, 33, 35, 39-47, 49-50, 66, 70-71, 76, 78, 81, 84 and 90, wherein said sequence comprises the polymorphic amino acid depicted. In another embodiment, $X^1$ is a sequence comprising, or consisting of, the amino acids of any one of MiHA Nos. 1-93, preferably MiHAs 7, 8, 10, 14-15, 20-21, 32, 33, 35, 39-47, 49-50, 66, 70-71, 76, 78, 81, 84 and 90.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of MiHA peptides. Examples of naturally occurring amino acids are glycine, alanine, valine, leucine, isoleucine, serine, threonine, etc.

Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diaminopropionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Hoarg), N-acetyl lysine, 2-amino butyric acid, 2-amino butyric acid, 2,4-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry. In an embodiment, the MiHA peptide comprises only naturally-occurring amino acids.

In embodiments, the MiHA peptides of the present invention include peptides with altered sequences containing substitutions of functionally equivalent amino acid residues, relative to the above-mentioned sequences. For example, one or more amino acid residues within the sequence can be substituted by another amino acid of a similar polarity (having similar physico-chemical properties) which acts as a functional equivalent, resulting in a silent alteration. Substitution for an amino acid within the sequence may be selected from other members of the class to which the amino acid belongs. For example, positively charged (basic) amino acids include arginine, lysine and histidine (as well as homoarginine and ornithine). Nonpolar (hydrophobic) amino acids include leucine, isoleucine, alanine, phenylalanine, valine, proline, tryptophan and methionine. Uncharged polar amino acids include serine, threonine, cysteine, tyrosine, asparagine and glutamine. Negatively charged (acidic) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions.

The above-mentioned MiHA peptide may comprise all L-amino acids, all D-amino acids or a mixture of L- and D-amino acids. In an embodiment, the above-mentioned MiHA peptide comprises all L-amino acids.

The MiHA peptide may also be N- and/or C-terminally capped or modified to prevent degradation, increase stability or uptake. In an embodiment, the amino terminal residue (i.e., the free amino group at the N-terminal end) of the MiHA peptide is modified (e.g., for protection against degradation), for example by covalent attachment of a moiety/chemical group ($Z^1$). $Z^1$ may be a straight chained or branched alkyl group of one to eight carbons, or an acyl group (R—CO—), wherein R is a hydrophobic moiety (e.g., acetyl, propionyl, butanyl, iso-propionyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), for example an acetyl group ($CH_3$—CO—, Ac). In an embodiment, $Z^1$ is absent.

The carboxy terminal residue (i.e., the free carboxy group at the C-terminal end of the MiHA peptide) of the MiHA peptide may be modified (e.g., for protection against degradation), for example by amidation (replacement of the OH group by a $NH_2$ group), thus in such a case $Z^2$ is a $NH_2$ group. In an embodiment, $Z^2$ may be an hydroxamate group, a nitrile group, an amide (primary, secondary or tertiary) group, an aliphatic amine of one to ten carbons such as methyl amine, iso-butylamine, iso-valerylamine or cyclohexylamine, an aromatic or arylalkyl amine such as aniline, napthylamine, benzylamine, cinnamylamine, or phenylethylamine, an alcohol or $CH_2OH$. In an embodiment, $Z^2$ is absent.

In an embodiment, the MiHA peptide comprises one of sequences Nos. 1-93, preferably MiHAs 7, 8, 10, 14-15, 20-21, 32, 33, 35, 39-47, 49-50, 66, 70-71, 76, 78, 81, 84 and 90 set forth in Table I. In an embodiment, the MiHA peptide consists of one of sequences No. 1-93, preferably MiHAs 7, 8, 10, 14-15, 20-21, 32, 33, 35, 39-47, 49-50, 66, 70-71, 76, 78, 81, 84 and 90 set forth in Table I, i.e. wherein $Z^1$ and $Z^2$ are absent.

The MiHA peptides of the invention may be produced by expression in a host cell comprising a nucleic acid encoding the MiHA peptides (recombinant expression) or by chemical synthesis (e.g., solid-phase peptide synthesis). Peptides can be readily synthesized by manual and/or automated solid phase procedures well known in the art. Suitable syntheses can be performed for example by utilizing "T-boc" or "Fmoc" procedures. Techniques and procedures for solid phase synthesis are described in for example Solid Phase Peptide Synthesis: A Practical Approach, by E. Atherton and R. C. Sheppard, published by IRL, Oxford University Press, 1989. Alternatively, the MiHA peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the MiHA peptides are described in Nakagawa et al., *J. Am. Chem. Soc.* 107: 7087-7092, 1985. In an embodiment, the MiHA peptide of the formula I or Ia is chemically synthesized (synthetic peptide).

Accordingly, in another aspect, the invention further provides a nucleic acid (isolated) encoding the above-mentioned MiHA peptides or a MiHA precursor-peptide. In an embodiment, the nucleic acid comprises from about 21 nucleotides to about 45 nucleotides, from about 24 to about 45 nucleotides, for example 24, 27, 30, 33, 36, 39, 42 or 45 nucleotides.

"Isolated", as used herein, refers to a peptide or nucleic molecule separated from other components that are present in the natural environment of the molecule or a naturally occurring source macromolecule (e.g., including other nucleic acids, proteins, lipids, sugars, etc.). "Synthetic", as used herein, refers to a peptide or nucleic molecule that is not isolated from its natural sources, e.g., which is produced through recombinant technology or using chemical synthesis.

In an embodiment, the above-mentioned MiHA peptide is substantially pure. A compound is "substantially pure" when it is separated from the components that naturally accompany it. Typically, a compound is substantially pure when it is at least 60%, more generally 75%, 80% or 85%, preferably over 90% and more preferably over 95%, by weight, of the total material in a sample. Thus, for example, a polypeptide that is chemically synthesized or produced by recombinant technology will generally be substantially free from its naturally associated components, e.g. components of its source macromolecule. A nucleic acid molecule is substantially pure when it is not immediately contiguous with (i.e., covalently linked to) the coding sequences with which it is normally contiguous in the naturally occurring genome of the organism from which the nucleic acid is derived. A substantially pure compound can be obtained, for example, by extraction from a natural source; by expression of a recombinant nucleic acid molecule encoding a peptide compound; or by chemical synthesis. Purity can be measured using any appropriate method such as column chromatography, gel electrophoresis, HPLC, etc.

A nucleic acid of the invention may be used for recombinant expression of the MiHA peptide of the invention, and may be included in a vector or plasmid, such as a cloning vector or an expression vector, which may be transfected into a host cell. In an embodiment, the invention provides a cloning or expression vector or plasmid comprising a nucleic acid sequence encoding the MiHA peptide of the invention. Alternatively, a nucleic acid encoding a MiHA peptide of the invention may be incorporated into the genome of the host cell. In either case, the host cell expresses the MiHA peptide or protein encoded by the nucleic acid.

The vector or plasmid contains the necessary elements for the transcription and translation of the inserted coding sequence, and may contain other components such as resistance genes, cloning sites, etc. Methods that are well known to those skilled in the art may be used to construct expression vectors containing sequences encoding peptides or polypeptides and appropriate transcriptional and translational control/regulatory elements operably linked thereto. These methods include in vitro recombinant DNA techniques, synthetic techniques, and in vivo genetic recombination. Such techniques are described in Sambrook. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

"Operably linked" refers to a juxtaposition of components, particularly nucleotide sequences, such that the normal function of the components can be performed. Thus, a coding sequence that is operably linked to regulatory sequences refers to a configuration of nucleotide sequences wherein the coding sequences can be expressed under the regulatory control, that is, transcriptional and/or translational control, of the regulatory sequences. "Regulatory/control region" or "regulatory/control sequence", as used herein, refers to the non-coding nucleotide sequences that are involved in the regulation of the expression of a coding nucleic acid. Thus the term regulatory region includes promoter sequences, regulatory protein binding sites, upstream activator sequences, and the like.

In an embodiment, the MiHA peptide is in solution. In another embodiment, the MiHA peptide is in solid form, e.g., lyophilized.

In another aspect, the present invention provides a MHC class I molecule comprising (i.e. presenting or bound to) a MiHA peptide. In an embodiment, the MHC class I molecule is a HLA-A2 molecule, in a further embodiment a HLA-A*02:01 molecule. In another embodiment, the MHC class I molecule is a HLA-B44 molecule, in a further embodiment a HLA-B*44:03 molecule. In another embodiment, the MiHA peptide is non-covalently bound to the MHC class I molecule (i.e., the MiHA peptide is loaded into, or non-covalently bound to the peptide binding groove/pocket of the MHC class I molecule). In another embodiment, the MiHA peptide is covalently attached/bound to the MHC class I molecule (alpha chain). In such a construct, the MiHA peptide and the MHC class I molecule (alpha chain) are produced as a synthetic fusion protein, typically with a short (e.g., 5 to 20 residues, preferably about 8-12, e.g., 10) flexible linker or spacer (e.g., a polyglycine linker). In another aspect, the invention provides a nucleic acid encoding a fusion protein comprising a MiHA peptide defined above fused to a MHC class I molecule (alpha chain). In an embodiment, the MHC class I molecule (alpha chain)-peptide complex is multimerized. Accordingly, in another aspect, the present invention provides a multimer of MHC class I molecule loaded (covalently or not) with the above-mentioned MiHA peptide. Such multimers may be attached to a tag, for example a fluorescent tag, which allows the detection of the multimers. A great number of strategies have been developed for the production of MHC multimers, including MHC dimers, tetramers, pentamers, octamers, etc. (reviewed in Bakker and Schumacher, *Current Opinion in Immunology* 2005, 17:428-433). MHC multimers are useful, for example, for the detection and purification of antigen-specific T cells. Thus, in another aspect, the present invention provides a method for detecting or purifying (isolating, enriching) CD8+ T lymphocytes specific for a MiHA peptide defined above, the method comprising contacting a cell population with a multimer of MHC class I molecule loaded (covalently or not) with the MiHA peptide; and detecting or isolating the CD8+ T lymphocytes bound by the MHC class I multimers. CD8+ T lymphocytes bound by the MHC class I multimers may be isolated using known methods, for example fluorescence activated cell sorting (FACS) or magnetic activated cell sorting (MACS).

In yet another aspect, the present invention provides a cell (e.g., a host cell), in an embodiment an isolated cell, comprising the above-mentioned nucleic acid, vector or plasmid of the invention, i.e. a nucleic acid or vector encoding one or more MiHA peptides.

In another aspect, the present invention provides a cell expressing at its surface a MHC class I molecule (e.g., a HLA-A2 or HLA-B44 allele molecule) bound to or presenting a MiHA peptide according to the invention. In one embodiment, the host cell is a primary cell, a cell line or an immortalized cell. In another embodiment, the cell is an antigen-presenting cell (APC).

Nucleic acids and vectors can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals. Methods for introducing nucleic acids into mammalian cells in vivo are also known, and may be used to deliver the vector DNA of the invention to a subject for gene therapy.

Cells such as APCs can be loaded with one or more MiHA peptides using a variety of methods known in the art. As used herein "loading a cell" with a MiHA peptide means that RNA or DNA encoding the MiHA peptide, or the MiHA peptide, is transfected into the cells or alternatively that the APC is transformed with a nucleic acid encoding the MiHA peptide. The cell can also be loaded by contacting the cell with exogenous MiHA peptides that can bind directly to MHC class I molecule present at the cell surface (e.g., peptide-pulsed cells). The MiHA peptides may also be fused to a domain or motif that facilitates its presentation by MHC class I molecules, for example to an endoplasmic reticulum (ER) retrieval signal, a C-terminal Lys-Asp-Glu-Leu sequence (see Wang et al., *Eur J Immunol.* 2004 December; 34(12):3582-94).

Compositions

In another aspect, the present invention provides a composition or peptide combination comprising any one of, or any combination of, the MiHA peptides defined above (or a nucleic acid encoding said peptide(s)). In an embodiment, the composition comprises any combination of the MiHA peptides defined above (e.g., any combination of MiHAs Nos. 1-93, preferably MiHAs 7, 8, 10, 14-15, 20-21, 32, 33, 35, 39-47, 49-50, 66, 70-71, 76, 78, 81, 84 and 90 set forth in Table I), or a combination of nucleic acids encoding said MiHA peptides). For example, the composition may comprise a first MiHA peptide which correspond to MiHA No. 1 and a second MiHA peptide that corresponds to MiHA No. 24. Compositions comprising any combination/sub-combination of the MiHA peptides defined above are encompassed by the present invention. In another embodiment, the combination may comprise one or more known MiHAs, such as the known MiHAs disclosed herein (see, e.g., Tables III and V). In an embodiment, the composition or peptide combination comprises at least 2, 3, 4, 5, 6, 7, 8, 9, or 10 MiHA peptides, wherein at least one of said MiHA peptide comprising the MiHAs Nos. 1-93

In a further embodiment, a MHC class I molecule (HLA-A2 or HLA-B44) that presents a MiHA peptide is expressed at the surface of a cell, e.g., an APC. In an embodiment, the invention provides an APC loaded with one or more MiHA peptides bound to MHC class I molecules. In yet a further embodiment, the invention provides an isolated MHC class I/MiHA peptide complex.

Thus, in another aspect, the present invention provides a composition comprising any one of, or any combination of, the MiHA peptides defined above and a cell expressing a MHC class I molecule (HLA-A2 or HLA-B44). APC for use in the present invention are not limited to a particular type of cell and include professional APCs such as dendritic cells (DCs), Langerhans cells, macrophages and B cells, which are known to present proteinaceous antigens on their cell surface so as to be recognized by CD8+ T lymphocytes. For example, an APC can be obtained by inducing DCs from peripheral blood monocytes and then contacting (stimulating) the MiHA peptides, either in vitro, ex vivo or in vivo. APC can also be activated to present a MiHA peptide in vivo where one or more of the MiHA peptides of the invention are administered to a subject and APCs that present a MiHA peptide are induced in the body of the subject. The phrase "inducing an APC" or "stimulating an APC" includes contacting or loading a cell with one or more MiHA peptides, or nucleic acids encoding the MiHA peptides such that the MiHA peptides are presented at its surface by MHC class I molecules (e.g., HLA-A2 or HLA-B44). As noted above, according to the present invention, the MiHA peptides may be loaded indirectly for example using longer peptides/polypeptides comprising the sequence of the MiHAs (including the native protein), which is then processed (e.g., by proteases) inside the APCs to generate the MiHA peptide/MHC class I complexes at the surface of the cells.

After loading APCs with MiHA peptides and allowing the APCs to present the MiHA peptides, the APCs can be administered to a subject as a vaccine. For example, the ex vivo administration can include the steps of:
(a) collecting APCs from a first subject, (b) contacting/loading the APCs of step (a) with a MiHA peptide to form MHC class I/MiHA peptide complexes at the surface of the APCs; and (c) administering the peptide-loaded APCs to a second subject in need for treatment.

The first subject and the second subject can be the same individual (e.g., autologous vaccine), or may be different individuals (e.g., allogeneic vaccine). Alternatively, according to the present invention, use of a MiHA peptide of the present invention for manufacturing a pharmaceutical composition for inducing antigen-presenting cells is provided. In addition, the present invention provides a method or process for manufacturing a pharmaceutical composition for inducing antigen-presenting cells, wherein the method or the process includes the step of admixing or formulating the MiHA peptide with a pharmaceutically acceptable carrier.

Cells such as APCs expressing a MHC class I molecule (HLA-A2 or HLA-B44) loaded with any one of, or any combination of, the MiHA peptides defined above, may be used for stimulating/amplifying $CD8^+$ T lymphocytes, for example autologous $CD8^+$ T lymphocytes. Accordingly, in another aspect, the present invention provides a composition comprising any one of, or any combination of, the MiHA peptides defined above (or a nucleic acid or vector encoding same); a cell expressing a MHC class I molecule (HLA-A2 or HLA-B44) and a T lymphocyte, more specifically a $CD8^+$ T lymphocyte (e.g., a population of cells comprising $CD8^+$ T lymphocytes).

In an embodiment, the composition further comprises a buffer, an excipient, a carrier, a diluent and/or a medium (e.g., a culture medium). In a further embodiment, the buffer, excipient, carrier, diluent and/or medium is/are pharmaceutically acceptable buffer(s), excipient(s), carrier(s), diluent(s) and/or medium (media). As used herein "pharmaceutically acceptable buffer, excipient, carrier, diluent and/or medium" includes any and all solvents, buffers, binders, lubricants, fillers, thickening agents, disintegrants, plasticizers, coatings, barrier layer formulations, lubricants, stabilizing agent, release-delaying agents, dispersion media, coatings, antibacterial and antifungal agents, isotonic agents, and the like that are physiologically compatible, do not interfere with effectiveness of the biological activity of the active ingredient(s) and that are not toxic to the subject. The use of such media and agents for pharmaceutically active substances is well known in the art (Rowe et al., Handbook of pharmaceutical excipients, 2003, $4^{th}$ edition, Pharmaceutical Press, London UK). Except insofar as any conventional media or agent is incompatible with the active compound (peptides, cells), use thereof in the compositions of the invention is contemplated. In an embodiment, the buffer, excipient, carrier and/or medium is a non-naturally occurring buffer, excipient, carrier and/or medium.

In one embodiment, the MiHA peptides of the invention are used as a vaccine.

In another aspect, the present invention provides an immunogenic composition comprising one of more of the any one of, or any combination of, the MiHA peptides defined above (or a nucleic acid encoding said peptide(s)), and a buffer, an excipient, a carrier, a diluent and/or a medium.

For compositions comprising cells (e.g., T lymphocytes), the composition comprises a suitable medium that allows the maintenance of viable cells. Representative examples of such media include saline solution, Earl's Balanced Salt Solution (Life Technologies®) or PlasmaLyte® (Baxter International®).

In an embodiment, the composition is an "immunogenic composition" or "vaccine". The term "Immunogenic composition" or "vaccine" as used herein refers to a composition or formulation comprising one or more MiHA peptides or vaccine vector and which is capable of inducing an immune response against the one or more MiHA peptides present therein when administered to a subject. Vaccination methods for inducing an immune response in a mammal comprise use of a vaccine or vaccine vector to be administered by any conventional route known in the vaccine field, e.g., via a mucosal (e.g., ocular, intranasal, pulmonary, oral, gastric, intestinal, rectal, vaginal, or urinary tract) surface, via a parenteral (e.g., subcutaneous, intradermal, intramuscular, intravenous, or intraperitoneal) route, or topical administration (e.g., via a transdermal delivery system such as a patch).

In an embodiment, the MiHA peptide is conjugated to a carrier protein (conjugate vaccine) to increase the immunogenicity of the MiHA peptide. The present invention thus provides a composition (conjugate) comprising a MiHA peptide and a carrier protein. For example, the MiHA peptide may be conjugated to a Toll-like receptor (TLR) ligand (see, e.g., Zom et al., *Adv Immunol*. 2012; 114:177-201) or polymers/dendrimers (see, e.g., Liu et al., *Biomacromolecules*. 2013 Aug. 12; 14(8):2798-806).

In an embodiment, the immunogenic composition or vaccine further comprises an adjuvant. "Adjuvant" refers to a substance which, when added to an immunogenic agent such as an antigen (MiHA peptides and/or cells according to the present invention), nonspecifically enhances or potentiates an immune response to the agent in the host upon exposure to the mixture. Examples of adjuvants currently used in the field of vaccines include (1) mineral salts (aluminum salts such as aluminum phosphate and aluminum hydroxide, calcium phosphate gels), squalene, (2) oil-based adjuvants such as oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), (3) particulate adjuvants, e.g., virosomes (unilamellar liposomal vehicles incorporating influenza haemagglutinin), AS04 ([SBAS4] aluminum salt with MPL), ISCOMS (structured complex of saponins and lipids), polylactide co-glycolide (PLG), (4) microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), (5) endogenous human immunomodulators, e.g., hGM-CSF or hIL-12 (cytokines that can be administered either as protein or plasmid encoded), Immudaptin (C3d tandem array) and/or (6) inert vehicles, such as gold particles, and the like.

In an embodiment, the MiHA peptide(s) or composition comprising same is in lyophilized form. In another embodiment, the MiHA peptide(s) is/are in a liquid composition. In a further embodiment, the MiHA peptide(s) is/are at a concentration of about 0.01 µg/mL to about 100 µg/mL in the composition. In further embodiments, the MiHA peptide(s) is/are at a concentration of about 0.2 µg/mL to about 50

µg/mL, about 0.5 µg/mL to about 10, 20, 30, 40 or 50 µg/mL, about 1 µg/mL to about 10 µg/mL, or about 2 µg/mL, in the composition.

MiHA-Specific TCRs and T Lymphocytes

As noted above, cells such as APCs that express a MHC class I molecule (HLA-A2 or HLA-B44) loaded with or bound to any one of, or any combination of, the MiHA peptides defined above, may be used for stimulating/amplifying CD8$^+$ T lymphocytes in vivo or ex vivo.

Accordingly, in another aspect, the present invention provides T cell receptor (TCR) molecules capable of interacting with or binding the above-mentioned MHC class I molecule/MiHA peptide complex, and nucleic acid molecules encoding such TCR molecules, and vectors comprising such nucleic acid molecules. A TCR according to the present invention is capable of specifically interacting with or binding a MiHA peptide loaded on, or presented by, a MHC class I molecule (HLA-A2 or HLA-B44), preferably at the surface of a living cell in vitro or in vivo. A TCR and in particular nucleic acids encoding a TCR of the invention may for instance be applied to genetically transform/modify T lymphocytes (e.g., CD8$^+$ T lymphocytes) or other types of lymphocytes generating new T lymphocyte clones that specifically recognizing a MHC class I MiHA peptide complex. In a particular embodiment, T lymphocytes (e.g., CD8$^+$ T lymphocytes) obtained from a patient are transformed to express one or more TCRs that recognize MiHA peptide and the transformed cells are administered to the patient (autologous cell transfusion).

In another embodiment, the invention provides a T lymphocyte e.g., a CD8$^+$ T lymphocyte transformed/transfected by a vector or plasmid encoding a MiHA peptide-specific TCR. In a further embodiment the invention provides a method of treating a patient with autologous or allogenic cells transformed with a MiHA-specific TCR. In yet a further embodiment the use of a MiHA specific TCR in the manufacture of autologous or allogenic cells for treating of cancer is provided.

In some embodiments patients treated with the therapeutic compositions of the invention are treated prior to or following treatment with allogenic stem cell transplant (ASCL), allogenic lymphocyte infusion or autologous lymphocyte infusion. Therapeutic compositions of the invention include: allogenic T lymphocytes (e.g., CD8$^+$ T lymphocyte) activated ex vivo against a MiHA peptide; allogenic or autologous APC vaccines loaded with a MiHA peptide; MiHA peptide vaccines and allogenic or autologous T lymphocytes (e.g., CD8$^+$ T lymphocyte) or lymphocytes transformed with a MiHA-specific TCR.

The method to provide T lymphocyte clones capable of recognizing an MiHA peptide according to the invention may be generated for and can be specifically targeted to tumor cells expressing the MiHA in a subject (e.g., graft recipient), for example an ASCT and/or donor lymphocyte infusion (DLI) recipient. Hence the invention provides a CD8$^+$ T lymphocyte encoding and expressing a T cell receptor capable of specifically recognizing or binding a MiHA peptide/MHC class I molecule complex. Said T lymphocyte (e.g., CD8$^+$ T lymphocyte) may be a recombinant (engineered) or a naturally selected T lymphocyte. This specification thus provides at least two methods for producing CD8$^+$ T lymphocytes of the invention, comprising the step of bringing undifferentiated lymphocytes into contact with a MiHA peptide/MHC class I molecule complex (typically expressed at the surface of cells, such as APCs) under conditions conducive of triggering T cell activation and expansion, which may be done in vitro or in vivo (i.e. in a patient administered with a APC vaccine wherein the APC is loaded with a MiHA peptide or in a patient treated with a MiHA peptide vaccine). Alternatively, MiHA-specific or targeted T lymphocytes may be produced/generated in vitro or ex vivo by cloning one or more nucleic acids (genes) encoding a TCR (more specifically the alpha and beta chains) that specifically binds to a MHC class I molecule/MiHA complex (i.e. engineered or recombinant CD8$^+$ T lymphocytes). Nucleic acids encoding a MiHA-specific TCR of the invention, may be obtained using methods known in the art from a T lymphocyte activated against a MiHA peptide ex vivo (e.g., with an APC loaded with a MiHA peptide); or from an individual exhibiting an immune response against peptide/MHC molecule complex. MiHA-specific TCRs of the invention may be recombinantly expressed in a host cell and/or a host lymphocyte obtained from a graft recipient or graft donor, and optionally differentiated in vitro to provide cytotoxic T lymphocytes (CTLs). The nucleic acid(s) (transgene(s)) encoding the TCR alpha and beta chains may be introduced into a T cells (e.g., from a subject to be treated or another individual) using any suitable methods such as transfection (e.g., electroporation) or transduction (e.g., using viral vector). The engineered CD8$^+$ T lymphocytes expressing a TCR specific for a MiHA may be expanded in vitro using well known culturing methods.

The present invention provides isolated CD8$^+$ T lymphocytes that are specifically induced, activated and/or amplified (expanded) by a MiHA peptide (i.e., a MiHA peptide bound to MHC class I molecules expressed at the surface of cell). The present invention also provides a composition comprising CD8$^+$ T lymphocytes capable of recognizing an MiHA peptide according to the invention (i.e., a MiHA peptide bound to MHC class I molecules) and said MiHA peptide.

In another aspect, the present invention provides a cell population or cell culture (e.g., a CD8$^+$ T lymphocyte population) enriched in CD8$^+$ T lymphocytes that specifically recognize a MHC class I molecule/MiHA peptide complex as described herein. Such enriched population may be obtained by performing an ex vivo expansion of specific T lymphocytes using cells such as APCs that express MHC class I molecules loaded with e.g. presenting) one or more of the MiHA peptides disclosed herein. "Enriched" as used herein means that the proportion of MiHA-specific CD8$^+$ T lymphocytes in the population is significantly higher relative to a native population of cells, i.e. which has not been subjected to a step of ex vivo-expansion of specific T lymphocytes. In a further embodiment, the proportion of MiHA-specific CD8$^+$ T lymphocytes in the cell population is at least about 0.5%, for example at least about 1%, 1.5%, 2% or 3%. In some embodiments, the proportion of MiHA-specific CD8$^+$ T lymphocytes in the cell population is about 0.5 to about 10%, about 0.5 to about 8%, about 0.5 to about 5%, about 0.5 to about 4%, about 0.5 to about 3%, about 1% to about 5%, about 1% to about 4%, about 1% to about 3%, about 2% to about 5%, about 2% to about 4%, about 2% to about 3%, about 3% to about 5% or about 3% to about 4%. Such cell population or culture (e.g., a CD8$^+$ T lymphocyte population) enriched in CD8$^+$ T lymphocytes that specifically recognizes a MHC class I molecule/peptide (MiHA) complex of interest may be used in MiHA-based cancer immunotherapy, as detailed below.

In some embodiments, the population of MiHA-specific CD8$^+$ T lymphocytes is further enriched, for example using affinity-based systems such as multimers of MHC class I molecule loaded (covalently or not) with the MiHA peptide defined above. Thus, the present invention provides a purified or isolated population of MiHA-specific CD8+ T lymphocytes, e.g., in which the proportion of MiHA-specific CD8+ T lymphocytes is at least 50%, 60%, 70%, 80%, 85%, 90% or 95%.

MiHA-Based Cancer Immunotherapy

The MiHA peptide sequences identified herein may be used for the production of synthetic peptides to be used i) for in vitro priming and expansion of MiHA-specific T cells to be injected into transplant (AHCT) recipients and/or ii) as vaccines to boost the graft-vs.-tumor effect (GvTE) in recipients of MiHA-specific T cells, subsequent to the transplantation.

The potential impact of the therapeutic methods provided by the present invention, MiHA-targeted cancer immunotherapy is significant. For hematologic cancers (e.g., leukemia, lymphoma and myeloma), the use of anti-MiHA T cells may replace conventional AHCT by providing superior anti-tumor activity without causing GvHD. It may benefit many patients with hematologic malignancy who cannot be treated by conventional AHCT because their risk/reward (GvHD/GVT) ratio is too high. Finally, since studies in mice have shown that MiHA-targeted immunotherapy may be effective for treatment of solid tumors, MiHA-based cancer immunotherapy may be used for MiHA-targeted therapy of non-hematologic cancers, such as solid cancers.

In embodiment, the cancer is leukemia including but not limited to acute lymphoblastic leukemia (ALL), acute myeloid leukemia (AML), chronic lymphocytic leukemia (CLL) chronic myeloid leukemia (CML), Hairy cell leukemia (HCL), T-cell prolymphocytic leukemia (T-PLL), Large granular lymphocytic leukemia or Adult T-cell leukemia. In another embodiment, the cancer is lymphoma including but not limited to Hodgkin lymphoma (HL), non-Hodgkin lymphoma (NHL), Burkitt's lymphoma, Precursor T-cell leukemia/lymphoma, Follicular lymphoma, Diffuse large B cell lymphoma, Mantle cell lymphoma, B-cell chronic lymphocytic leukemia/lymphoma or MALT lymphoma. In a further embodiment, the cancer is a myeloma (multiple myeloma) including but not limited to plasma cell myeloma, myelomatosis, and Kahler's disease.

In another aspect, the present invention provides the use of a MiHA peptide of the present invention as a vaccine for treating cancer in a subject. In an embodiment, the subject is a recipient of MiHA-specific CD8+ T lymphocytes.

Accordingly, in another aspect, the present invention provides a method of treating cancer (e.g., of reducing the number of tumor cells, killing tumor cells), said method comprising administering (infusing) to a subject in need thereof an effective amount of CD8+ T lymphocytes recognizing (i.e. expressing a TCR that binds) a MHC class I molecule/MiHA peptide complex (expressed at the surface of a cell such as an APC). In an embodiment, the method further comprises administering an effective amount of the MiHA peptide, and/or a cell (e.g., an APC such as a dendritic cell) expressing MHC class I molecule loaded with the MiHA peptide, to said subject after administration/infusion of said CD8+ T lymphocytes. In yet a further embodiment, the method comprises administering to a subject in need thereof a therapeutically effective amount of a dendritic cell loaded with one or more MiHA peptides. In yet a further embodiment the method comprises administering to a patient in need thereof a therapeutically effective amount of a allogenic or autologous cell that expresses a recombinant TCR that binds to a MiHA peptide presented by a MHC class I molecule.

In another aspect, the present invention provides the use of CD8+ T lymphocytes that recognize a MHC class I molecule loaded with (presenting) a MiHA peptide for treating cancer (e.g., of reducing the number of tumor cells, killing tumor cells) in a subject. In another aspect, the present invention provides the use of CD8+ T lymphocytes that recognize a MHC class I molecule loaded with a MiHA peptide for the preparation/manufacture of a medicament for treating cancer (e.g., fir reducing the number of tumor cells, killing tumor cells) in a subject.

In another aspect, the present invention provides CD8+ T lymphocytes that recognize a MHC class I molecule loaded with (presenting) a MiHA peptide for use in the treatment of cancer (e.g., for reducing the number of tumor cells, killing tumor cells) in a subject.

In a further embodiment, the use further comprises the use of an effective amount of a MiHA peptide, and/or of a cell (e.g., an APC) that expresses a MHC class I molecule loaded with (presenting) a peptide of formula I, after the use of said MiHA-specific CD8+ T lymphocytes.

In an embodiment, the subject infused or treated with MiHA-specific CD8 T-cells has received prior treatment with AHCT or donor lymphocyte infusions (i.e. lymphocytes, including T-cells, that have not been activated in vitro against a MiHA peptide presented by a MHC class I molecule. In a further embodiment, the cancer is a hematologic cancer, e.g., leukemia, lymphoma and myeloma. In an embodiment, the cancer is leukemia.

Treatment and Donor Selection Methods

Allogenic therapeutic cells of the invention express a TCR that recognizes a MiHA peptide that is presented by a patient's (recipient's) tumor cells but not presented by cells of the donor. The invention provides a method of selecting an effective therapeutic composition for a patient having hematological cancer comprising: (a) obtaining a biological sample from the patient; (b) determining the presence or absence of one or more SNPs selected from Table II; (c) determining the expression of RNA or protein products corresponding to one or more of the SNPs provided in Table II in a tumor sample from the patient. For treatment with allogenic cells: (a) a donor that does not express a genetic variant, corresponding to a MiHA peptide (i.e. those provided in Table II herein) presented by MHC class I molecules expressed by the recipient's cancer cells is selected (b) lymphocytes are obtained from the donor and (c) CD8+ T lymphocytes specific for the presented MiHA peptide are prepared using the methods provided herein and administered to the patient. Alternatively allogenic cells obtained from the selected donor, one that does not express the MiHA of interest, can be genetically transformed to express a TCR against the MiHA of interest and administered to the patient.

For treatment with autologous cells, an autologous T lymphocyte expressing a TCR that recognizes a MiHA presented by MHC class I molecules present on the cell surface of a patient's cancer cells is administered. The invention provides a method of selecting a T lymphocyte therapy for a patient comprising: (a) obtaining a biological sample from the patient; (b) determining the presence or absence of one or more SNPs selected from Table II; (c) determining the expression of RNA or protein products corresponding to one or more of the SNPs provided in Table II in a tumor sample from the patient.

To determine which variant of a given MiHA that should be used in the treatment of a subject (e.g., using MiHA No. 1 as an example, to determine which of SED ID NO: 80 or 81 should be used), the allelic variant expressed by the subject should be first determined. The amino acid substitutions in the proteins as well as the nucleotide substitutions in the transcripts corresponding to the novel MiHAs described herein (Table II) may be easily identified by the skilled person, for example using the information provided in public databases. For example, Table II includes the reference/identification No. for MiHAs in the dbSNP database, which provides detailed information concerning the variations at the genomic, transcript and protein levels. Based on this information, the determination of the variant (polymorphism or single nucleotide polymorphism (SNP)) expressed by the subject may be readily performed at the nucleic acid and/or protein level on a sample by a number of methods which are known in the art. Table II also includes the reference ID in the Ensembl database for the genes from which the MiHA peptides are derived.

Examples of suitable methods for detecting alterations at the nucleic acid level include sequencing the relevant portion (comprising the variation) of the nucleic acid of interest (e.g., a mRNA, cDNA or genomic DNA encoding the MiHAs), hybridization of a nucleic acid probe capable of specifically hybridizing to a nucleic acid of interest comprising the polymorphism (the first allele) and not to (or to a lesser extent to) a corresponding nucleic acid that do not comprise the polymorphism (the second allele) (under comparable hybridization conditions, such as stringent hybridization conditions), or vice-versa; restriction fragment length polymorphism analysis (RFLP); Amplified fragment length polymorphism PCR (AFLP-PCR); amplification of a nucleic acid fragment using a primer specific for one of the allele, wherein the primer produces an amplified product if the allele is present and does not produce the same amplified product when the other allele is used as a template for amplification (e.g., allele-specific PCR). Other methods include in situ hybridization analyses and single-stranded conformational polymorphism analyses. Further, nucleic acids of interest may be amplified using known methods (e.g., polymerase chain reaction [PCR]) prior to or in conjunction with the detection methods noted herein. The design of various primers for such amplification is known in the art. The nucleic acid (mRNA) may also be reverse transcribed into cDNA prior to analysis.

Examples of suitable methods for detecting alterations/polymorphisms at the polypeptide level include sequencing of the relevant portion (comprising the variation) of the polypeptide of interest, digestion of the polypeptide followed by mass spectrometry or HPLC analysis of the peptide fragments, wherein the variation/polymorphism of the polypeptide of interest results in an altered mass spectrometry or HPLC spectrum; and immunodetection using an immunological reagent (e.g., an antibody, a ligand) which exhibits altered immunoreactivity with a polypeptide comprising the alteration (first allele) relative to a corresponding native polypeptide not comprising the alteration (second allele), for example by targeting an epitope comprising the amino acid variation. Immunodetection can measure the amount of binding between a polypeptide molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots, and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999).

All these detection techniques may also be employed in the format of microarrays, protein-arrays, antibody microarrays, tissue microarrays, electronic biochip or protein-chip based technologies (see Schena M., *Microarray Biochip Technology*, Eaton Publishing, Natick, Mass., 2000).

In one embodiment the invention provides a method of selecting an effective therapeutic composition for a patient comprising: (a) isolating MHC class I presented peptides from hematologic cancer cells from the patient; and (b) identifying the presence or absence of one or more MiHA peptides depicted in Table I among said MHC class I presented peptides. In a further embodiment, the identification of the presence or absence of the one or more MiHA peptides depicted in Table I is performed by mass spectrometry and/or using an antibody detection reagent that is selective for the one or more MiHA peptides. Detecting or identifying MiHA peptides using mass spectrometry can be performed using methods known in the art such as those described in PCT publication No. WO2014/026277. Mass spectrometry (MS) sequencing of MiHA peptides presented by MHC class I molecules, which have been isolated from a sample of cancer cells, involves comparing a MS spectra obtained for an isolated and digested peptide to spectra computed in silico for a MiHA peptide.

Therapeutic allogenic T lymphocytes of the present invention, for treating a patient with cancer, target MHC class I molecules presenting one or more MiHA peptides that is/are expressed by cancer cells in the patient but not expressed by the donor's cells. As such, selecting an appropriate donor for generating allogenic T lymphocytes of the invention involves genotyping candidate donors for the presence or absence of one or more single nucleotide polymorphisms provided in Table II.

In one embodiment the invention provides a method of selecting an effective immunotherapy treatment (i.e. MHC class I molecule/MiHA peptide complex target) for a patient with cancer comprising: determining the presence of MiHA peptides presented by MHC class I molecules in tumor cells from the patient.

In another embodiment the invention provides a method of screening candidate allogenic cell donors for a patient comprising determining the presence or absence of one or more SNPs selected from those provided in Table II in a biological sample from the donor. In an embodiment, the presence or absence of a SNP corresponding to a MiHA peptide known to be presented by MHC class I molecule in cancer cells obtained from a patient is determined in candidate donors. In a further embodiment, biological samples obtained from candidate allogenic donors are genotyped to determine the presence or absence of one or more SNPs known to be carried by a patient, wherein the SNPs detected are selected from those provided in Table II.

In a further embodiment the invention provides a genotyping system comprising a plurality of oligonucleotide probes conjugated to a solid surface for detection of a plurality of SNPs selected from Table II.

For example, to determine which variant of MiHA No. 1 (SEQ ID Nos. 80 or 81) should be used in the treatment of a subject, it should be determined on a sample from the subject using any suitable method (sequencing, etc.) whether (i) a transcript from the ANKRD13A gene comprises a T or C at a position corresponding to position 1680 of Ensembl Transcript ID No. ENST0000261739 (ENSG00000076513); (ii) the nucleotide corresponding to position 110036265 of chromosome 12 in human genome assembly GRCh38 is C or T; and/or (iii) an ANKRD13A polypeptide comprises a leucine or proline residue at a position corresponding to position 505 of the polypeptide encoded by Ensembl Transcript ID No. ENST0000261739 (ENSG00000076513). If (i) the transcript from the ANKRD13A gene comprises a T at a position corresponding to position 1680 of Ensembl Transcript ID No. ENST0000261739; (ii) the nucleotide corresponding to position 110036265 of chromosome 12 in human genome assembly GRCh38 is T; and/or (iii) the ANKRD13A polypeptide comprises a leucine residue at a position corresponding to position 505 of the polypeptide encoded by Ensembl Transcript ID No. ENST0000261739, MiHA variant of SEQ ID No. 80 (SLLESSRSQEL) should be used. Alternatively, if (i) the transcript from the ANKRD13A gene comprises a C at a position corresponding to position 1680 of Ensembl Transcript ID No. ENST0000261739; (ii) the nucleotide corresponding to position 110036265 of chromosome 12 in human genome assembly GRCh38 is C; and/or (iii) the ANKRD13A polypeptide comprises a proline residue at a position corresponding to position 505 of the polypeptide encoded by Ensembl Transcript ID No. ENST0000261739, MiHA variant of SEQ ID No. 81 (SLLESSRSQEP) should be used. The same approach may be applied to determine which variant of any of MiHAs Nos. 2-5, 7-25, 27-30 and 32-84 should be used in a given subject.

MiHAs Nos. 34 and 35 may only be used in male subjects (since the encoding gene is located on chromosome Y, the MiHA is only expressed in male subjects).

In an embodiment, the above-mentioned CD8+ T lymphocytes are in vitro or ex vivo expanded CD8+ T lymphocytes, as described above. Expanded CD8+ T lymphocytes may be obtained by culturing primary CD8+ T lymphocytes (from an allogenic donor) under conditions permitting the proliferation (amplification) and/or differentiation of the CD8+ T lymphocytes. Such conditions typically include contacting the CD8+ T lymphocytes with cells, such as APCs, expressing at their surface the MiHA peptide/MHC complexes of interest, in the presence of a suitable medium (medium for hematopoietic/lymphoid cells, e.g., X-VIVO™15 and AIM-V®) growth factors and/or cytokines such as IL-2, IL-7 and/or IL-15 (see, e.g., Montes et al., Clin Exp Immunol. 2005 November; 142(2):292-302). Such expanded CD8+ T lymphocytes are then administered to the recipient, for example through intravenous infusion. Methods and conditions for amplifying and preparing antigen-specific CD8+ T lymphocytes for adoptive immunotherapy are disclosed, for example, in DiGiusto et al., Cytotherapy 2007; 9(7): 613-629 and Bollard et al., Cytotherapy. 2011 May; 13(5): 518-522). Standard Operating procedures (SOPs) for amplifying antigen-specific CD8+ T lymphocytes are available from the Center for Cell and Gene Therapy, Baylor College of Medicine, Texas Children's Hospital, The Methodist Hospital, Houston, Tex., USA (see Sili et al., Cytotherapy. 2012 January; 14(1): 7-11, Supplementary Material).

In an embodiment, the subject (recipient) is an allogeneic stem cell transplantation (ASCT) or donor lymphocyte infusion (DLI) recipient.

In another aspect, the present invention provides a method of expanding CD8+ T lymphocytes (e.g., for adoptive T-cell immunotherapy), said method comprising (a), culturing CD8+ T lymphocytes from a first individual not expressing a variant of a MiHA peptide in the presence of cells expressing a MHC class I molecule of the HLA-A2 and/or HLA-B44 allele loaded with said variant of the MiHA peptide, under conditions suitable for CD8+ T lymphocyte expansion.

In another aspect, the invention provides a method of producing/manufacturing cells for cellular immunotherapy comprising: culturing human lymphocytes in the presence of APC comprising a MiHA peptide presented by a MHC class I molecule, wherein the MHC class I molecule is of the HLA-A2 or ALA-B44 subtype. The human T lymphocyte used in this method is an allogenic cell i.e. a cell obtained from a donor being manufactured for treating a recipient with an allogenic cell.

In another aspect, the invention provides a method of producing/manufacturing cells for cellular immunotherapy comprising: (a) obtaining lymphocytes (e.g., T lymphocytes) from a cultured cell line and (b) culturing the cells in the presence of APC comprising a MHC class I molecule/MiHA peptide complex wherein the MHC class I molecule is a HLA-A2 or ALA-B44 subtype. The human T lymphocyte used in the method is preferably an allogenic cell i.e. a cell obtained from a donor being manufacture for treating a recipient with an allogenic cell.

In a further embodiment, the invention provides a method of producing/manufacturing cells for cellular immunotherapy comprising: (a) obtaining cells from a donor, e.g., a patient having a hematopoietic cancer (e.g., leukemia) or a healthy individual, for example by leukapheresis, and (b) transforming the cells with a recombinant TCR that binds to a MHC class I molecule/MiHA peptide complex.

In a further embodiment, the invention provides a method of manufacturing cells for cellular immunotherapy comprising transforming a human cell line with a recombinant TCR that binds with to a MHC class I molecule/MiHA peptide complex as defined herein.

In another aspect, the present invention provides a method of expanding CD8+ T lymphocytes for adoptive T-cell immunotherapy, said method comprising (a) determining which variant of any of MiHA Nos. 1-93, preferably MiHAs 7, 8, 10, 14-15, 20-21, 32, 33, 35, 39-47, 49-50, 66, 70-71, 76, 78, 81, 84 and 90 is expressed by a subject (recipient), culturing CD8+ T lymphocytes from a candidate donor in the presence of cells expressing a MHC class I molecule of the HLA-A2 and/or HLA-B44 allele loaded with the MiHA variant expressed by the subject, under conditions suitable for CD8+ T lymphocyte expansion, wherein said candidate donor does not express the MiHA variant (expressed by the subject (recipient)).

In another aspect, the invention provides a method of selecting a therapeutic approach for a patient having leukemia: (a) detecting the presence of a MiHA peptide presented by a MHC class I molecule expressed in leukemic cells obtained from the patient; and (b) determining the presence or absence of a SNP corresponding to the MiHA peptide detected in step (a), as indicated in Table II, in biological samples obtained from candidate donors.

In another aspect, the invention provides a method of preparing a therapeutic composition for a patient having leukemia: (a) detecting the presence of a MiHA peptide presented by a MHC class I molecule expressed in leukemic cells obtained from the patient; (b) obtaining lymphocytes from the patient by leukapheresis, and (c) transforming said lymphocytes with a TCR that recognizes the presented MiHA peptide detected in step (a).

In another aspect, the invention provides a method of preparing a therapeutic composition for a patient having leukemia: (a) genotyping the patient to determine the presence of a plurality of SNPs selected from Table II; (b)

determining the presence of one of the SNPs in the patient (c) obtaining cells from the patient by leukapheresis, and (d) incubating said cells with a APC expressing a MHC class I molecule/MiHA peptide complex, comprising a MiHA peptide that contains the polymorphism encoded by the SNP present in said patient.

Again using MiHA No. 1 (SEQ ID NO: 79) as a representative example to illustrate the method, if it is determined that in a sample from the subject: (i) the transcript from the ANKRD13A gene comprises a T at a position corresponding to position 1680 of Ensembl Transcript ID No. ENST0000261739; (ii) the nucleotide corresponding to position 110036265 of chromosome 12 in human genome assembly GRCh38 is T; and/or (iii) the ANKRD13A polypeptide comprises a leucine residue at a position corresponding to position 505 of the polypeptide encoded by Ensembl Transcript ID No. ENST0000261739, the CD8$^+$ T lymphocytes from the candidate donor are cultured in the presence of cells expressing a MHC class I molecule of the HLA-A2 allele loaded with MiHA variant of SEQ ID No. 80 (SLLESSRSQEL) under conditions suitable for CD8$^+$ T lymphocyte expansion. Alternatively, if it is determined that in a sample from the subject: (i) the transcript from the ANKRD13A gene comprises a C at a position corresponding to position 1680 of Ensembl Transcript ID No. ENST0000261739; (ii) the nucleotide corresponding to position 110036265 of chromosome 12 in human genome assembly GRCh38 is C; and/or (iii) the ANKRD13A polypeptide comprises a proline residue at a position corresponding to position 505 of the polypeptide encoded by Ensembl Transcript ID No. ENST0000261739, the CD8$^+$ T lymphocytes from the candidate donor are cultured in the presence of cells expressing a MHC class I molecule of the HLA-A2 allele loaded with MiHA variant of SEQ ID No. 81 (SLLESSRSQEP) under conditions suitable for CD8$^+$ T lymphocyte expansion. The same approach may be applied to any of MiHAs Nos. 2-93 defined herein.

In an embodiment, the present invention provides a method of treating cancer, said method comprising (i) expanding CD8$^+$ T lymphocytes recognizing a MHC class I molecule loaded with a peptide of formula I for adoptive T-cell immunotherapy according to the method defined above; and (ii) administering (infusing) to a subject in need thereof an effective amount of the expanded CD8$^+$ T lymphocytes. In one embodiment, the method further comprises administering an effective amount of the peptide of formula I, and/or a cell (e.g., an APC) expressing MHC class I molecule loaded with a MiHA peptide of formula I, to said subject after administration/infusion of said CD8$^+$ T lymphocytes.

In embodiment, the above-mentioned cancer comprises tumor cells expressing the genes encoding MiHAs Nos. 1-93, preferably MiHAs 7, 8, 10, 14-15, 20-21, 32, 33, 35, 39-47, 49-50, 66, 70-71, 76, 78, 81, 84 and 90 set forth in Table I.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

MODE(S) FOR CARRYING OUT THE INVENTION

The present invention is illustrated in further details by the following non-limiting examples.

Example 1: Materials and Methods

The MiHAs were identified according to the method/strategy described in PCT publication No. WO 2014/026277 and (3). A schematic overview of the procedure is depicted in FIG. 1.

Cell Culture.

Peripheral blood mononuclear cells (PBMCs) were isolated from blood samples of 6 female and 7 male volunteers expressing at least one of the following two common alleles HLA-A*02:01 and HLA-B*44:03. Epstein-Barr virus (EBV)-transformed B lymphoblastoid cell lines (B-LCLs) were derived from PBMCs with Ficoll-Paque™ Plus (Amersham) as previously described (Tosato and Cohen, 2007). Established B-LCLs were maintained in RPMI 1640 medium supplemented with 10% fetal bovine serum, 25 mM of HEPES, 2 mM L-glutamine and penicillin-streptomycin (all from Invitrogen).

DNA Extraction.

Genomic DNA was extracted from 5 million B-LCLs using the PureLink™ Genomic DNA Mini Kit (Invitrogen®) according to the manufacturer's instructions. DNA was quantified and quality-assessed using the Taqman® RNase P Detection Reagents Kit (Life Technologies®).

HLA Typing.

High-resolution HLA genotyping was performed using 500 ng of genomic DNA at the Maisonneuve-Rosemont Hospital.

Preparation of Genomic DNA Libraries.

Genomic libraries were constructed from 200 ng of genomic DNA using the Ion AmpliSeq™ Exome RDY Library Preparation Kit (Life Technologies®) following the manufacturer's protocol. This included the following steps: amplification of targets, partial digestion of primer sequences, ligation of Ion Xpress™ barcode adapters to the amplicons, purification of the library using AMPure® XP reagent (Beckman Coulter®) and quantification of the unamplified library by qPCR. Library templates were then prepared and loaded onto Ion Proton™ I chips using the Ion PI™ IC 200 kit and the Ion Chef™ System.

Exome Sequencing and Variant Calling.

Two exome libraries were sequenced per chip on an Ion Proton™ Sequencer using the default parameters of AmpliSeq™ exome libraries. Variant calling was done using the Torrent Variant Caller plugin with the "germ Line Proton-Low Stringency" parameter of the Ion reporter Software.

RNA Extraction.

Total RNA was isolated from 5 million B-LCLs using TRizol RNA reagent (Life Technologies®) including DNase I treatment (Qiagen®) according to the manufacturer's instructions. Total RNA was quantified using the NanoDrop™ 2000 (Thermo Scientific®) and RNA quality was assessed with the 2100 Bioanalyzer™ (Agilent Technologies®).

Preparation of Transcriptome Libraries.

Libraries were generated from 1 μg of total RNA using the TruSeq™ RNA Sample Prep Kit (v2) (RS-930-1021, Illumina®) following the manufacturer's protocol. Briefly, poly-A mRNA was purified using poly-T oligo-attached magnetic beads using two rounds of purification. During the second elution of the poly-A RNA, the RNA was fragmented and primed for cDNA synthesis. Reverse transcription (RT) of the first strand was done using random primers and SuperScript™ II (InvitroGene®). A second round of RT was also done to generate a double-stranded cDNA, which was then purified using Agencourt AMpure™ XP PCR purification system (Beckman Coulter®). End repair of fragmented cDNA, adenylation of the 3' ends and ligation of adaptors were done following the manufacturer's protocol. Enrichment of DNA fragments containing adapter molecules on both ends was done using 15 cycles of PCR amplification and the Illumina® PCR mix and primers cocktail.

Whole Transcriptome Sequencing (RNA-Seq).

Paired-end (2×100 bp) sequencing was performed using the Illumina HiSeq2000™ machine running TruSeq™ v3 chemistry. Cluster density was targeted at around 600-800 k clusters/mm². Two transcriptomes were sequenced per lane (8 lanes per slide). Details of the Illumina sequencing technologies can be found at http://www.illumina.com/applications/detail/sequencing/dna_sequencing.ilmn.

Read Mapping.

Sequence data were mapped to the human reference genome (hg19, UCSC) using the Ilumina Casava™ 1.8.1 and the Eland T™ v2 mapping softwares. First, the *.bcl files were converted into compressed FASTQ files, following by demultiplexing of separate multiplexed sequence runs by index. Then, single reads were aligned to the human reference genome including the mitochondrial genome using the multiseed and gapped alignment method. Reads that mapped at 2 or more locations (multireads) were not included in further analyses. An additional alignment was done against splice junctions and contaminants (ribosomal RNA).

Identification of Single Nucleotide Variations in the Transcriptome.

First, the list of all single nucleotide variations observed between the reference genome (GRCh37.p2, NCBI) and the sequenced transcriptome of each of the individuals was retrieved. This was done using the SNP calling program Casava™ v1.8.2 from Ilumina® (http://support.illumina.com/sequencing/sequencing_software/casava.ilmn). Only high confidence single nucleotide variations (Qmax_gt value>20) and that were observed in at least 3 reads (coverage≥3) were considered. SNVs with Qmax_gt value below this threshold were assigned with the reference base instead. This strategy was used to identify single nucleotide variations at the transcript level between each of the individuals and the reference genome.

In Silico Translated Transcriptome.

The sequences containing the identified single nucleotide variations of each individual were further processed. For each sequence, all transcripts reported in Ensembl (http://useast.ensembl.org/info/data/ftp/index.html, Flicek et al., Ensembl 2012, *Nucleic Acids Research* 2012 40 Database issue:D84-D90) were retrieved and in silico translated into proteins using an in-house software pyGeno version (python package pyGeno 1.1.7, https://pypi.python.org/pypi/pyGeno/1.1.7), Granados et al., 2012 (PMID: 22438248)). The in silico translated transcriptomes included cases in which more than one non-synonymous polymorphism was found for a given position. Considering that most MAPs have a maximum length of 11 amino acids (33 bp), the existence of a heterozygous position could lead to MiHA variants in a window of 21 (66 bp) amino acids centered at each ns-SNP. When a window contained more than one ns-SNP, all possible combinations were translated. The number of combinations affected by one ns-SNP was limited to 10,240 to limit the size of the file. In this way, a list of all possible sequences of at most 11 amino acids affected by ns-SNPs was obtained and included in the individual-specific protein databases, which were further used for the identification of MAPs.

Mass Spectrometry and Peptide Sequencing.

3 to 4 biological replicates of 5-6×10$^8$ exponentially growing B-LCLs were prepared from each individual. MHC class I-associated peptides were released by mild acid treatment, pretreated by desalting with an HLB cartridge and filtered with a 3,000 Da cut-off column as previously described (Caron et al. 2011 (PMID: 21952136)). Samples were further processed according to two different methods. In the first method, samples were vacuum dried, resuspended in SCX Reconstitution Solution (Protea®) and separated into six fractions using SCX spintips (Protea®) and an ammonium formate buffer step gradient (50, 75, 100, 300, 600, 1500 mM). Vacuum dried fractions were resuspended in 5% acetonitrile, 0.2% formic acid and analyzed by LC-MS/MS using an Eksigent® LC system coupled to a LTQ-Orbitrap ELITE™ mass spectrometer (Thermo Electron®). Peptides were separated on a custom C18 reversed phase column (pre-column: 0.3 mm i.d.×5 mm, analytical column: 150 μm i.d.×100 mm; Jupiter® C18 3 μm 300 Å) using a flow rate of 600 nL/min and a linear gradient of 5-40% aqueous ACN (0.2% formic acid) in 56 min. Full mass spectra were acquired with the Orbitrap® analyzer operated at a resolving power of 60,000 (at m/z 400). Mass calibration used an internal lock mass (protonated $(Si(CH_3)_2O))_6$; m/z 445.120029) and mass accuracy of peptide measurements was within 5 ppm. MS/MS spectra were acquired at higher energy collisional dissociation with normalized collision energy of 28. Up to ten precursor ions were accumulated to a target value of 50,000 with a maximum injection time of 100 ms and fragment ions were transferred to the Orbitrap® analyzer operating at a resolution of 60,000 at m/z 400. In the second method, samples were split into two identical technical replicates following the 3,000 Da filtration step and vacuum-dried. One technical replicate was resuspended in 3% acetonitrile, 0.2% formic acid and analyzed by LC-MS/MS using an EASY-nLC® II system coupled to a Q-Exactive™ Plus mass spectrometer (Thermo Scientific®). Peptides were separated on a custom C18 reversed phase column as in the first method, using a flow rate of 600 nl/min and a linear gradient of 3-25% aqueous ACN (0.2% formic acid) in 146 min followed by 25-40% in 5 min. Full mass spectra were acquired with the Orbitrap® analyzer operated at a resolving power of 70,000 (at m/z 400). Mass calibration used an internal lock mass (protonated $(Si(CH_3)_2O))_6$; m/z 445.120029) and mass accuracy of peptide measurements was within 5 ppm. MS/MS spectra were acquired at higher energy collisional dissociation with normalized collision energy of 25. Up to twelve precursor ions were accumulated to a target value of 1,000,000 with a maximum injection time of 200 ms and fragment ions were transferred to the Orbitrap® analyser operating at a resolution of 17,500 at m/z 400.

MS/MS Sequencing and Peptide Clustering.

Database searches were performed against databases specific to each individual (see 'in silico-generated proteome and personalized databases' section) using PEAKS®7 (Bioinformatics Solutions Inc., http://www.bioinfor.com/). Mass tolerances for precursor and fragment ions were set to 5 p.p.m. and 0.02 Da, respectively. Searches were performed without enzyme specificity and with variable modifications for cysteinylation, phosphorylation (Ser, Thr and Tyr), oxidation (Met) and deamidation (Asn, Gln). Raw data files were converted to peptide maps comprising m/z values, charge state, retention time and intensity for all detected ions above a threshold of 30,000 counts. Using in-house software (Proteoprofile) (Granados et al. 2014), peptide maps corresponding to all identified peptide ions were aligned together to correlate their abundances across sample replicates. PEAKS decoy-fusion approach was used to calculate the false discovery rate of quantified unique peptide sequences. The highest scored MS/MS spectra of MHC class I peptides detected in at least one of the individuals were validated manually, using Xcalibur™ software version 2.2 SP1.48 (Thermo Scientific®).

Selection of MiHAs.

Peptides were filtered by their length and those peptides with the canonical MAP length (typically 8-14 mers) were kept. The predicted binding affinity ($IC_{50}$) of peptides to the allelic products was obtained using NetMHC version 3.4 (http://www.cbs.dtu.dk/services/NetMHC/, Lundegaard et al., 2008 (PMID: 18413329)). Peptides with an $IC_{50}$ below 5,000 nM were considered as HLA binders.

MiHAs were selected according to the following criteria:
i) Presence of a reported non-synonymous SNP (nsSNP) in the peptide-coding region (a total of 6,773 polymorphic peptides) of the individuals leading to surface expression of the corresponding peptide(s). These constitute MiHA differences between the individuals and other individuals harboring the alternate allele for the reported SNP.
ii) Unambiguous origin of the MiHA. Hence, the MiHA has a single genetic origin in the individual's genome.
iii) The MiHA does not derive from immunoglobulins or HLA class I or class II genes since these genes are highly polymorphic and very variable between individuals.
iv) The MiHA has a reported minor allele frequency (MAF) of at least 0.05 according to the dbSNP database build 138 (NCBI) and/or the NHLBI Exome Sequencing Project (ESP).

The RNA (cDNA) and DNA sequences encoding MiHAs were manually inspected using the Integrative Genomics Viewer v2.3.25 (The Broad Institute). The UCSC Repeat Masker track was included to discard candidates that corresponded to repetitive regions.

Determination of Allele Frequency.

The minor allele frequency (MAF) of each ns-SNP was obtained from the dbSNP database build 138 (NCBI) and/or the NHLBI Exome Sequencing Project (ESP). A definition of MAF can be found here: (http://www.ncbi.nlm.nih.gov/projects/SNP/docs/rs_attributes.html. Briefly, dbSNP is reporting the minor allele frequency for each rs included in a default global population. Since this is being provided to distinguish common polymorphism from rare variants, the MAF is actually the second most frequent allele value. In other words, if there are 3 alleles, with frequencies of 0.50, 0.49, and 0.01, the MAF will be reported as 0.49. The default global population is 1000Genome phase 1 genotype data from 1094 worldwide individuals, released in the May 2011 dataset.

MS/MS Validation of MiHA Sequences.

The highest scored MS/MS spectra of all candidate MiHAs detected in at least one of the individuals were validated manually, using Xcalibur™ software version 2.2 SP1.48 (Thermo Scientific®). MS/MS spectra of the selected MiHAs were further validated using synthetic MiHA versions synthesized by Genscript. Subsequently, 250-500 fmol of each peptide were injected in the LTQ-Orbitrap ELITE™ or the Q-Exactive™ Plus mass spectrometer using the same parameters as those used to analyze the biological samples.

Determination of the Tissue Distribution of Gene Expression.

Allogeneic T cells can react against a multitude of host MiHAs expressed elsewhere than in hematopoietic/lymphoid organs and induce GVHD. Therefore, to avoid GVHD MiHA expression should not be ubiquitous. Unfortunately, current technical limitations prevent from experimentally assessing MiHA expression in these tissues by mass spectrometry. As an alternative, it was previously shown that MAPs preferentially derive from abundant transcripts (Granados et al. Blood 2012). Thus, the level of expression of transcripts coding for MiHAs could be used as an indicator of MiHAs expression. Publicly available data from Fagerberg et al., *Mol Cell Proteomics* 2014 13: 397-406 were used, which is part of The Human Project Atlas (THPA) (http://www.proteinatlas.org/tissue, Uhlen et al (2010). *Nat Biotechnol.* 28(12):1248-50), listing the expression profiles of human genes for 27 tissues. From this data, the expression level of genes coding for the identified MiHAs was obtained. Genes were then classified as "ubiquitous" if expressed in 27 tissues with a "Fragments Per Kilobase of exons per Million mapped reads (FPKM)">10 or as "not ubiquitous" if not expressed with a FPKM>10 in all 27 tissues. Also, these data were used to calculate the ratio of MiHA genes expression in the bone marrow compared to the skin. Of note, the bone marrow samples used by from Fagerberg et al. (supra) were Ficoll™-separated preparations in which non-hematopoietic components of stroma, adipose cells, bone and vessels, as well as large portions of the fully differentiated erythropoietic and myelopoietic populations had been removed (http://www.proteinatlas.org/humanproteome/bone+marrow). Reads Per Kilobase per Million mapped reads (RPKM) values of MiHA-coding genes in AML samples were obtained from the TCGA Data Portal version 3.1.6. AML data included 128 samples of different subtypes: 12 M0, 36 M1, 29 M2, 12 M3, 23 M4, 14 M5, 2 not classified. Values were converted to $Log_{10}(1,000 \text{ RPKM}+1)$ for visualization purposes. Mean values were calculated using the 128 AMLs, expect for the Y chromosome-encoded UTY gene, for which only 65 male samples were considered.

Cumulative Number of Identified MiHAs Per Individual.

A custom software tool was used to estimate the cumulative number of HLA-A*02:01 or HLA-B*44:03-associated MiHAs expected for each additional individual studied. Since this number is influenced by the MiHAs present in each individual and by the order in which individuals are analyzed, we exhaustively listed the number of newly identified MiHAs expected for each additional individual studied in all combinations and permutations of groups of studied individuals. Then, we computed the average number of MiHAs for each number of studied individuals. To approximate the cumulative number of MiHAs for up to 20 individuals, a predictive curve was mapped on the data points. The curve was fitted on a function using the curve_fit tool from the "optimize" module of the "scipy" Python library (Jones E, Oliphant E, Peterson P, et al. SciPy: Open Source Scientific Tools for Python, 2001-, http://www.scipy.org/). The following equation was used to represent the cumulative number of identified MiHAs:

$$\frac{a \times x}{b + x}$$

Frequency of Therapeutic MiHA Mismatches.

In order to estimate the number of therapeutic MiHA mismatches, a bioinformatic simulation approach was used. For each ns-SNP encoding the 39 optimal MiHAs, the reported alleles were retrieved from the European-American population of the Exome Sequencing Project (ESP) or, if not available, from the European population of "The 1,000 Genomes Project" (http://www.1000genomes.org/). Next, the alleles were categorized from a peptide perspective as 'dominant' if the MiHA was detected by MS or known to be immunogenic, or as 'recessive' if the MiHA was neither detected by MS nor shown to be immunogenic. Of note, in some loci both alleles were codominant. It was assumed that the presence of a dominant allele always leads to the surface expression of the MiHA. In the case of overlapping MiHAs deriving from the same ns-SNP, the MiHA locus was considered only once. In this simulation, it was also assumed that MiHA-coding SNPs are independent events. In the case of Y chromosome-derived MiHAs (absent in females), a therapeutic mismatch occurred in all male recipient/female donor pairs. Based on the reported minor allele frequencies (MAFs), the allele frequency of the 'dominant' or of the 'recessive' MiHA was determined in all MiHA-coding loci. Assuming a female/male ratio of 1:1, $1 \times 10^6$ unrelated donor/recipient pairs were randomly generated and virtually genotyped using increasing subsets (1 to 30) of this ranked list of MiHAs. Thus, one population was generated for each MiHA subset. The MAF of each MiHA was used as a probability to generate each individual's maternal and paternal MiHA alleles. For each MiHA subset tested, this procedure resulted in two sets of MiHA alleles (or MiHAs haplotypes) per individual. The number of MiHA mismatches found in each pair was determined and if at least one mismatch was achieved, a therapeutic mismatch was called. The same procedure was used for the related pairs, except that the sampling population corresponded to the progeny of a parental population and was generated according to Mendelian inheritance. This procedure was repeated $1 \times 10^6$ times for both related and unrelated pairs.

Statistical Analyses and Data Visualization.

Unless otherwise stated, analyses and figures were performed using the RStudio™ version 0.98.1091, R version 3.1.2 and Prism™ version 5.0d software. The Wilcoxon rank sum test was used to compare the polymorphic index distribution of exons and exon-exon junctions, or of MiHA-coding genes and that of genes coding for non-polymorphic MAPs. The gplots package in R was used to perform hierarchical clustering and heatmaps of MiHA genes expression in different AML subtypes. Mean expression of MiHA genes among AML subtypes was compared using ANOVA followed by Tukey's multiple-comparison test.

Determination of the Immunogenicity of the Identified MiHAs.

T cells and monocytes were purified from $100-150 \times 10^6$ PBMCs obtained from MiHA-negative individuals using MACS® cell separation columns (Miltenyi Biotec®) or EasySep™ kits (Stemcell Technologies®). Monocyte-derived dendritic cells were generated as previously described (3) and matured with GM-CSF, IL-4, $PGE_2$, TNFα, IL-1β, IL-6 and IFNγ. These dendritic cells were then irradiated at 40 Gy and pulsed with 2 μg/mL of the synthetic MiHA peptide (GLRX3-1$^S$, WDR27-1$^L$, MIIP-2$^E$, or RASSF1-1$^S$) or an irrelevant peptide (Epstein-Barr virus LMP2$^{426-434}$) that was used a negative control. Pulsed or unpulsed dendritic cells were then co-cultured with previously enriched autologous T cells ($5 \times 10^5$/well) in 48-well plates in advanced RPMI medium supplemented with 10% of human serum, 1% of L-Glutamine and 30 ng/mL of IL-21 at a 1:4 (stimulator:effector) ratio. Supplemented media with IL-7 and IL-15 was added after 3, 5 and 7 days of culture and cells were transferred in 12-well plates and 6-well plates at day 5 and 7, respectively. After 10 days of culture, T cells were harvested to determine antigen reactivity with ELISpot for IFNγ and polyfunctional intracellular cytokine staining. Briefly, ELISpot analysis was performed according to the manufacturer's instructions (MABtech®) and intracellular staining was performed after restimulation with 5 μg/mL of peptide in the presence of Brefeldin A for 4 hours. Subsequently, cells were stained for CD3 and CD8 surface markers, and with antibodies directed against the following cytokines for intracellular staining (obtained from BD Biosciences®): IFNγ (Ab 4S.B3), IL-2 (Ab MQ1-17H12), TNFα (Ab MAb11), for intracellular staining. Acquisition was performed with a BD™ LSR II flow cytometer and data were analyzed using Flowlogic™ software (Inivai Technologies®).

Example 2: Identification and Characterization of Novel Human MiHAs

A MiHA is essentially a MAP coded by a genomic region containing an ns-SNP.[13,21] All human MiHAs discovered to date derive from bi-allelic loci with either two co-dominant alleles or one dominant and one recessive allele.[21,26] Indeed, an ns-SNP in a MAP-coding sequence will either hinder MAP generation or generate a variant MAP.[11] Hence, at the peptidomic level, each allele can be dominant (generate a MAP) or recessive (a null allele that generates no MAP). All MiHAs reported in this work were detected by MS and are therefore coded by dominant alleles. It was reasoned that two features should dictate which of these MiHAs may represent adequate targets for immunotherapy of HCs. First, the usefulness of a MiHA is determined by the allelic frequency of the MiHA-coding ns-SNP. Indeed, in order to be recognized by allogeneic T cells, a MiHA must be present on host cells and absent in donor cells (otherwise, donor T cells would not recognize the MiHA as non-self). This situation is referred to as a "therapeutic mismatch". The probability to have a therapeutic mismatch is maximal when the allelic frequency of the target MiHA is 0.5 and decreases as the allele frequency approaches the two extremes of 0 and 1.[14] Thus, MiHA having an allele frequency of 0.01 or 0.99 would yield a low frequency of therapeutic mismatch: in the first case, MiHA-positive recipients would be rare whereas in the second case, MiHA-negative donors would be difficult to find. As a rule only variants with a MAF≥0.05 are considered as common and balanced genetic polymorphisms.[33] Thus, all MiHAs coded by loci whose least common (minor) allele had a frequency<0.05 were excluded from further analyses. Second, the tissue distribution of a MiHA is relevant to both the efficacy and the innocuity of MiHA targeting. For HC immunotherapy, the target MiHA must be expressed in hematopoietic cells (including HC cells) but should not be ubiquitously expressed by host tissues.

Figure 2A:
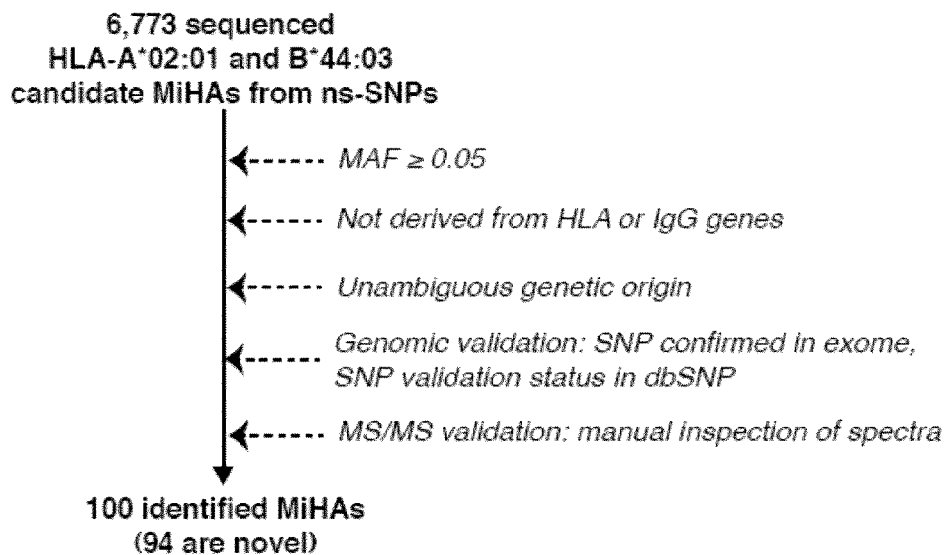
FIGS. 2A and 2B show the validation steps and filtering criteria applied to select and prioritize the Novel MiHAs.

Proteogenomic analyses were performed on B lymphoblastoid cell lines (BLCLs) from 13 individuals expressing HLA-A*02:01 and/or HLA-B*44:03 allotypes. About 55% of European Americans express at least one of these two allotypes. Whole exome and transcriptome sequencing was performed for each cell line in order to identify ns-SNPs and then in silico translated the genomic sequences to create personalized proteomes. Each proteome was subsequently used as a reference to sequence the individual-specific repertoire of MAPs by high-throughput MS.[26] A total of 6,773 MiHA candidates generated by ns-SNPs were identified by MS. However, 96.2% of these ns-SNPs were of limited clinical interest because they were rare variants with a MAF<0.05 (FIG. 1A). Further analyses focused on common variants, with a MAF≥0.05.[33] After filtering and manual MS validation, a total of 100 high-frequency MiHAs were identified (Methods, FIG. 2A and Table II), of which 93 were novel (in white in Table II). In addition, the MS/MS spectra of the most common MiHAs were confirmed using synthetic versions of the peptides.

TABLE II

Features of MIHAs identified in the studies described herein

| Name | Sequence[1] | HLA SNP_ID | Ensembl gene ID | SEQ ID NO: |
|---|---|---|---|---|
| ANKRD13A-1L/P | SLLESSRSQEL/P | A0201rs2287174 | ENSG00000076513 | 79-81 |
| ANXA2-1V/L | ALSGHLETV/L | A0201rs17845226 | ENSG00000182718 | 82-84 |
| APOL1-1I/M | QELEEKLNI/ML | B4403rs60910145 | ENSG00000100342 | 85-87 |
| ARL2-1V/A | REV/ALELDSI | B4403rs664226 | ENSG00000213465 | 88-90 |
| ASCC2-1R/Q | R/QLAPTLSQL | A0201rs4823054 | ENSG00000100325 | 91-93 |
| BCS1L-1D/N | QEFID/NNPKW | B4403rs58447305 | ENSG00000074582 | 94-96 |
| BLM-1V/I | EEIPV/ISSHY | B4403rs7167216 | ENSG00000197299 | 10-12 |
| BLM-2V/I | EEIPV/ISSHYF | B4403rs7167216 | ENSG00000197299 | 13-15 |
| BOLA1-1G/A | AEELG/AGPVHAL | B4403rs1044808 | ENSG00000178096 | 97-99 |
| CCDC34-1E/A | AE/AIQEKKEI | B4403rs17244028 | ENSG00000109881 | 16-18 |
| CCPG1-A/G | SESEDRLVA/G | B4403rs117236526 | ENSG00000260916 | 100-102 |
| CCT3-1L/F | ILSEVERNL/F | A0201rs2230194 | ENSG00000163468 | 103-105 |
| CCT3-2I/V | EENGRKEIDI/VKKY | B4403rs11548200 | ENSG00000163468 | 106-108 |
| CENPF-1 NQ/DQ/NH/DH | QEN/DIQ/HNLQL | B4403rs3748692 | ENSG00000117724 | 19-23 |
| CENPF-1 NQ/DQ/NH/DH | QEN/DIQ/HNLQL | B4403rs3748693 | ENSG00000117724 | 19-23 |
| CEP55-1R/K | QEEQTR/KVAL | B4403rs75139274 | ENSG00000138180 | 109-111 |
| COMMD10-1I/S | I/SLAPCKLETV | A0201rs1129495 | ENSG00000145781 | 112-114 |
| COMMD10-1I/S | S/ILAPCKLETV | A0201rs1129495 | ENSG00000145781 | 112-114 |
| COPE-1T/I | RSVDVTNT/ITFL | A0201rs10330 | ENSG00000105669 | 115-117 |
| CPOX-1N/H | VEEADGN/HKQW | B4403rs1131857 | ENSG00000080819 | 24-26 |
| CPOX-2N/H | EEADGN/HKQWW | B4403rs1131857 | ENSG00000080819 | 27-29 |
| DCXR-1A/T | AEVEHVVNA/T | B4403rs61746217 | ENSG00000169738 | 118-120 |
| DNAH8-1A/T | KEIA/TKTVLI | B4403rs1678674 | ENSG00000124721 | 121-123 |
| DYNC2LI1-1L/I | KL/IRGVINQL | A0201rs11556157 | ENSG00000138036 | 124-126 |
| DYNC2LI1-1L/I | KI/LRGVINQL | A0201rs11556157 | ENSG00000138036 | 124-126 |
| ERAP1-2E/Q | MLRSE/QLLL | A0201rs27044 | ENSG00000164307 | 127-129 |
| GEMIN4-1Q/E | RQ/EPDLVLRL | A0201rs2740348 | ENSG00000179409 | 130-132 |
| GM2A-1A/T | LLLAA/TPAQA | A0201rs1048719 | ENSG00000196743 | 133-135 |
| HERC3-1E/Q | E/QETAIYKGDY | B4403rs1804080 | ENSG00000138641 | 136-138 |
| HEXB-1/V | LI/VDTSRHYL | A0201rs10805890 | ENSG00000049860 | 139-141 |
| HJURP-1E/G | EE/GRGENTSY | B4403rs10511 | ENSG00000123485 | 30-32 |
| HMMR-2R/C | KILEKEIR/CV | A0201rs299284 | ENSG00000072571 | 1-3 |

TABLE II-continued

Features of MIHAs identified in the studies described herein

| Name | Sequence[1] | HLA SNP_ID | Ensembl gene ID | SEQ ID NO: |
|---|---|---|---|---|
| HMMR-3R/C | SESKIR/CVLL | B4403rs299284 | ENSG00000072571 | 33-35 |
| HY-KDM5D-1 | VEVPEAHQL or absent[2] | B4403Y-linked | ENSG00000012817 | 142 |
| HY-UTY-2 | NESNTQKTY or absent[2] | B4403Y-linked | ENSG00000183878 | 36 |
| IKBKAP-1I/M | MESI/MNPHKY | B4403rs2230794 | ENSG00000070061 | 143-145 |
| KIF20B-1I/N | QELETSI/NKKI | B4403rs12572012 | ENSG00000138182 | 146-148 |
| LARS-1N/D | N/DEVLIHSSQY | B4403rs61732383 | ENSG00000133706 | 149-151 |
| MCPH1-R/I | EEINLR/INI | B4403rs2083914 | ENSG00000147316 | 37-39 |
| MIIP-1K/E | SEESAVPK/ERSW | B4403rs2295283 | ENSG00000116691 | 40-42 |
| MIIP-1K/E | SEESAVPE/KRSW | B4403rs2295283 | ENSG00000116691 | 40-42 |
| MIIP-2K/E | EESAVPE/KRSW | B4403rs2295283 | ENSG00000116691 | 43-45 |
| MIIP-2K/E | EESAVPK/ERSW | B4403rs2295283 | ENSG00000116691 | 43-45 |
| MIS18BP1-1E/D | QE/DLIGKKEY | B4403rs34101857 | ENSG00000129534 | 46-48 |
| MKI67-1G/S | EELLAVG/SKF | B4403rs2152143 | ENSG00000148773 | 49-51 |
| MKI67-1G/S | EELLAVS/GKF | B4403rs2152143 | ENSG00000148773 | 49-51 |
| MKI67-2D/G | GED/GKGIKAL | B4403rs10082391 | ENSG00000148773 | 52-54 |
| MKNK2-1Q/K | AELQ/KGFHRSF | B4403rs3746101 | ENSG00000099875 | 152-154 |
| NDC80-1A/P | HLEEQIA/PKV | A0201rs9051 | ENSG00000080986 | 4-6 |
| NDC80-1A/P | HLEEQIP/AKV | A0201rs9051 | ENSG00000080986 | 4-6 |
| NMRAL1-1T/I | T/ILLEDGTFKV | A0201rs11557236 | ENSG00000153406 | 155-157 |
| NMRAL1-1T/I | I/TLLEDGTFKV | A0201rs11557236 | ENSG00000153406 | 155-157 |
| NOP56-1I/V | VIAEI/VLRGV | A0201rs2273137 | ENSG00000101361 | 158-160 |
| NOP56-2I/V | AEI/VLRGVRL | B4403rs2273137 | ENSG00000101361 | 263-265 |
| NUP62-1D/E | KLAENID/EAQL | A0201rs892028 | ENSG00000213024 | 161-163 |
| NUP62-2D/E | AENID/EAQLKRM | B4403rs892028 | ENSG00000213024 | 164-166 |
| PARP4-1A/T | FLQAKQIA/TL | A0201rs2275660 | ENSG00000102699 | 167-169 |
| PARP4-2T/I/R | DEIVCT/I/RQHW | B4403rs1372085 | ENSG00000102699 | 170-173 |
| PASK-1F/C | YTWEEVF/CRV | A0201rs1131293 | ENSG00000115687 | 174-176 |
| PFN1-1L/M/V | KTDKTLVL/M/VL | A0201rs13204 | ENSG00000108518 | 177-180 |
| PML-1A/P | SQVQVPLEA/P | A0201rs743582 | ENSG00000140464 | 181-183 |
| POC5-1H/R | EEYEELLH/RY | B4403rs2307111 | ENSG00000152359 | 184-186 |
| POC5-1H/R | EEYEELLR/HY | B4403rs2307111 | ENSG00000152359 | 184-186 |
| POLR2L-1D/E | TEGD/EALDALGLKRY | B4403rs4895 | ENSG00000177700 | 187-189 |
| PPP1CB-1Q/H | GQ/HYTDLLRL | A0201rs1128416 | ENSG00000213639 | 190-192 |
| PREX1-1H/Q | EEALGLYH/QW | B4403rs41283558 | ENSG00000124126 | 55-57 |
| PRKCD-1E/D | GE/DYFAIKAL | B4403rs2230494 | ENSG00000163932 | 193-195 |
| PRMT1-1E/K | IE/KDRQYKDY | B4403rs187325799 | ENSG00000126457 | 196-198 |

TABLE II-continued

Features of MIHAs identified in the studies described herein

| Name | Sequence[1] | HLA SNP_ID | Ensembl gene ID | SEQ ID NO: |
|---|---|---|---|---|
| R3HCC1-1H/R | AENDFVH/RRI | B4403rs11546682 | ENSG00000104679 | 199-201 |
| RASSF1-1A/S | A/SEIEQKIKEY | B4403rs2073498 | ENSG00000068028 | 7-9 |
| RASSF1-1A/S | S/AEIEQKIKEY | B4403rs2073498 | ENSG00000068028 | 7-9 |
| RASSF1-2A/S | SQA/SEIEQKI | A0201rs2073498 | ENSG00000068028 | 58-60 |
| RNF213-1L/V | RL/VLQEQHQL | A0201rs61745599 | ENSG00000173821 | 202-204 |
| RRBP1-1R/L | R/LLQEELEKL | A0201rs1132274 | ENSG00000125844 | 205-207 |
| SCFD2-1L/S | GL/SSPLLQKI | A0201rs7675987 | ENSG00000184178 | 208-210 |
| SERF2-1S/P | TEMEIS/PRAA | B4403rs12702 | ENSG00000242028 | 61-63 |
| SFI1-1Q/R | EQ/RQLLYRSW | B4403rs2006771 | ENSG00000198089 | 211-213 |
| SMC4-1N/S | KEINEKSN/SIL | B4403rs33999879 | ENSG00000113810 | 64-66 |
| TAP1-1D/G | TEVD/GEAGSQL | B4403rs1135216 | ENSG00000168394 | 214-216 |
| TDP2-1Q/E | Q/EEAPESATVIF | B4403rs2294689 | ENSG00000111802 | 217-219 |
| TESPA1-1E/K | EE/KEQSQSRW | B4403rs997173 | ENSG00000135426 | 67-69 |
| TMSB10-1E/D | TETQE/DKNTL | B4403rs7148 | ENSG00000034510 | 220-222 |
| TPR-1V/I | AEV/IRAENL | B4403rs61744267 | ENSG00000047410 | 223-225 |
| TRAPPC5-1S/A | AELQS/ARLAA | B4403rs6952 | ENSG00000181029 | 70-72 |
| TRBV6-4I/T | LLWAGPVI/TA | A0201rs361437 | ENSG00000211713 | 226-228 |
| TRIM22-1N/D | KEN/DQEAEKL | B4403rs7935564 | ENSG00000132274 | 229-231 |
| TRIM5-1Q/R | Q/REYQVKLQA | B4403rs10838525 | ENSG00000132256 | 232-234 |
| TRIM5-1Q/R | R/QEYQVKLQA | B4403rs10838525 | ENSG00000132256 | 232-234 |
| TRMT12-1L/M/V | L/M/VEADLPRSW | B4403rs11556913 | ENSG00000183665 | 235-238 |
| TROAP-1R/G | QENQDPR/GRW | B4403rs8285 | ENSG00000135451 | 73-75 |
| TTI2-1G/E | IEATG/EFDRL | B4403rs2304748 | ENSG00000129696 | 239-241 |
| WDR27-1L/P | SL/PDDHVVAV | A0201rs4236176 | ENSG00000184465 | 242-244 |
| ZNF417-1H/R | QEPFVFH/REF | B4403rs201944488 | ENSG00000060237 | 245-247 |
| ZWINT-1G/R | QELDG/RVFQKL | B4403rs2241666 | ENSG00000122952 | 76-78 |
| ZWINT-1G/R | QELDR/GVFQKL | B4403rs2241666 | ENSG00000122952 | 76-78 |
| ACC-2D (BCL2A1) | KEFEDG/DIINW | B4403rs3826007 | ENSG00000140379 | 248-250 |
| ACC-2G (BCL2A1) | KEFEDD/GIINW | B4403rs3826007 | ENSG00000140379 | 248-250 |
| BCL2A1-1N/K | VLQN/KVAFSV | A0201rs1138358 | ENSG00000140379 | 251-253 |
| GLRX3-1S/P | FLS/PSANEHL | A0201rs2274217 | ENSG00000108010 | 254-256 |

TABLE II-continued

Features of MIHAs identified in the studies described herein

| Name | Sequence[1] | HLA SNP_ID | Ensembl gene ID | SEQ ID NO: |
|---|---|---|---|---|
| HMMR-1V/A | SLQEKV/AAKA | A0201rs299295 | ENSG00000072571 | 257-259 |
| WNK1-1I/M | TLSPEI/MITV | A0201rs12828016 | ENSG00000060237 | 260-262 |

[1] The residues in bold and separated by "/" indicate the amino acid variation(s) present in the MiHA.
[2] The genes from which these MiHAs are derived are located on chromosome Y. Accordingly, this MiHa is present in male but absent in female individuals.
[3] For the MiHAs derived from genes located on chromosome Y, the positions indicated correspond to the position of the first residue of the peptide in the protein, or the position of the first nucleotide encoding the first residue of the peptide in the transcript.

Figure 3A:
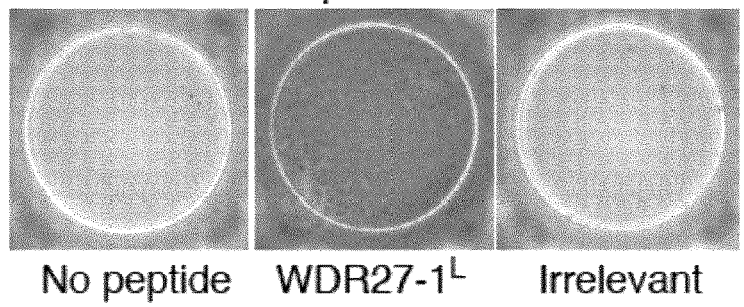
FIGS. 3A to 3D show the immunogenicity of the newly discovered MiHAs. T lymphocytes were primed against four newly discovered lead MiHAs: GLRX3-1$^S$, MIIP-2$^E$, RASSF1-1$^S$ and WDR27-1$^L$. After priming and expansion, T cells were re-exposed to no peptide, the MiHA targeted or an irrelevant peptide (HLA-A*02:01 restricted Epstein-Barr virus LMP2$^{426-434}$ peptide).
Figure 3B:
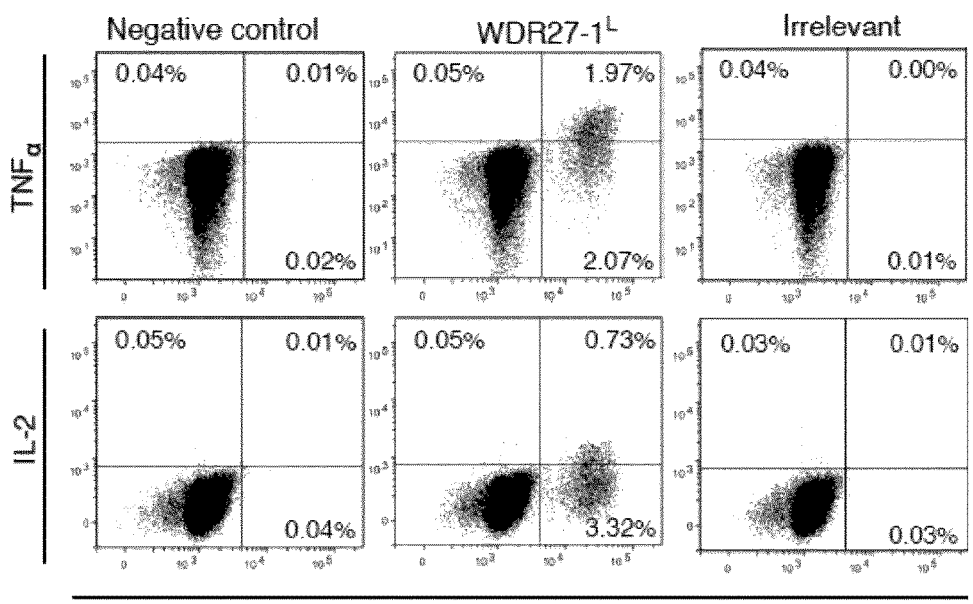
Figure 3C:
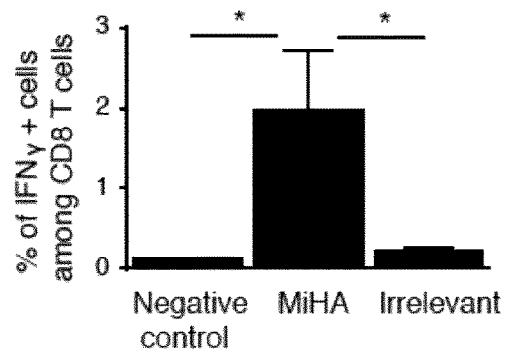
Figure 3D:
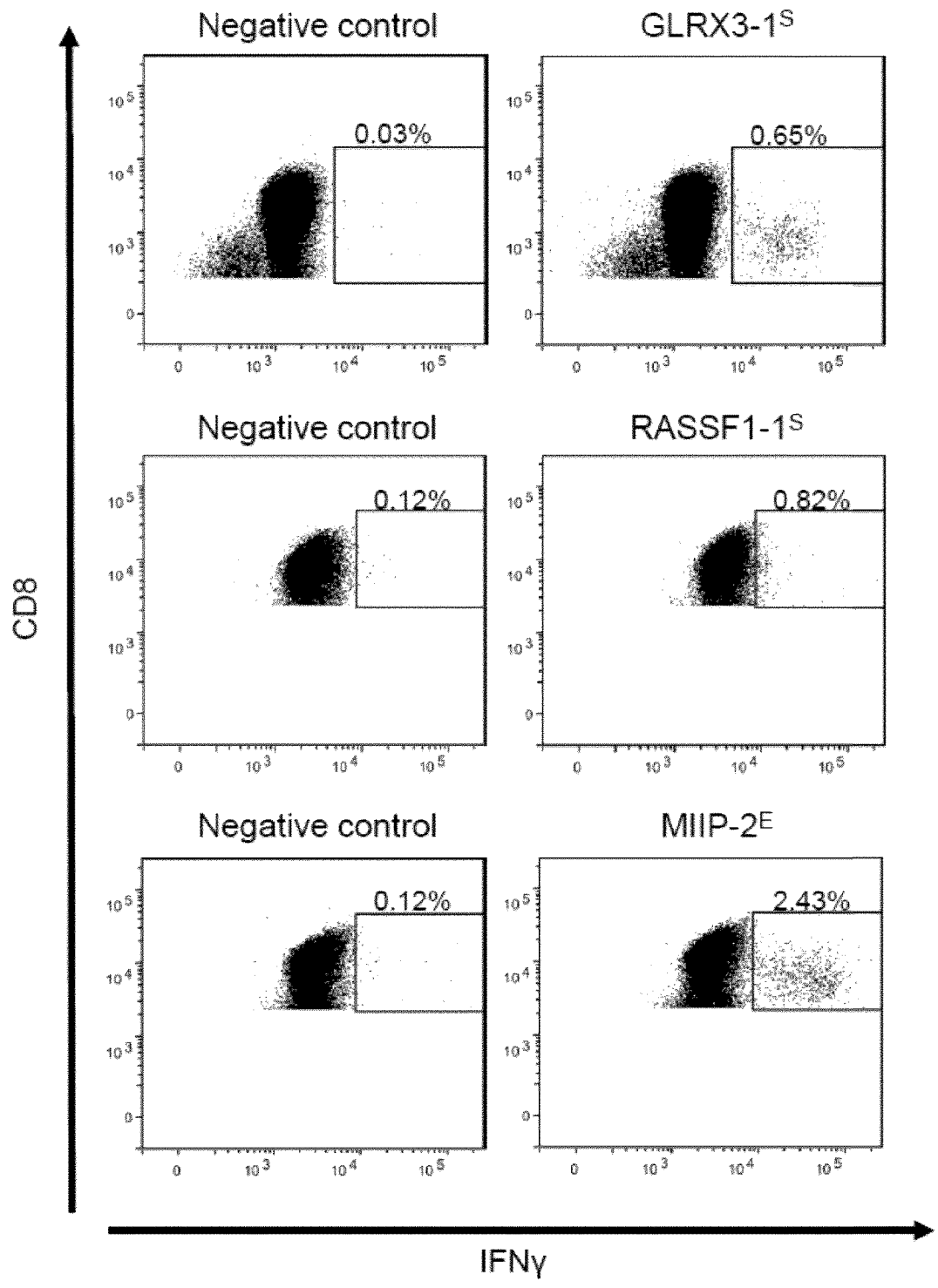

As a proof of principle, the immunogenicity of four novel MiHAs was tested: GLRX3-1$^S$, MIIP-2$^E$, RASSF1-1$^S$ and WDR27-1$^L$ (FIGS. 3A-3D). T cells from four MiHA-negative individuals were primed with autologous dendritic cells pulsed with either a synthetic MiHA or an irrelevant peptide. Read-out of antigen-reactivity was assessed by ELISpot (FIG. 3A) and intracellular staining assays (FIGS. 3B-3D). Primed T cells produced cytokines in a MiHA-specific fashion in all tested donors, confirming that the MiHAs are able to amplify/activate CD8$^+$ T lymphocytes.

Figure 1B:
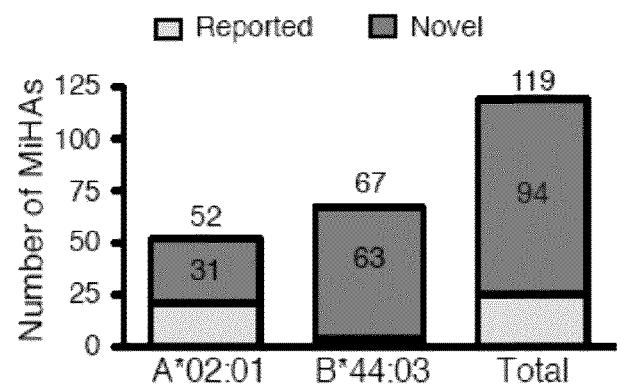
Figure 1C:
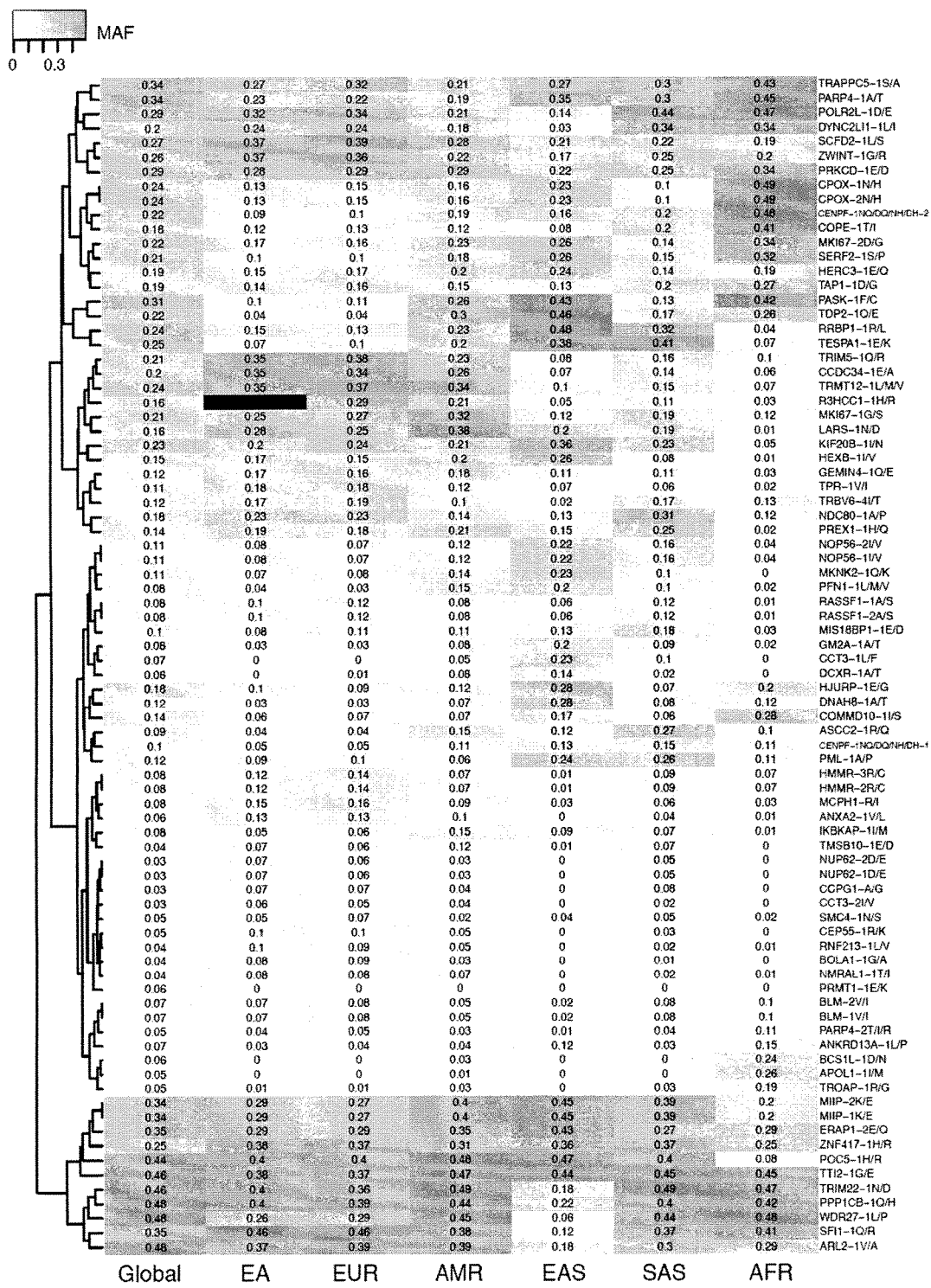
Figure 4A:
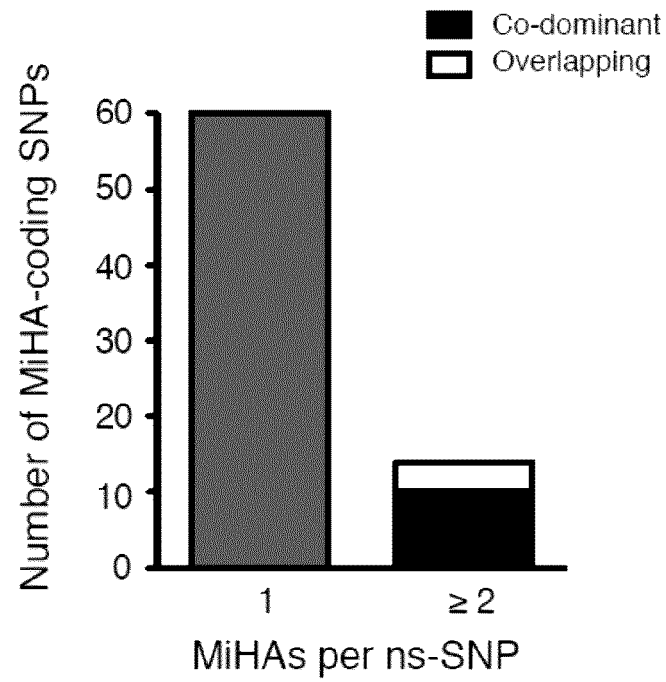
FIGS. 4A to 4E show features of MiHAs associated to HLA-A*02:01 and HLA-B*44:03.
Figure 4B:
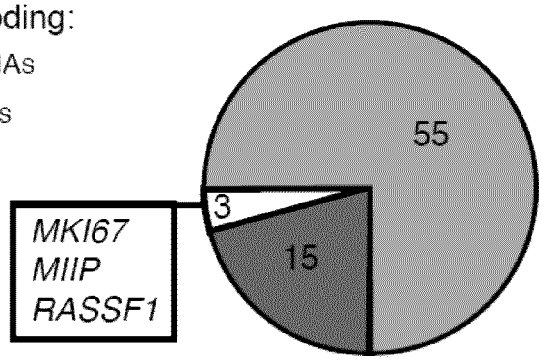
Figure 4C:
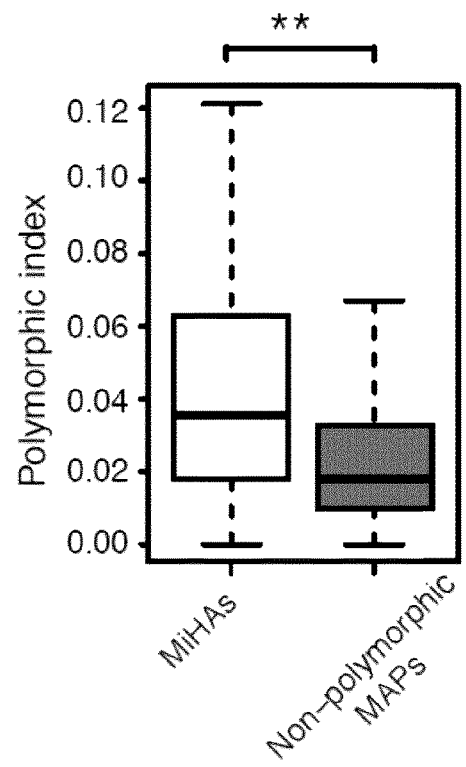
Figure 4D:
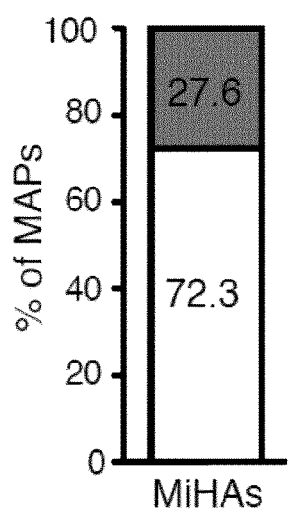
Figure 4E:
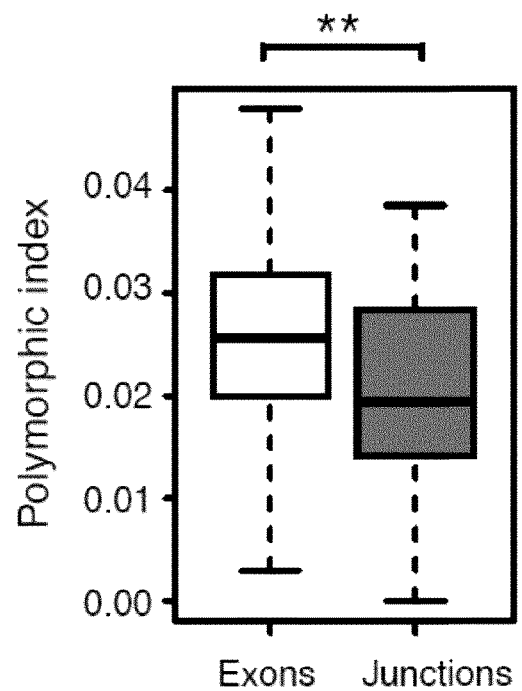

Previous MiHA discovery efforts have largely focused on HLA-A*02:01 and to a lesser extent on HLA-B*44:03.[14,24,34] The proteogenomic approach used herein increased the total number of MiHAs presented by HLA-A*02:01 from 21 to 52, and by HLA-B*44:03 from 4 to 67 (FIG. 1B). Although some ns-SNPs generating the 94 novel MiHAs have similar MAFs in different populations, the MAF of several ns-SNPs is variable from one population to another (FIG. 1C). From a global perspective, these results mean that most of the MiHAs that were discovered in individuals of European American origin could also be used to treat patients from other populations including Africans and Asians. Previous studies on small sets of MiHAs have shown that for most MiHA loci, one (dominant) allele generates a MiHA while the other (recessive) allele does not generate a MiHA.[21,26] The large MiHA dataset (94 MiHAs coded by 73 genes) confirms and extends this observation: most MiHA-coding ns-SNPs generated a single MiHA variant (FIG. 4A). Notably, 18 genes were of particular interest as they generated more than one MiHA (FIG. 4B). A logical inference would be that MiHA-coding genes display a high degree of genetic polymorphism. In line with this, it was found that MiHA-coding genes have a higher ns-SNP density than genes coding invariant HLA class I peptides (FIG. 4C). Also, about 72% of MiHAs arose from a single exon as opposed to exon-exon junctions (i.e., from two neighboring exons) (FIG. 4D). This result reflects the intragenic ns-SNP distribution, since in MiHA-coding genes the density of ns-SNPs is significantly greater in the center of exons than in regions close to junctions (FIG. 4E).

Figure 5A:
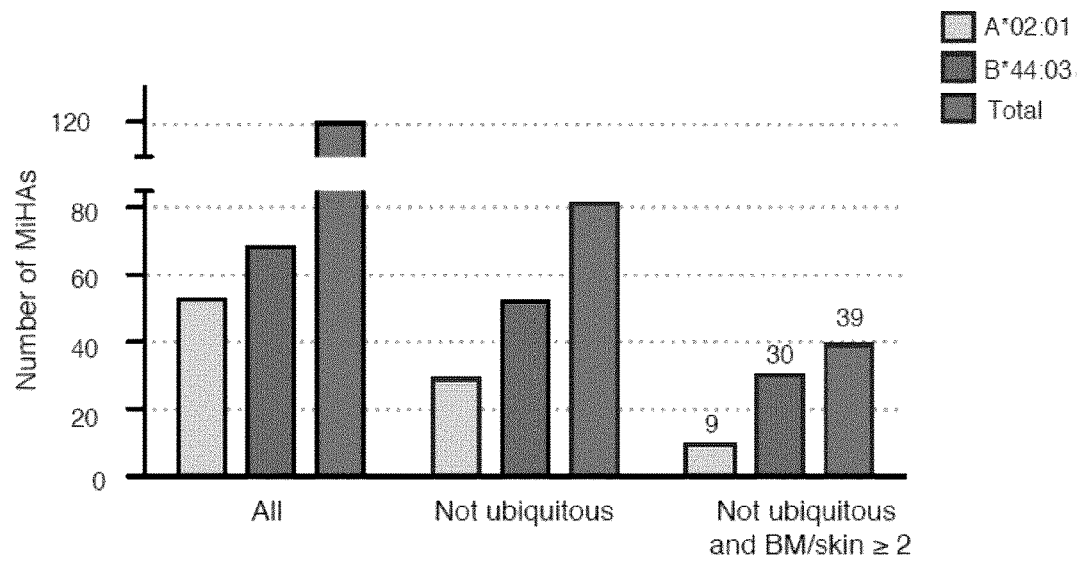
FIG. 5A shows the number of MiHAs selected according to their gene expression pattern. Expression levels of genes from which derive the previously reported (n=7)[24,34] and novel MiHAs (n=32) with a MAF 0.05, were retrieved from the study of Fagerberg and colleagues.[30] MiHAs were classified as ubiquitous if expressed in 27 tissues with >10 FPKM.[30] A ratio of bone marrow (BM) over skin ≥2 was further considered to select MiHA-coding transcripts that are enriched in hematopoietic cells. Left bars: MiHAs associated to HLA-A*02:01; middle bars: MiHAs associated to HLA-B*44:03; right bars: total.

Example 3: MiHAs Coded by Genes Preferentially Expressed in Hematopoietic Cells It was assumed that, for HC immunotherapy, optimal MiHAs should be expressed on hematopoietic cells, including the target HC cells, but should ideally not be ubiquitously expressed. Indeed, ubiquitous expression decreases the efficacy of immunotherapy by causing exhaustion of MiHA-specific T cells and entails the risk of toxicity toward normal host epithelial cells (Graft-versus-Host-Disease, GvHD). Since the abundance of a MAP shows a good correlation with the abundance of its source transcript,[22,38-40] and RNA-Seq is currently the most accurate method for evaluation of transcript abundance, the expression level of MiHA-coding transcripts was evaluated by RNA-Seq. No RNA-Seq data are available for purified primary epithelial cells from all anatomic sites, but this information is available for entire tissues and organs. Publicly available RNA-Seq data on 27 human tissues from different individuals[30] were therefore used to assess the expression profile of genes coding the 119 high-frequency MiHAs presented by the HLA-A*02:01;B*44:03 haplotype (94 reported herein and 25 previously reported) (FIG. 5A). The list of previously reported MiHAs is provided in Table III below.

TABLE III

List of previously reported MiHAs analyzed in the present study

| MiHA name | Sequence | SEQ ID No: |
|---|---|---|
| ACC-2G (BCL2A1)* | KEFEDD/GIINW | 248 |
| BCL2A1-1N/K* | VLQN/KVAFSV | 251 |
| C19orf48 | CIPPDS/TLLFPA | 266 |
| FAM119 | AMLERQFT/IV | 267 |
| GLRX3-1S/P* | FLS/PSANEHL | 254 |
| HA-1H/R | VLH/RDDLLEA | 268 |
| HA-2V/M | YIGEVLVSV/M | 269 |
| HA-8 | R/PTLDKVLEV | 270 |
| HB-1H | EEKRGSLH/YVW | 271 |
| HB-1Y | EEKRGSLY/HVW | 271 |
| HMMR-1V/A* | SLQEKV/AAKA | 257 |
| HNF4G | MM/IYKDILLL | 272 |
| HY-A2 | FIDSYICQV or absent | 273 |
| LB-NISCH-1A | ALAPAPA/VEV | 274 |
| LB-PRCP-1D | FMWDVAED/EL | 275 |

TABLE III-continued

List of previously reported MiHAs analyzed in the present study

| MiHA name | Sequence | SEQ ID No: |
|---|---|---|
| LB-PRCP-1D | FMWDVAED/ELKA | 276 |
| LB-SSR1-1S | S/LLAVAQDLT | 277 |
| LB-SSR1-1S | VLFRGGPRGS/LLAVA | 278 |
| LB-WNK1-1I | RTLSPEI/MITV | 279 |
| MYO19 | RLLEAIIRL/F | 280 |
| PARP10 | GL/PLGQEGLVEI | 281 |
| SSR1-1L | VLFRGGPRGL/SLAVA | 282 |
| T4A | GLYTYWSAGA/E | 283 |
| UTA2-1 | QLL/PNSVLTL | 284 |
| WNK1-1I/M* | TLSPEI/MITV | 260 |

*detected in the present study (see Table II above)

Figure 2B:
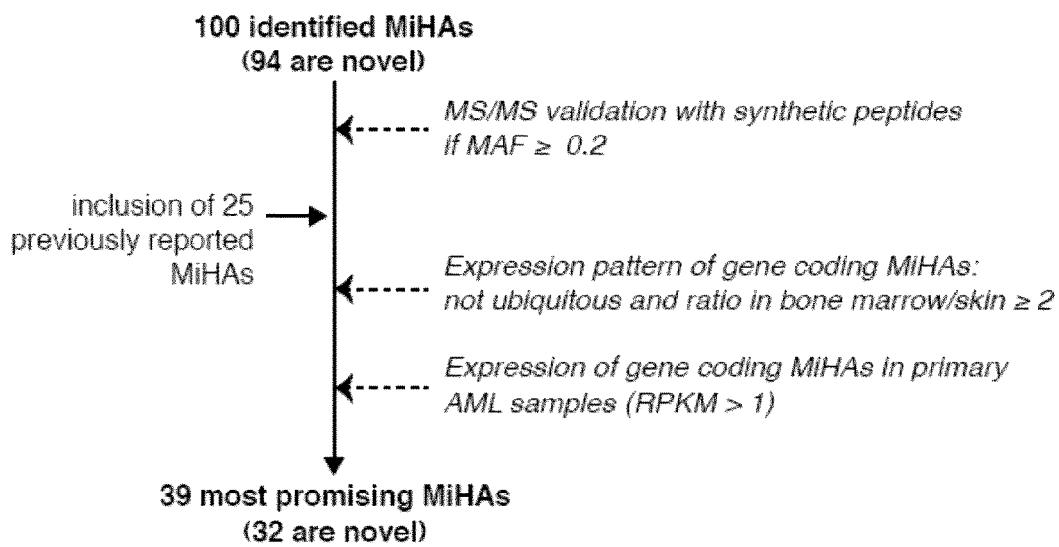

To evaluate the relative expression of MiHA-coding genes in hematopoietic vs. epithelial cells, RNA-Seq data obtained from bone marrow vs. skin cells were used. Skin cells are not a pure population of epithelial cells (they contain cells of monocytic and dendritic cell lineage), but are nevertheless highly enriched in epithelial relative to hematopoietic cells. As a criterion for preferential expression in hematopoietic cells, an expression ratio 2 in the bone marrow relative to the skin was used. Out of 119 MiHAs, 39 (32.8%) were non-ubiquitous and overexpressed in hematopoietic cells (FIG. 5A and FIG. 2B).

Figure 5B:
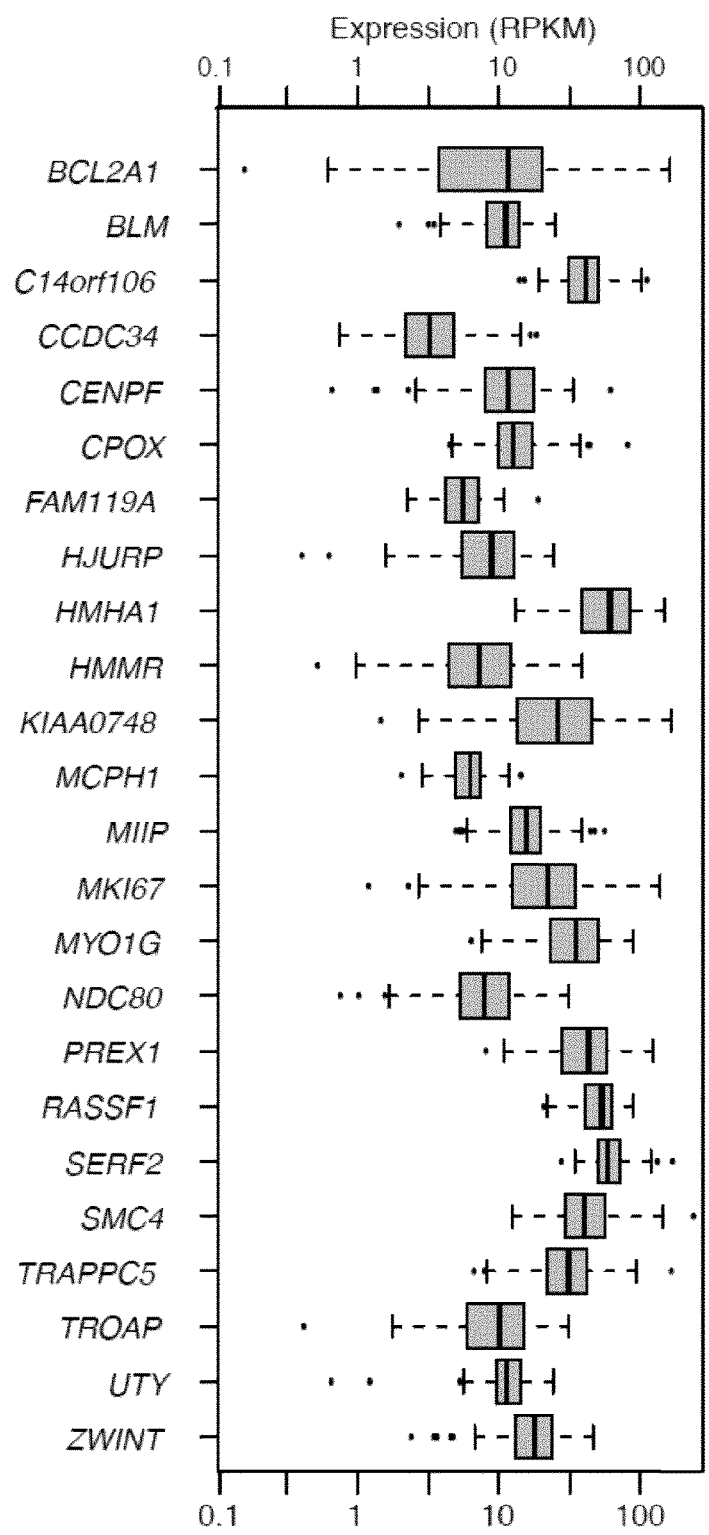
FIG. 5B: All genes coding the MiHAs of most clinical interest are expressed in primary acute myeloid leukemia (AML) samples. RPKM expression in 128 AML samples was obtained from TCGA. Boxplots show the expression distribution of each MiHA gene (expression displayed in $Log_{10}$) scale) in AMLs. The middle line of box plot indicates the median. Because the UTY gene is on the Y chromosome, it is expressed only in males.
Figure 5C:
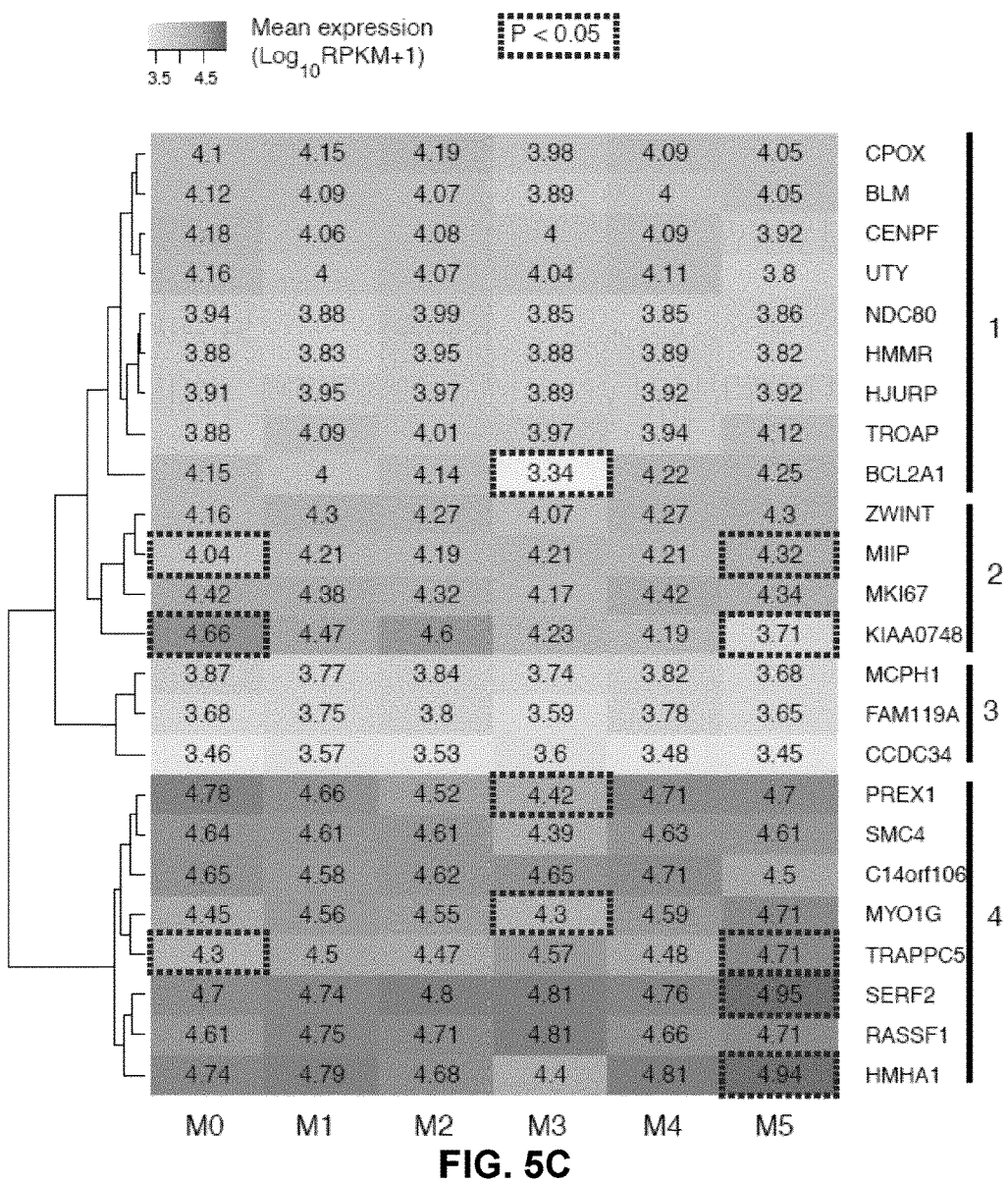
FIG. 5C: Hierarchical clustering and heatmap showing mean expression values of MiHA genes in various AML subtypes. Values were converted to $Log_{10}(1,000 RPKM+1)$ for visualization purposes. MiHA gene expression in AMLs was obtained from the TCGA and analyzed as in b. AML subtypes correspond to the French-American-British classification. Numbers 1-4 on the rightmost side of the panel identify gene clusters. Nine MiHA genes that are differentially expressed AML subtypes are shown in bold (ANOVA, P<0.05), and AML subtypes showing a peculiar gene expression pattern are marked with dashed outlines (Tukey test, P<0.05).

Acute myeloid leukemia (AML) is the most common indication for AHCT according to the Center for International Blood and Marrow Transplant Research (CIBMTR, http://www.cibmtr.org). The expression of genes coding the most promising MiHAs in AML cells was thus analyzed using RNA-Seq data from 128 AML samples available from The Cancer Genome Atlas (TCGA) (FIG. 5B). It was found that the 24 genes coding for the 39 optimal MiHAs were all expressed in AML. Features of the novel lead MiHAs are shown in Table IV. The seven (7) other lead MiHAs identified among the 25 previously reported MiHAs are depicted in Table V. Hierarchical clustering revealed that MiHA genes could be classified in 4 major clusters according to their expression in AMLs (FIG. 5C). This argues for the existence of interaction or co-regulation of MiHA genes in discrete clusters.[41] Cluster 4 contains MiHA genes with the highest expression. Furthermore, nine MiHA genes showed differential expression among AML subtypes categorized according to the French-American-English classification[42] (FIG. 5C). Given the correlation between MAP abundance and mRNA expression, transcriptomic assessment of MiHA gene expression might be useful for selecting the best MiHA target for a given patient.

TABLE IV

Selected features of the novel lead MiHAs described herein.

| MiHA Name | Sequence | SEQ ID NO: | SNP ID | MAF Global/EA | $IC_{50}$ (nM) | BM/skin ratio | AMLs (RPKM) |
|---|---|---|---|---|---|---|---|
| HMMR-2$^{R/C}$ | KILEKEIR/CV | 1-3 | 299284 | 0.08/0.12 | 36 | 3.42 | 7.31 |
| NDC80-1$^{A/P}$ | HLEEQIA/PKV | 4-6 | 9051 | 0.18/0.23 | 118/63 | 4.01 | 7.47 |
| RASSF1-2$^{A/S}$ | SQA/SEIEQKI | 7-9 | 2073498 | 0.08/0.10 | 2,800 | 2.39 | 50.22 |
| BLM-1$^{V/I}$ | EEIPV/ISSHY | 10-12 | 7167216 | 0.07/0.07 | 15 | 9.01 | 10.50 |
| BLM-2$^{V/I}$ | EEIPV/ISSHYF | 13-15 | 7167216 | 0.07/0.07 | 18 | 9.01 | 10.50 |
| CCDC34-1$^{E/A}$ | AE/AIQEKKEI | 16-18 | 17244028 | 0.20/0.35 | 91 | 2.14 | 3.29 |
| CENPF-1$^{NQ/DQ/NH/DH}$ | QEN/DIQ/HNLQL | 19-23 | 3748692/3748693 | 0.10-0.20/0.09 | 518 | 3.33 | 10.98 |
| CPOX-1$^{N/H}$ | VEEADGN/HKQW | 24-26 | 1131857 | 0.24/0.13 | 149 | 2.06 | 13.50 |
| CPOX-2$^{N/H}$ | EEADGN/HKQWW | 27-29 | 1131857 | 0.24/0.13 | 26 | 2.06 | 13.50 |
| HJURP-1$^{E/G}$ | EE/GRGENTSY | 30-32 | 10511 | 0.18/0.10 | 220 | 9.49 | 7.70 |
| HMMR-3$^{R/C}$ | SESKIR/CVLL | 33-35 | 299284 | 0.08/0.12 | 528 | 3.42 | 7.31 |
| HY-UTY-2* | NESNTQKTY | 36 | n.a. | 1 (males) | 80 | 4.13 | 10.78 |
| MCPH1-1$^{R/I}$ | EEINLQR/INI | 37-39 | 2083914 | 0.08/0.15 | 104 | 2.09 | 6.17 |
| MIIP-1$^{K/E}$ | SEESAVPK/ERSW | 40-42 | 2295283 | 0.34/0.29 | 30/39 | 2.69 | 15.57 |
| MIIP-2$^{K/E}$ | EESAVPK/ERSW | 43-45 | 2295283 | 0.34/0.29 | 45/33 | 2.69 | 15.57 |
| MIS18BP1-1$^{E/D}$ | QE/DLIGKKEY | 46-48 | 34101857 | 0.10/0.08 | 145 | 3.58 | 41.14 |
| MKI67-1$^{G/S}$ | EELLAVG/SKF | 49-51 | 2152143 | 0.21/0.25 | 80/39 | 4.27 | 20.08 |

TABLE IV-continued

Selected features of the novel lead MiHAs described herein.

| MiHA Name | Sequence | SEQ ID NO: | SNP ID | MAF Global/EA | IC$_{50}$ (nM) | BM/skin ratio | AMLs (RPKM) |
|---|---|---|---|---|---|---|---|
| MKI67-2$^{D/G}$ | GED/GKGIKAL | 52-54 | 10082391 | 0.22/0.17 | 3,242 | 4.27 | 20.08 |
| PREX1-1$^{H/Q}$ | EEALGLYH/QW | 55-57 | 41283558 | 0.14/0.19 | 52 | 8.24 | 39.64 |
| RASSF1-1$^{A/S}$ | S/AEIEQKIKEY | 58-60 | 2073498 | 0.08/0.10 | 20/14 | 2.39 | 50.22 |
| SERF2-1$^{S/P}$ | TEMEIS/PRAA | 61-63 | 12702 | 0.21/0.10 | 235 | 3.40 | 61.61 |
| SMC4-1$^{N/S}$ | KEINEKSN/SIL | 64-66 | 33999879 | 0.05/0.05 | 861 | 3.49 | 42.25 |
| TESPA1-1$^{E/K}$ | EE/KEQSQSRW | 67-69 | 997173 | 0.25/0.07 | 86 | 5.49 | 24.07 |
| TRAPPC5-1$^{S/A}$ | AELQS/ARLAA | 70-72 | 6952 | 0.34/0.27 | 472 | 2.59 | 30.40 |
| TROAP-1$^{R/G}$ | QENQDPR/GRW | 73-75 | 8285 | 0.05/0.01 | 21 | 4.29 | 8.90 |
| ZWINT-1$^{G/R}$ | QELDG/RVFQKL | 76-78 | 2241666 | 0.26/0.37 | 210/339 | 2.61 | 16.83 |

In the sequences, the polymorphic residues are underlined and the MiHA variant(s) detected by MS is in bold. SNP ID = SNP identifier (SNP ID); MAF Global/EA: Global MAF reported by dbSNP, and the MAF in European Americans (EA) reported in the Exome Sequencing Project (ESP); IC$_{50}$ (nm): the predicted HLA binding affinity (IC$_{50}$) of the detected MiHA variants according to NetMHC (v.3.4)[38]; BM/skin ratio: relative BM/skin expression of the MiHA-coding transcripts. AMLs (RPKM): mean MiHA gene expression in primary AML samples (RPKM) obtained from TCGA.

TABLE V

Seven (7) other lead MiHAs identified among the 25 previously reported MiHAs

| MiHA name | Peptide sequence | HLA | dbSNP | Source gene | ENSG | SEQ ID NO: |
|---|---|---|---|---|---|---|
| ACC-2D (BCL2A1) | KEFEDGIINW | B4403 | rs3826007 | BCL2A1 | ENSG00000140379 | 248 |
| ACC-2G (BCL2A1) | KEFEDDIINW | B4403 | rs3826007 | BCL2A1 | ENSG00000140379 | 248 |
| BCL2A1-1N/K | VLQNVAFSV | A0201 | rs1138358 | BCL2A1 | ENSG00000140379 | 251 |
| FAM119 | AMLERQFTV | A0201 | rs2551949 | FAM119A | ENSG00000144401 | 267 |
| HA-1H/R | VLHDDLLEA | A0201 | rs1801284 | HMHA1 | ENSG00000180448 | 268 |
| HA-2V/M | YIGEVLVSV | A0201 | rs6173953 | MYO1G | ENSG00000136286 | 269 |
| HMMR-1V/A | SLQEKVAKA | A0201 | rs299295 | HMMR | ENSG00000072571 | 257 |

Figure 6A:
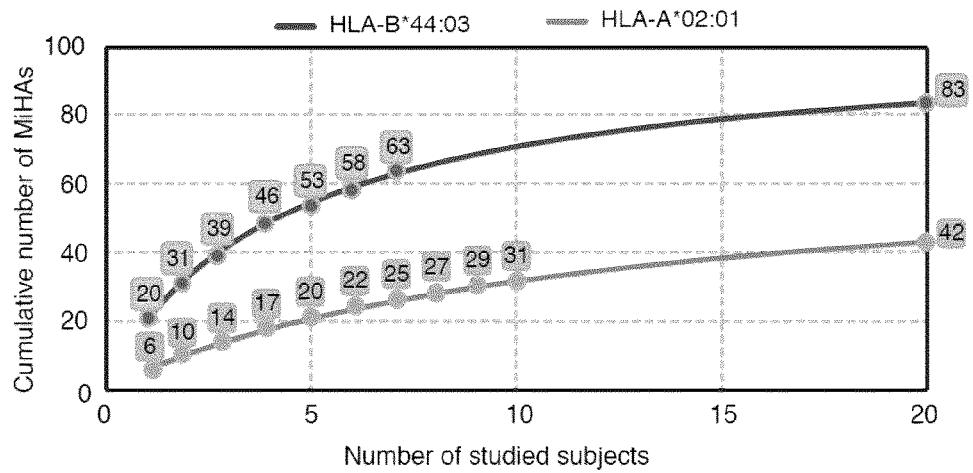
FIGS. 6A to 6C show that together the 39 lead MiHAs (of most clinical interest) (coded by 24 genes) would enable MiHA-targeted immunotherapy of almost all HLA-A*02:01;B*44:03 patients with hematological cancer (HC).

In the cohort of 13 individuals (ten HLA-A*02:01-positive and seven HLA-B*44:03-positive) used in the present study, 94 novel high-frequency MiHAs were identified. It was calculated that by increasing the number of individuals to 20 for each of these two allotypes, it may be expected to increase the total number of high-frequency MiHAs to a maximum of 125 (FIG. 6A). Such diminishing returns suggest that, from a clinical perspective, proteogenomic studies of other common HLA allotypes would be more rewarding. Recent reports suggest a dichotomy between generalist and specialist MHC class I allotypes, which present larger or smaller MAP repertoires, respectively.[43,44] Accordingly, the observation that HLA-B*44:03 presents more MiHAs (FIG. 6A) suggests that HLA-B*44:03 is a more generalist allotype, while HLA-A*02:01 is a more specialist allotype.

Figure 6B:
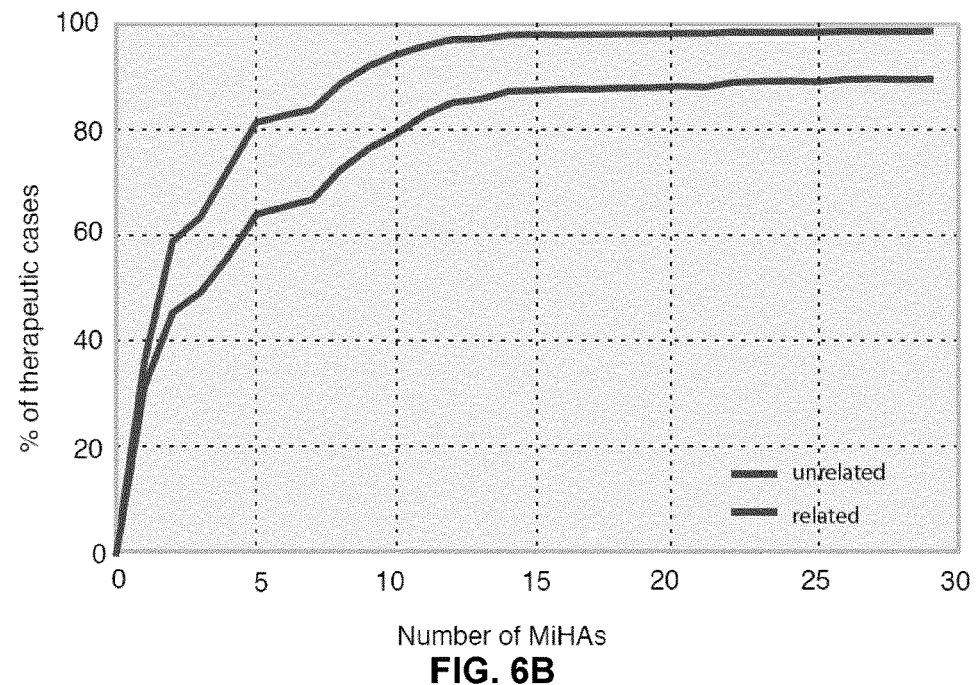
Figure 6C:
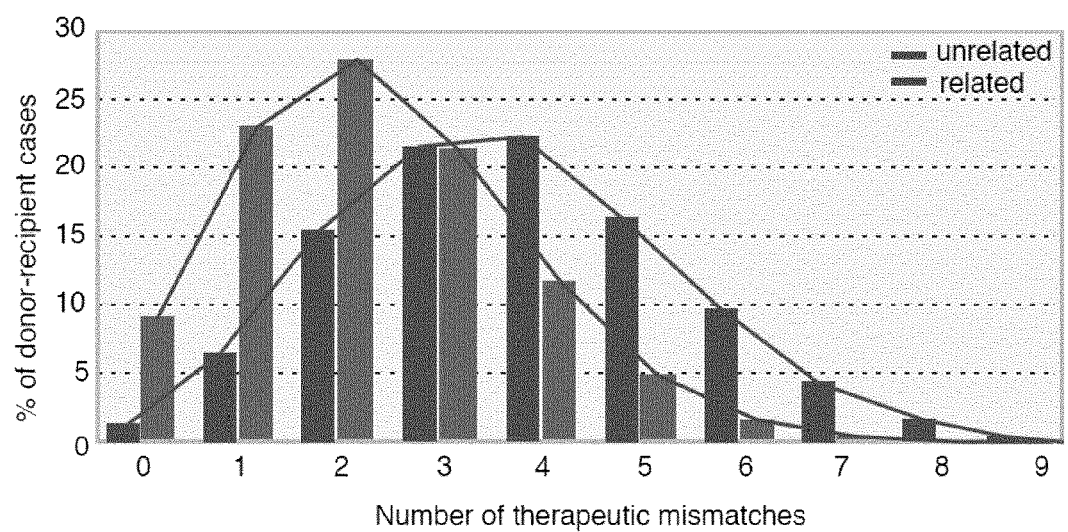

Example 4: Estimating the Frequency of Therapeutic MiHA Mismatches in Donor-Recipient Pairs It was next assessed whether the set of 39 optimal MiHAs defined in the present study is sufficient for MiHA-targeted immunotherapy of most patients. One million transplantation cases between related or unrelated HLA*02:01/HLA-B*44:03-positive European-American donor-recipient pairs were randomly simulated, and the number of therapeutic MiHA mismatches found in each case was determined. As shown in FIG. 6B, based on these simulations, it was predicted that at least one therapeutic mismatch would be found in 90% and 98% of related (lower curve) and unrelated (upper curve) donor-recipient pairs, respectively. In recent years, the number of unrelated donor transplants has surpassed the number of related donor transplants according to the CIBMTR. In the unrelated donor transplant situation, ≥2 therapeutic MiHA mismatches would be expected in 92% of cases with a mode of four mismatches (FIG. 6C, left bars). It may thus be estimated that the set of 39 optimal MiHAs would enable MiHA-targeted immunotherapy of practically all HLA-A*02:01;B*44:03 patients with HCs.

The scope of the claims should not be limited by the preferred embodiments set forth in the examples, but should be given the broadest interpretation consistent with the description as a whole.

REFERENCES

1. Schumacher T N, Schreiber R D. Neoantigens in cancer immunotherapy. *Science* 2015; 348:69-74.
2. Rosenberg S A, Restifo N P. Adoptive cell transfer as personalized immunotherapy for human cancer. *Science* 2015; 348:62-68.
3. Sharma P, Allison J P. The future of immune checkpoint therapy. *Science* 2015; 348:56-61.
4. Grupp S A, Kalos M, Barrett D, Aplenc R, Porter D L, Rheingold S R et al. Chimeric antigen receptor-modified T cells for acute lymphoid leukemia. *N. Engl. J Med* 2013; 368:1509-1518.
5. Maus M V, Fraietta J A, Levine B L, Kalos M, Zhao Y, June C H. Adoptive immunotherapy for cancer or viruses. *Annu. Rev. Immunol* 2014; 32:189-225.
6. Maus M V, Grupp S A, Porter D L, June C H. Antibody modified T cells: CARs take the front seat for hematologic malignancies. *Blood* 2014; 123:2625-2635.
7. Reddy P, Maeda Y, Liu C, Krijanovski O I, Korngold R, Ferrara J L. A crucial role for antigen-presenting cells and alloantigen expression in graft-versus-leukemia responses. *Nat. Med.* 2005; 11:1244-1249.
8. Vincent K, Roy D C, Perreault C. Next-generation leukemia immunotherapy. *Blood* 2011; 118:2951-2959.
9. Mutis T, Brand R, Gallardo D, van B A, Niederwieser D, Goulmy E. Graft-versus-host driven graft-versus-leukemia effect of minor histocompatibility antigen HA-1 in chronic myeloid leukemia patients. *Leukemia* 2010; 24:1388-1392.
10. Jenq R R, van den Brink M R. Allogeneic haematopoietic stem cell transplantation: individualized stem cell and immune therapy of cancer. *Nat Rev. Cancer* 2010; 10:213-221.
11. Roopenian D, Choi E Y, Brown A. The immunogenomics of minor histocompatibility antigens. *Immunol. Rev.* 2002; 190:86-94.
12. Mullally A, Ritz J. Beyond HLA: the significance of genomic variation for allogeneic hematopoietic stem cell transplantation. *Blood* 2007; 109:1355-1362.
13. Granados D P, Laumont C M, Thibault P, Perreault C. The nature of self for T cells—a systems-level perspective. *Curr. Opin. Immunol.* 2015; 34:1-8.
14. Warren E H, Zhang X C, Li S, Fan W, Storer B E, Chien J W et al. Effect of MHC and non-MHC donor/recipient genetic disparity on the outcome of allogeneic HCT. *Blood* 2012; 120:2796-2806.
15. Blazar B R, Murphy W J, Abedi M. Advances in graft-versus-host disease biology and therapy. *Nat Rev Immunol* 2012; 12:443-458.
16. Fontaine P, Roy-Proulx G, Knafo L, Baron C, Roy D C, Perreault C. Adoptive transfer of T lymphocytes targeted to a single immunodominant minor histocompatibility antigen eradicates leukemia cells without causing graft-versus-host disease. *Nat. Med.* 2001; 7:789-794.
17. Meunier M C, Delisle J S, Bergeron J, Rineau V, Baron C, Perreault C. T cells targeted against a single minor histocompatibility antigen can cure solid tumors. *Nat. Med.* 2005; 11:1222-1229.
18. Li N, Matte-Martone C, Zheng H, Cui W, Venkatesan S, Tan H S et al. Memory T cells from minor histocompatibility antigen-vaccinated and virus-immune donors improves GVL and immune reconstitution. *Blood* 2011; 118:5965-5976.
19. Blankenstein T, Leisegang M, Uckert W, Schreiber H. Targeting cancer-specific mutations by T cell receptor gene therapy. *Curr. Opin. Immunol.* 2015; 33:112-119.
20. Schreiber R D, Old L J, Smyth M J. Cancer immunoediting: integrating immunity's roles in cancer suppression and promotion. *Science* 2011; 331:1565-1570.
21. Spierings E, Hendriks M, Absi L, Canossi A, Chhaya S, Crowley J et al. Phenotype frequencies of autosomal minor histocompatibility antigens display significant differences among populations. *PLoS. Genet.* 2007; 3:e103.
22. Yadav M, Jhunjhunwala S, Phung Q T, Lupardus P, Tanguay J, Bumbaca S et al. Predicting immunogenic tumour mutations by combining mass spectrometry and exome sequencing. *Nature* 2014; 515:572-576.
23. Bleakley M, Riddell S R. Exploiting T cells specific for human minor histocompatibility antigens for therapy of leukemia. *Immunol. Cell Biol.* 2011; 89:396-407.
24. Hombrink P, Hassan C, Kester M G, Jahn L, Pont M J, de Ru A H et al. Identification of biological relevant minor histocompatibility antigens within the B-lymphocyte-derived HLA-ligandome using a reverse immunology approach. *Clin. Cancer Res.* 2015; 21:2177-2186.
25. Van Bergen C A, Rutten C E, Van Der Meijden E D, Van Luxemburg-Heijs S A, Lurvink E G, Houwing-Duistermaat J J et al. High-throughput characterization of 10 new minor histocompatibility antigens by whole genome association scanning. *Cancer Res.* 2010; 70:9073-9083.
26. Granados D P, Sriranganadane D, Daouda T, Zieger A, Laumont C M, Caron-Lizotte O et al. Impact of genomic polymorphism on the repertoire of human MHC class I-associated peptides. *Nat Commun* 2014; 5:3600.
27. Dolan B P, Sharma A A, Gibbs J S, Cunningham T J, Bennink J R, Yewdell J W. MHC class I antigen processing distinguishes endogenous antigens based on their translation from cellular vs. viral mRNA. *Proc. Natl. Acad. Sci. U.S.A* 2012; 109:7025-7030.
28. Yewdell J W. DRiPs solidify: progress in understanding endogenous MHC class I antigen processing. *Trends Immunol.* 2011; 32:548-558.
29. Nesvizhskii A I. Proteogenomics: concepts, applications and computational strategies. *Nat Methods* 2014; 11:1114-1125.
30. Fagerberg L, Hallstrom B M, Oksvold P, Kampf C, Djureinovic D, Odeberg J et al. Analysis of the human tissue-specific expression by genome-wide integration of transcriptomics and antibody-based proteomics. *Mol Cell Proteomics.* 2014; 13:397-406.
31. Wolfl M, Greenberg P D. Antigen-specific activation and cytokine-facilitated expansion of naive, human CD8+ T cells. *Nat Protoc.* 2014; 9:950-966.
32. Janelle V, Carli C, Taillefer J, Orio J, Delisle J S. Defining novel parameters for the optimal priming and expansion of minor histocompatibility antigen-specific T cells in culture. *J Transl. Med.* 2015; 13:123.
33. Abecasis G R, Altshuler D, Auton A, Brooks L D, Durbin R M, Gibbs R A et al. A map of human genome variation from population-scale sequencing. *Nature* 2010; 467: 1061-1073.
34. Spierings E. Minor histocompatibility antigens: past, present, and future. *Tissue Antigens* 2014; 84:374-60.
35. Majewski J, Ott J. Distribution and characterization of regulatory elements in the human genome. *Genome Res.* 2002; 12:1827-1836.
36. Asakura S, Hashimoto D, Takashima S, Sugiyama H, Maeda Y, Akashi K et al. Alloantigen expression on non-hematopoietic cells reduces graft-versus-leukemia effects in mice. *J. Clin. Invest* 2010; 120:2370-2378.
37. Flutter B, Edwards N, Fallah-Arani F, Henderson S, Chai J G, Sivakumaran S et al. Nonhematopoietic antigen blocks memory programming of alloreactive CD8+ T cells and drives their eventual exhaustion in mouse models of bone marrow transplantation. *J. Clin. Invest* 2010; 120: 3855-3868.
38. Fortier M H, Caron E, Hardy M P, Voisin G, Lemieux S, Perreault C et al. The MHC class I peptide repertoire is molded by the transcriptome. *J. Exp. Med.* 2008; 205: 595-610.
39. Hoof I, van Baarle D, Hildebrand W H, Kesmir C. Proteome sampling by the HLA class I antigen processing pathway. *PLoS. Comput. Biol.* 2012; 8:e1002517.
40. Granados D P, Yahyaoui W, Laumont C M, Daouda T, Muratore-Schroeder T L, Cote C et al. MHC I-associated peptides preferentially derive from transcripts bearing miRNA response elements. *Blood* 2012; 119:e181-e191.
41. Caron E, Vincent K, Fortier M H, Laverdure J P, Bramoullé A, Hardy M P et al. The MHC I immunopeptidome conveys to the cell surface an integrative view of cellular regulation. *Mol. Syst. Biol.* 2011; 7:533.
42. Bennett J M, Catovsky D, Daniel M T, Flandrin G, Galton D A, Gralnick H R et al. Proposed revised criteria for the classification of acute myeloid leukemia. A report of the French-American-British Cooperative Group. *Ann. Intern. Med.* 1985; 103:620-625.
43. Chappell P, Meziane E K, Harrison M, Magiera L, Hermann C, Mears L et al. Expression levels of MHC class I molecules are inversely correlated with promiscuity of peptide binding. *Elife.* 2015; 4:e05345.
44. Schellens I M, Hoof I, Meiring H D, Spijkers S N, Poelen M C, van Gaans-van den Brink J A et al. Comprehensive analysis of the naturally processed peptide repertoire: differences between HLA-A and B in the immunopeptidome. *PLoS. One.* 2015; 10:e0136417.
45. Caron E, Espona L, Kowalewski D J, Schuster H, Ternette N, Alpizar A et al. An open-source computational and data resource to analyze digital maps of immunopeptidomes. *Elife.* 2015; 4:
46. Heath W R, Carbone F R. The skin-resident and migratory immune system in steady state and memory: innate lymphocytes, dendritic cells and T cells. *Nat Immunol* 2013; 14:978-985.
47. Bollard C M, Barrett A J. Cytotoxic T lymphocytes for leukemia and lymphoma. *Hematology. Am. Soc. Hematol. Educ. Program.* 2014; 2014:565-569.
48. Yee C. The use of endogenous T cells for adoptive transfer. *Immunol Rev* 2014; 257:250-263.
49. Perreault C, Roy D C, Fortin C. Immunodominant minor histocompatibility antigens: the major ones. *Immunol. Today* 1998; 19:69-74.
50. Choi E Y, Christianson G J, Yoshimura Y, Jung N, Sproule T J, Malarkannan S et al. Real-time T-cell profiling identifies H60 as a major minor histocompatibility antigen in murine graft-versus-host disease. *Blood* 2002; 100:4259-4264.
51. Kim J, Ryu S J, Oh K, Ju J M, Jeon J Y, Nam G et al. Memory programming in CD8(+) T-cell differentiation is intrinsic and is not determined by CD4 help. *Nat Commun* 2015; 6:7994.
52. Rosinski S L, Stone B, Graves S S, Fuller D H, De Rosa S C, Spies G A et al. Development of a minor histocompatibility antigen vaccine regimen in the canine model of hematopoietic cell transplantation. *Transplantation* 2015; 99:2083-2094.
53. Turtle C J, Riddell S R. Genetically retargeting CD8+ lymphocyte subsets for cancer immunotherapy. *Curr. Opin. Immunol.* 2011; 23:299-305.
54. Nauerth M, Weissbrich B, Knall R, Franz T, Dossinger G, Bet J et al. TCR-ligand $k_{off}$ rate correlates with the protective capacity of antigen-specific CD8+ T cells for adoptive transfer. *Sci. Transl. Med.* 2013; 5:192ra87.
55. Ghosh A, Holland A M, van den Brink M R. Genetically engineered donor T cells to optimize graft-versus-tumor effects across MHC barriers. *Immunol Rev* 2014; 257: 226-236.
56. June C H, Riddell S R, Schumacher T N. Adoptive cellular therapy: A race to the finish line. *Sci. Transl. Med.* 2015; 7:280ps7.
57. Torikai H, Reik A, Soldner F, Warren E H, Yuen C, Zhou Y et al. Toward eliminating HLA class I expression to generate universal cells from allogeneic donors. *Blood* 2013; 122:1341-1349.
58. Inaguma Y, Akahori Y, Murayama Y, Shiraishi K, Tsuzuki-Iba S, Endoh A et al. Construction and molecular characterization of a T-cell receptor-like antibody and CAR-T cells specific for minor histocompatibility antigen HA-1H. *Gene Ther.* 2014; 21:575-584.

What is claimed is:

1. A method of treating cancer, said method comprising administering to a subject expressing a major histocompatibility complex (MHC) class I molecules of the HLA-A*02:01 allele in need thereof an effective amount of CD8+ T lymphocytes recognizing a MHC class I molecule of the HLA-A*02:01 allele loaded with a minor histocompatibility antigen (MiHA) peptide of 8 to 14 amino acids comprising the sequence (i) HLEEQIAKV (SEQ ID NO: 5) if said subject expresses the sequence HLEEQIAKV (SEQ ID NO: 5), or (ii) HLEEQIPKV (SEQ ID NO: 6) if said subject expresses the sequence HLEEQIPKV (SEQ ID NO: 6).

2. The method of claim 1, wherein said subject in need thereof is an allogeneic stem cell transplantation (ASCT) recipient.

3. The method of claim 1, wherein said cancer is a hematologic cancer.

4. The method of claim 3, wherein said hematologic cancer is leukemia.

5. The method of claim 1, wherein said CD8 T lymphocytes are ex vivo expanded primary CD8 T lymphocytes or CD8 T lymphocyte clones expressing a recombinant T cell receptor (TCR).

6. The method of claim 1, wherein said method further comprises administering an effective amount of the MiHA peptide recognized by said CD8+ T lymphocytes, and/or (ii) an antigen-presenting cell (APC) expressing at its surface MHC class I molecules comprising the MiHA peptide in their peptide binding groove.

7. The method of claim 1, wherein said method further comprises culturing and expanding said CD8 T lymphocytes in the presence of cells expressing said MHC class I molecule loaded with said MiHA peptide in vitro prior to administration to the subject, and wherein said CD8 T lymphocytes are from a second subject that does not express said MiHA peptide.

8. The method of claim 7, wherein said subject is an allogeneic stem cell transplantation (ASCT) recipient.

9. The method of claim 7, wherein said cancer is a hematologic cancer.

10. The method of claim 9, wherein said hematologic cancer is leukemia.

11. The method of claim 7, wherein said method further comprises administering an effective amount of the MiHA peptide defined in claim 1, and/or (ii) an antigen-presenting cell (APC) expressing at its surface MHC class I molecules comprising the MiHA peptide in their peptide binding groove.

12. The method of claim 1, wherein said MiHA peptide consists of the sequence HLEEQIA/PKV (SEQ ID NO: 4).

13. The method of claim 12, wherein said subject is an allogeneic stem cell transplantation (ASCT) recipient.

14. The method of claim 13, wherein said cancer is a hematologic cancer.

15. The method of claim 14, wherein said hematologic cancer is leukemia.

16. The method of claim 12, wherein said CD8 T lymphocytes are ex vivo expanded primary CD8 T lymphocytes or CD8 T lymphocyte clones expressing a recombinant T cell receptor (TCR).

17. The method of claim 12, wherein said method further comprises administering an effective amount of the MiHA peptide recognized by said CD8$^+$ T lymphocytes, and/or (ii) an antigen-presenting cell (APC) expressing at its surface MHC class I molecules comprising the MiHA peptide in their peptide binding groove.

18. The method of claim 12, wherein said method further comprises culturing and expanding said CD8 T lymphocytes in the presence of cells expressing said MHC class I molecule loaded with said MiHA peptide in vitro prior to administration to the subject, and wherein said CD8 T lymphocytes are from a second subject that does not express said MiHA peptide.

* * * * *